(12) United States Patent
Baylin et al.

(10) Patent No.: US 7,794,929 B2
(45) Date of Patent: Sep. 14, 2010

(54) GENOMIC SCREEN FOR EPIGENETICALLY SILENCED GENES ASSOCIATED WITH CANCER

(75) Inventors: Stephen B. Baylin, Baltimore, MD (US); James Herman, Baltimore, MD (US); Hiromu Suzuki, Sapporo (JP); David Sidransky, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 113 days.

(21) Appl. No.: 10/384,491

(22) Filed: Mar. 7, 2003

(65) Prior Publication Data

US 2003/0224040 A1    Dec. 4, 2003

Related U.S. Application Data

(60) Provisional application No. 60/362,422, filed on Mar. 7, 2002.

(51) Int. Cl.
*C12Q 1/68* (2006.01)
(52) U.S. Cl. .......................................................... 435/6
(58) Field of Classification Search ..................... 435/6, 435/91.1, 91.2
See application file for complete search history.

(56) References Cited

U.S. PATENT DOCUMENTS

| | | | | |
|---|---|---|---|---|
| 5,688,641 | A | * | 11/1997 | Sager et al. .................... 435/6 |
| 6,261,782 | B1 | | 7/2001 | Lizardi et al. |
| 6,372,436 | B1 | * | 4/2002 | Pouzyrev et al. .............. 435/6 |
| 6,756,200 | B2 | * | 6/2004 | Sukumar et al. ............... 435/6 |
| 6,759,200 | B1 | * | 7/2004 | Stanton, Jr. .................... 435/6 |
| 7,485,418 | B2 | * | 2/2009 | Goggins et al. ............... 435/6 |

FOREIGN PATENT DOCUMENTS

| | | | |
|---|---|---|---|
| WO | WO 01/77377 | A2 | 10/2001 |
| WO | WO 02/00927 | | 1/2002 |
| WO | WO 0200927 | A2 * | 1/2002 |

OTHER PUBLICATIONS

Eads et al., "Epigenetic Patterns in the Progression of Esophageal Adenocarcinoma," Cancer Research, Apr. 15, 2001, vol. 61, pp. 3410-3418.*
Shi et al., "Oligonucleotide-Based Microarray for DNA Methylation Analysis: Principles and Applications," Journal of Cellular Biochemistry, 2003, vol. 88, pp. 138-143.*
Yang et al., "Transcriptional Activation of Estrogen Receptor I in Human Brest Cancer Cells by Histone Deacetylase Inhibition," Cancer Research, Dec. 2000, vol. 60, pp. 6890-6894.*
Liang et al., "Analysis of Gene Induction in Human Fibroblasts and Bladder Cancer Cells Exposed to the Methylation Inhibitor 5-Aza-2'-deoxycytidine," Cancer Research, Feb. 15, 2002, vol. 62, pp. 961-966.*
Toyota et al., "Inactivation of CACNA1G, a T-Type Calcium Channel Gene, by Aberrant Methylation of Its 5' CpG Island in Human Tumors," Cancer Research, Sep. 15, 1999, vol. 59, pp. 4535-4541.*
Nephew et al., "Epigenetic gene silencing in cancer initiation and progression," Cancer Letters, 2003, vol. 190, pp. 125-133.*
Cameron et al., "Synergy of demethylation and histone deacetylase inhibition in the re-expression of genes silenced in cancer," Nature Genetics, Jan. 1999, vol. 21, pp. 103-107.*
Bachman et al., "Methylation-associated Silencing of the Tissue Inhibitor of *Metallaoproteinase-3* Gene Suggests a Suppressor in Kidney, Brain, and Other Human Cancers[1]" *Cancer Research*, 59:798-802 (1999).
Baylin et al., "Abnormal Patterns of DNA Methylation in Human Neoplasia: Potential Consequences for Tumor Progression," *Cancer Cells*, 3 (10):383-390 (1991).
Baylin, Stephen B., "DNA hypermethylation in tumorigenesis, epigenetics joins genetics," *TIG* 16 (4):168-174 (2000).
Cameron et al., "Synergy of demethylation and histone deacetylase inhibition in the re-expression of genes silenced in cancer," *Nature Genetics*, 21:103-107.
Chetcuti et al., "Loss of Annexin II Heavy and Light Chains in Prostate Cancer and Its Precursors[1]" *Cancer Research*, 61:6331-6334 (2001).
Esteller et al., "A Gene Hypermethylation Profile of Human Cancer,[1]" *Cancer Research*, 61:3225-3229 (2001).
Graff et al., "E-Cadherin Expression Is Silenced by DNA Hypermethylation in Human Breast and Prosate Carcinomas[1]" *Cancer Research*, 55:5195-5199 (1995).
Herman et al., "Distinct Patterns of Inactivation of $p15^{INK4B}$ and $p16^{INK4A}$" *Cancer Research*, 57:837-841 (1997).
Herman et al., "Hypermethylation-associated Inactivation Indicates a Tumor Suppressor Role for $p15^{INK4B1}$" *Cancer Research*, 56:722-727 (1996).
Herman et al., "Inactivation of the CDKN2/p16/MTS1 Gene Is Frequently Associated with Aberrant DNA Methylation in All Common Human Cancers[1]" *Cancer Research*, 55:4525-4530 (1995).
Herman et al., "Incidence and functional consequences of *hMLH1* promoter hypermethylation in colorectal carcinoma," *Proc. Natl. Acad. Sci. USA*, 95:6870-6875 (1998).
Herman et al., "Methylation-specific PCR: A novel PCR assay for methylation status of CpG islands," *Proc. Natl. Acad. Sci. USA*, 93:9821-9826 (1996).

(Continued)

*Primary Examiner*—Young J Kim
(74) *Attorney, Agent, or Firm*—DLA Piper LLP (US)

(57) ABSTRACT

A method of identifying epigenetically silenced genes, e.g., methylation silenced genes, in cancer cells is provided. In addition, methods of identifying a cancer by detecting epigenetic silencing of gene expression are provided, as are methods of treating a subject having such a cancer, for example, a colorectal cancer and/or gastric cancer. Reagents for practicing such methods also are provided.

15 Claims, 2 Drawing Sheets

OTHER PUBLICATIONS

Herman et al., "Silencing of the *VHL* tumor-suppressor gene by DNA methylation in renal carcinoma," *Proc. Natl. Acad. Sci. USA*, 91:9700-9704 (1994).

Katzenellenbogen et al., "Hypermethylation of the DAP-Kinase CpG Island Is a Common Alteration in B-Cell Malignancies," *Blood*, 93 (12):4347-4353 (1999).

Makos et al., "Regional DNA Hypermethylation at D17S5 Precedes 17p Structural Changes in the Progression of Renal Tumors[1]," *Cancer Research*, 53:2719 (1993).

Melkonyan et al., "SARPs: A family of secreted apoptosis-related proteins," *Proc. Natl. Acad. Sci. USA*, 94:13636-13641 (1997).

Ng et al., "Frequent Death-associated Protein Kinase Promoter Hypermethylation in Multiple Myeloma[1]," *Clinical Cancer Research*, 7:1724-1729 (2001).

Ottaviano et al., "Methylation of the Estrogen Receptor Gene CpG Island Marks Loss of Estrogen Receptor Expression in Human Breast Cancer Cells[1]" *Cancer Research*, 54:2552-2555 (1994).

Sakai et al., "Allele-specific Hypermethylation of the Retinoblastoma Tumor-suppressor Gene," *Am. J. Hum. Genet,.* 48:880-888 (1991).

Smiraglia et al., "Excessive CpG island hypermethylation in cancer cell lines versus primary human malignancies," *Human Molecular Genetics*, 10 (3):1413-1419 (2001).

Soengas et al., "Inactivation of the apoptosis effector *Apaf-1* in malignant melanoma," *Nature*, 409:207-211 (2001).

Sutcliffe et al., "Deletions of a differentially methylated CpG island at the *SNRPN* gene define a putative imprinting control region," *Nature Genetics*, 8:52-58 (1994).

Suzuki et al., "A genomic screen for genes upregulated by demethylation and histone deacetylase inhibition in human colorectal cancer," *nature genetics*, 31:141-149 (2002).

Toyota et al., "Aberrant Methylation of the *Cyclooxygenase* 2 CpG Island in Colorectal Tumors[1]" *Cancer Research*, 60:4044-4048 (2000).

Toyota et al., "CpG island methylator phenotype in colorectal cancer," *Proc. Natl. Acad. Sci. USA*, 96:8681-8686 (1999).

Ugolini et al., "Differential expression assay of chromosome arm 8p genes identifies Frizzled-related (FRP1/FRZB) and Fibroblast Growth Factor Receptor 1 (FGFR1) as candidate breast cancer genes," *Oncogene*, 18:1903-1910 (1999).

Ugolini et al., "WNT pathway and mammary carcinogenesis: Loss of expression of candidate tumor suppressor gene SFRP1 in most invasive carcinomas except of the medullary type," *Oncogene*, 20:5810-5817 (2001).

Xiong et al., "COBRA: a sensitive and quantitative DNA methylation assay," *Nucleic Acids Research*, 25 (12):2532-2534 (1997).

Yoshikawa et al., "SOCS-1, a negative regulator of the JAK/STAT pathway, is silenced by methylation in human hepatocellular carcinoma and shows growth-suppression activity," *nature genetics* 28:29-35 (2001).

Eads, et al., "Epigenetic Patterns in the Progression of Esophageal Adenocarcinoma", *Can Res*. 61:3410-3418, (Apr. 15, 2001).

Shi, et al., "Oligonucleotide-Based Microarray for DNA Methylation Analysis: Princeiples and Applications", *Jour. Cell. Biochem.* 88:138-143 (2003).

Yang, et al., "Transcriptional Activation of Estrogen Receptor I in Human Breat Cancer Cells by Histone Deacetylase Inhibition", *Can Res*. 60:6890-6894 (Dec. 2000).

Baylin et al., "Aberrant patterns of DNA methylation, chromatin formation and gene expression in cancer," *Human Molecular Genetics*, 10 (7):687-692 (2001).

Feinberg, Andrew P., "Methylation meets genomics," *nature genetics*, 27:9-10 (2001).

Howard et al., "Identification of receptors for neuromedin U and its role in feeding," *Nature* 406:70-74 (2000).

Merlo et al., "5' CpG island methylation is associated with transcriptional silencing of tumour suppressor *p16/CDKN2/MTS1* in human cancers," *Nature Medicine*, 1 (7):686-692 (1995).

Sasaki et al., "Colorectal carcinomas in mice lacking the catalytic subunit of PI(3)KK," *Nature*, 406:897-902 (2000).

Shi et al., "Expressed CpG Island Sequence Tag Microarray for Dual Screening of DNA Hypermethylation and Gene Silencing in Cancer Cells[1]," *Cancer Research*, 62:3214-3220 (2002).

Steenman et al., "Loss of imprinting of *IGF2* is linked to reduced expression and abnormal methylation of *H19* in Wilms' tumour," *Nature Genetics*, 7:433 (1994).

Velcich et al., "Colorectal Cancer in Mice Genetically Deficient in the Mucin Muc2," *Science*, 295:1726-1729 (2002) and Supplementary Material pp. 1-8.

Xu et al., "Artificial Neural Networks and Gene Filtering Distinguish Between Global Gene Expression Profiles of Barrett's Esophagus and Esophageal Cancer," *Cancer Research*, 62:3493-3497 (2002).

Yamashita et al., "Pharmacologic unmasking of epigenetically silenced tumor suppressor genes in esophageal squamous cell carcinoma," *Cancer Cell* 2:485-495 (2002).

Mariadason et al., "Genetic Reprogramming in Pathways of Colonic Cell Maturation Induced by Short Chain Fatty Acids: Comparison with Trichostatin A, Sulindac, and Curcumin and Implications for Chemoprevention of Colon Cancer", *Cancer Research*, 60:4561-4575 (2000).

Song et al., "Transcriptional Silencing of *Cyclooxygenase-2* by Hyper-Methylation of the 5' CpG Island in Human Gastric Carcinoma Cells", *Cancer Research*, 61:4628-4635 (2001).

\* cited by examiner

SEQUENCE LISTING

<160> NUMBER OF SEQ ID NOS: 296

<210> SEQ ID NO 1
<211> LENGTH: 28
<212> TYPE: DNA
<213> ORGANISM: Artificial sequence
<220> FEATURE:
<223> OTHER INFORMATION: Amplification primer

<400> SEQUENCE: 1
tgaagagaag tttataagaa ygttttgt                28

<210> SEQ ID NO 2
<211> LENGTH: 28
<212> TYPE: DNA
<213> ORGANISM: Artificial sequence
<220> FEATURE:
<223> OTHER INFORMATION: Amplification primer

<400> SEQUENCE: 2
caacaaatcc raacctaaaa actaccca                                28

<210> SEQ ID NO 3
<211> LENGTH: 28
<212> TYPE: DNA
<213> ORGANISM: Artificial sequence
<220> FEATURE:
<223> OTHER INFORMATION: Amplification primer

<400> SEQUENCE: 3
tcgcgtcgtt tttttttatt tattcgtc                                28

<210> SEQ ID NO 4
<211> LENGTH: 26
<212> TYPE: DNA
<213> ORGANISM: Artificial sequence
<220> FEATURE:
<223> OTHER INFORMATION: Amplification primer

<400> SEQUENCE: 4
aaactcacct taaccgaaac gcgacg                                  26

<210> SEQ ID NO 5
<211> LENGTH: 32
<212> TYPE: DNA
<213> ORGANISM: Artificial sequence
<220> FEATURE:
<223> OTHER INFORMATION: Amplification primer

<400> SEQUENCE: 5
gtttttgtgt tgttttttttt tatttatttg tt                          32

<210> SEQ ID NO 6
<211> LENGTH: 27
<212> TYPE: DNA
<213> ORGANISM: Artificial sequence
<220> FEATURE:
<223> OTHER INFORMATION: Amplification primer

<400> SEQUENCE: 6
aacaaaactc accttaacca aaacaca                                 27

<210> SEQ ID NO 7
<211> LENGTH: 25
<212> TYPE: DNA
<213> ORGANISM: Artificial sequence
<220> FEATURE:
<223> OTHER INFORMATION: Amplification primer

<400> SEQUENCE: 7
ggagtttatg agagggttgg agttt                                   25

<210> SEQ ID NO 8
<211> LENGTH: 25
<212> TYPE: DNA
<213> ORGANISM: Artificial sequence
<220> FEATURE:
<223> OTHER INFORMATION: Amplification primer

```
<400> SEQUENCE: 8
atcacccact acaaaacraa cccta                                                 25

<210> SEQ ID NO 9
<211> LENGTH: 26
<212> TYPE: DNA
<213> ORGANISM: Artificial sequence
<220> FEATURE:
<223> OTHER INFORMATION: Amplification primer

<400> SEQUENCE: 9
tggatacgta ttttcggcga cgtttc                                                26

<210> SEQ ID NO 10
<211> LENGTH: 25
<212> TYPE: DNA
<213> ORGANISM: Artificial sequence
<220> FEATURE:
<223> OTHER INFORMATION: Amplification primer

<400> SEQUENCE: 10
caacgacgcg tcgcaaaccg aatcg                                                 25

<210> SEQ ID NO 11
<211> LENGTH: 30
<212> TYPE: DNA
<213> ORGANISM: Artificial sequence
<220> FEATURE:
<223> OTHER INFORMATION: Amplification primer

<400> SEQUENCE: 11
tggtttttgt ggatatgtat ttttggtgat                                            30

<210> SEQ ID NO 12
<211> LENGTH: 28
<212> TYPE: DNA
<213> ORGANISM: Artificial sequence
<220> FEATURE:
<223> OTHER INFORMATION: Amplification primer

<400> SEQUENCE: 12
aattcctcca acaacacatc acaaacca                                              28

<210> SEQ ID NO 13
<211> LENGTH: 27
<212> TYPE: DNA
<213> ORGANISM: Artificial sequence
<220> FEATURE:
<223> OTHER INFORMATION: Amplification primer

<400> SEQUENCE: 13
ggggaattgg ygttaaattt tgtaggg                                               27

<210> SEQ ID NO 14
<211> LENGTH: 25
<212> TYPE: DNA
<213> ORGANISM: Artificial sequence
<220> FEATURE:
<223> OTHER INFORMATION: Amplification primer

<400> SEQUENCE: 14
aaacaacttc craaccccc taaac                                                  25

<210> SEQ ID NO 15
```

```
<211> LENGTH: 22
<212> TYPE: DNA
<213> ORGANISM: Artificial sequence
<220> FEATURE:
<223> OTHER INFORMATION: Amplification primer

<400> SEQUENCE: 15
ttcggaagtt gtttcggttc gc                                                    22

<210> SEQ ID NO 16
<211> LENGTH: 26
<212> TYPE: DNA
<213> ORGANISM: Artificial sequence
<220> FEATURE:
<223> OTHER INFORMATION: Amplification primer

<400> SEQUENCE: 16
cgaacatcgt aactacaaaa aacgcg                                                26

<210> SEQ ID NO 17
<211> LENGTH: 26
<212> TYPE: DNA
<213> ORGANISM: Artificial sequence
<220> FEATURE:
<223> OTHER INFORMATION: Amplification primer

<400> SEQUENCE: 17
gggttttgga agttgttttg gtttgt                                                26

<210> SEQ ID NO 18
<211> LENGTH: 31
<212> TYPE: DNA
<213> ORGANISM: Artificial sequence
<220> FEATURE:
<223> OTHER INFORMATION: Amplification primer

<400> SEQUENCE: 18
aaccacaaac atcataacta caaaaaacac a                                          31

<210> SEQ ID NO 19
<211> LENGTH: 28
<212> TYPE: DNA
<213> ORGANISM: Artificial sequence
<220> FEATURE:
<223> OTHER INFORMATION: Amplification primer

<400> SEQUENCE: 19
tggttttgtt ttttaagggg tgttgagt                                              28

<210> SEQ ID NO 20
<211> LENGTH: 29
<212> TYPE: DNA
<213> ORGANISM: Artificial sequence
<220> FEATURE:
<223> OTHER INFORMATION: Amplification primer

<400> SEQUENCE: 20
acactaactc craaaactac aaaactaaa                                             29

<210> SEQ ID NO 21
<211> LENGTH: 27
<212> TYPE: DNA
<213> ORGANISM: Artificial sequence
<220> FEATURE:
<223> OTHER INFORMATION: Amplification primer

<400> SEQUENCE: 21
```

```
ttagttttgt agttttygga gttagtg                              27

<210> SEQ ID NO 22
<211> LENGTH: 27
<212> TYPE: DNA
<213> ORGANISM: Artificial sequence
<220> FEATURE:
<223> OTHER INFORMATION: Amplification primer

<400> SEQUENCE: 22
tcctaccrca aacttccaaa aacctcc                              27

<210> SEQ ID NO 23
<211> LENGTH: 26
<212> TYPE: DNA
<213> ORGANISM: Artificial sequence
<220> FEATURE:
<223> OTHER INFORMATION: Amplification primer

<400> SEQUENCE: 23
tgtagttttc ggagttagtg tcgcgc                               26

<210> SEQ ID NO 24
<211> LENGTH: 25
<212> TYPE: DNA
<213> ORGANISM: Artificial sequence
<220> FEATURE:
<223> OTHER INFORMATION: Amplification primer

<400> SEQUENCE: 24
cctacgatcg aaaacgacgc gaacg                                25

<210> SEQ ID NO 25
<211> LENGTH: 30
<212> TYPE: DNA
<213> ORGANISM: Artificial sequence
<220> FEATURE:
<223> OTHER INFORMATION: Amplification primer

<400> SEQUENCE: 25
gttttgtagt ttttggagtt agtgttgtgt                           30

<210> SEQ ID NO 26
<211> LENGTH: 30
<212> TYPE: DNA
<213> ORGANISM: Artificial sequence
<220> FEATURE:
<223> OTHER INFORMATION: Amplification primer

<400> SEQUENCE: 26
ctcaacctac aatcaaaaac aacacaaaca                           30

<210> SEQ ID NO 27
<211> LENGTH: 30
<212> TYPE: DNA
<213> ORGANISM: Artificial sequence
<220> FEATURE:
<223> OTHER INFORMATION: Amplification primer

<400> SEQUENCE: 27
gttaaagttt agttggtttt aygtaattat                           30

<210> SEQ ID NO 28
<211> LENGTH: 28
<212> TYPE: DNA
```

```
<213> ORGANISM: Artificial sequence
<220> FEATURE:
<223> OTHER INFORMATION: Amplification primer

<400> SEQUENCE: 28
cttttaattt ccrtaaccct cctttat                                        28

<210> SEQ ID NO 29
<211> LENGTH: 28
<212> TYPE: DNA
<213> ORGANISM: Artificial sequence
<220> FEATURE:
<223> OTHER INFORMATION: Amplification primer

<400> SEQUENCE: 29
attaattttg gagcgttttt cgcgcgtc                                       28

<210> SEQ ID NO 30
<211> LENGTH: 25
<212> TYPE: DNA
<213> ORGANISM: Artificial sequence
<220> FEATURE:
<223> OTHER INFORMATION: Amplification primer

<400> SEQUENCE: 30
tccacgcacc gaaccaaaaa ccccg                                          25

<210> SEQ ID NO 31
<211> LENGTH: 32
<212> TYPE: DNA
<213> ORGANISM: Artificial sequence
<220> FEATURE:
<223> OTHER INFORMATION: Amplification primer

<400> SEQUENCE: 31
atgtattaat tttggagtgt tttttgtgtg tt                                  32

<210> SEQ ID NO 32
<211> LENGTH: 27
<212> TYPE: DNA
<213> ORGANISM: Artificial sequence
<220> FEATURE:
<223> OTHER INFORMATION: Amplification primer

<400> SEQUENCE: 32
tctccacaca ccaaaccaaa aacccca                                        27

<210> SEQ ID NO 33
<211> LENGTH: 23
<212> TYPE: DNA
<213> ORGANISM: Artificial sequence
<220> FEATURE:
<223> OTHER INFORMATION: Amplification primer

<400> SEQUENCE: 33
agataaagag gagagaaagt ttg                                            23

<210> SEQ ID NO 34
<211> LENGTH: 20
<212> TYPE: DNA
<213> ORGANISM: Artificial sequence
<220> FEATURE:
<223> OTHER INFORMATION: Amplification primer

<400> SEQUENCE: 34
ccaacaacaa aaaccraac                                                 20
```

<210> SEQ ID NO 35
<211> LENGTH: 25
<212> TYPE: DNA
<213> ORGANISM: Artificial sequence
<220> FEATURE:
<223> OTHER INFORMATION: Amplification primer

<400> SEQUENCE: 35
attcgtagaa ggtagcgcgg tcgtc                                      25

<210> SEQ ID NO 36
<211> LENGTH: 23
<212> TYPE: DNA
<213> ORGANISM: Artificial sequence
<220> FEATURE:
<223> OTHER INFORMATION: Amplification primer

<400> SEQUENCE: 36
ctcacctacc ccgctcgacc gcg                                        23

<210> SEQ ID NO 37
<211> LENGTH: 29
<212> TYPE: DNA
<213> ORGANISM: Artificial sequence
<220> FEATURE:
<223> OTHER INFORMATION: Amplification primer

<400> SEQUENCE: 37
atatatttgt agaaggtagt gtggttgtt                                  29

<210> SEQ ID NO 38
<211> LENGTH: 25
<212> TYPE: DNA
<213> ORGANISM: Artificial sequence
<220> FEATURE:
<223> OTHER INFORMATION: Amplification primer

<400> SEQUENCE: 38
tcctcaccta ccccactcaa ccaca                                      25

<210> SEQ ID NO 39
<211> LENGTH: 23
<212> TYPE: DNA
<213> ORGANISM: Artificial sequence
<220> FEATURE:
<223> OTHER INFORMATION: Amplification primer

<400> SEQUENCE: 39
gttatyggta tagttgattt tgt                                        23

<210> SEQ ID NO 40
<211> LENGTH: 23
<212> TYPE: DNA
<213> ORGANISM: Artificial sequence
<220> FEATURE:
<223> OTHER INFORMATION: Amplification primer

<400> SEQUENCE: 40 ctcccccaa atcattccra taa                                         23

<210> SEQ ID NO 41
<211> LENGTH: 28
<212> TYPE: DNA
<213> ORGANISM: Artificial sequence
<220> FEATURE:

<223> OTHER INFORMATION: Amplification primer

<400> SEQUENCE: 41
gaggtattag tgagattgag agagattt                                      28

<210> SEQ ID NO 42
<211> LENGTH: 29
<212> TYPE: DNA
<213> ORGANISM: Artificial sequence
<220> FEATURE:
<223> OTHER INFORMATION: Amplification primer

<400> SEQUENCE: 42
ccctaaaaaa aaccaacaac aaaatccca                                     29

<210> SEQ ID NO 43
<211> LENGTH: 24
<212> TYPE: DNA
<213> ORGANISM: Artificial sequence
<220> FEATURE:
<223> OTHER INFORMATION: Amplification primer

<400> SEQUENCE: 43
ttcgtcgtgg tggttggagg gcgc                                          24

<210> SEQ ID NO 44
<211> LENGTH: 25
<212> TYPE: DNA
<213> ORGANISM: Artificial sequence
<220> FEATURE:
<223> OTHER INFORMATION: Amplification primer

<400> SEQUENCE: 44
caacgcacaa ccaacgcgaa cgacg                                         25

<210> SEQ ID NO 45
<211> LENGTH: 28
<212> TYPE: DNA
<213> ORGANISM: Artificial sequence
<220> FEATURE:
<223> OTHER INFORMATION: Amplification primer

<400> SEQUENCE: 45
ttattttgtt gtggtggttg gagggtgt                                      28

<210> SEQ ID NO 46
<211> LENGTH: 28
<212> TYPE: DNA
<213> ORGANISM: Artificial sequence
<220> FEATURE:
<223> OTHER INFORMATION: Amplification primer

<400> SEQUENCE: 46
ccccaacaca caaccaacac aaacaaca                                      28

<210> SEQ ID NO 47
<211> LENGTH: 25
<212> TYPE: DNA
<213> ORGANISM: Artificial sequence
<220> FEATURE:
<223> OTHER INFORMATION: Amplification primer

<400> SEQUENCE: 47
aagggattgt tagaggtagg yggag                                         25

```
<210> SEQ ID NO 48
<211> LENGTH: 25
<212> TYPE: DNA
<213> ORGANISM: Artificial sequence
<220> FEATURE:
<223> OTHER INFORMATION: Amplification primer

<400> SEQUENCE: 48
cacaaaactc atacctccaa cctca                                    25

<210> SEQ ID NO 49
<211> LENGTH: 24
<212> TYPE: DNA
<213> ORGANISM: Artificial sequence
<220> FEATURE:
<223> OTHER INFORMATION: Amplification primer

<400> SEQUENCE: 49
ttatggagga agtgagaaag ttgg                                     24

<210> SEQ ID NO 50
<211> LENGTH: 24
<212> TYPE: DNA
<213> ORGANISM: Artificial sequence
<220> FEATURE:
<223> OTHER INFORMATION: Amplification primer

<400> SEQUENCE: 50
tctacacccc cctacccact aaaa                                     24

<210> SEQ ID NO 51
<211> LENGTH: 29
<212> TYPE: DNA
<213> ORGANISM: Artificial sequence
<220> FEATURE:
<223> OTHER INFORMATION: Amplification primer

<400> SEQUENCE: 51
taggaatttg gggtagaaaa tgaatattt                                29

<210> SEQ ID NO 52
<211> LENGTH: 27
<212> TYPE: DNA
<213> ORGANISM: Artificial sequence
<220> FEATURE:
<223> OTHER INFORMATION: Amplification primer

<400> SEQUENCE: 52
acccraacta taaactccc caaaatc                                   27

<210> SEQ ID NO 53
<211> LENGTH: 25
<212> TYPE: DNA
<213> ORGANISM: Artificial sequence
<220> FEATURE:
<223> OTHER INFORMATION: Amplification primer

<400> SEQUENCE: 53
ggagagttag gygggttaga gttga                                    25

<210> SEQ ID NO 54
<211> LENGTH: 25
<212> TYPE: DNA
<213> ORGANISM: Artificial sequence
<220> FEATURE:
<223> OTHER INFORMATION: Amplification primer
```

```
<400> SEQUENCE: 54
ctacaaaaaa aataaccata tctcc                                         25

<210> SEQ ID NO 55
<211> LENGTH: 26
<212> TYPE: DNA
<213> ORGANISM: Artificial sequence
<220> FEATURE:
<223> OTHER INFORMATION: Amplification primer

<400> SEQUENCE: 55
gatttttcgc ggcggtatcg tagcgc                                        26

<210> SEQ ID NO 56
<211> LENGTH: 27
<212> TYPE: DNA
<213> ORGANISM: Artificial sequence
<220> FEATURE:
<223> OTHER INFORMATION: Amplification primer

<400> SEQUENCE: 56
caaccccttc cttcgttaaa caacgcg                                       27

<210> SEQ ID NO 57
<211> LENGTH: 31
<212> TYPE: DNA
<213> ORGANISM: Artificial sequence
<220> FEATURE:
<223> OTHER INFORMATION: Amplification primer

<400> SEQUENCE: 57
gattagattt tttgtggtgg tattgtagtg t                                  31

<210> SEQ ID NO 58
<211> LENGTH: 29
<212> TYPE: DNA
<213> ORGANISM: Artificial sequence
<220> FEATURE:
<223> OTHER INFORMATION: Amplification primer

<400> SEQUENCE: 58
aacaacccct tccttcatta aacaacaca                                     29

<210> SEQ ID NO 59
<211> LENGTH: 23
<212> TYPE: DNA
<213> ORGANISM: Artificial sequence
<220> FEATURE:
<223> OTHER INFORMATION: Amplification primer

<400> SEQUENCE: 59
gaagggggta ggttagggag agg                                           23

<210> SEQ ID NO 60
<211> LENGTH: 22
<212> TYPE: DNA
<213> ORGANISM: Artificial sequence
<220> FEATURE:
<223> OTHER INFORMATION: Amplification primer

<400> SEQUENCE: 60
ccaccataac tccctcctac tc                                            22

<210> SEQ ID NO 61
<211> LENGTH: 26
```

```
<212> TYPE: DNA
<213> ORGANISM: Artificial sequence
<220> FEATURE:
<223> OTHER INFORMATION: Amplification primer

<400> SEQUENCE: 61
tgatcgggac gcgtcgtttt ttcgtc                                      26

<210> SEQ ID NO 62
<211> LENGTH: 25
<212> TYPE: DNA
<213> ORGANISM: Artificial sequence
<220> FEATURE:
<223> OTHER INFORMATION: Amplification primer

<400> SEQUENCE: 62
cttcgcctcc cactctcgcg cgacg                                       25

<210> SEQ ID NO 63
<211> LENGTH: 31
<212> TYPE: DNA
<213> ORGANISM: Artificial sequence
<220> FEATURE:
<223> OTHER INFORMATION: Amplification primer

<400> SEQUENCE: 63
ttatgtgatt gggatgtgtt gttttttttgt t                               31

<210> SEQ ID NO 64
<211> LENGTH: 27
<212> TYPE: DNA
<213> ORGANISM: Artificial sequence
<220> FEATURE:
<223> OTHER INFORMATION: Amplification primer

<400> SEQUENCE: 64
cccttcacct cccactctca cacaaca                                     27

<210> SEQ ID NO 65
<211> LENGTH: 25
<212> TYPE: DNA
<213> ORGANISM: Artificial sequence
<220> FEATURE:
<223> OTHER INFORMATION: Amplification primer

<400> SEQUENCE: 65
tggtatttag gaggttggtg aaata                                       25

<210> SEQ ID NO 66
<211> LENGTH: 25
<212> TYPE: DNA
<213> ORGANISM: Artificial sequence
<220> FEATURE:
<223> OTHER INFORMATION: Amplification primer

<400> SEQUENCE: 66
accctcaatc tcctactcca ttaaa                                       25

<210> SEQ ID NO 67
<211> LENGTH: 24
<212> TYPE: DNA
<213> ORGANISM: Artificial sequence
<220> FEATURE:
<223> OTHER INFORMATION: Amplification primer

<400> SEQUENCE: 67
```

| | |
|---|---|
| gcggggttaa agcgggtcgt cgc | 24 |

<210> SEQ ID NO 68
<211> LENGTH: 28
<212> TYPE: DNA
<213> ORGANISM: Artificial sequence
<220> FEATURE:
<223> OTHER INFORMATION: Amplification primer

<400> SEQUENCE: 68

| | |
|---|---|
| aaaaatatac gaactaatac gcgccacg | 28 |

<210> SEQ ID NO 69
<211> LENGTH: 26
<212> TYPE: DNA
<213> ORGANISM: Artificial sequence
<220> FEATURE:
<223> OTHER INFORMATION: Amplification primer

<400> SEQUENCE: 69

| | |
|---|---|
| gggtggggtt aaagtgggtt gtttgt | 26 |

<210> SEQ ID NO 70
<211> LENGTH: 30
<212> TYPE: DNA
<213> ORGANISM: Artificial sequence
<220> FEATURE:
<223> OTHER INFORMATION: Amplification primer

<400> SEQUENCE: 70

| | |
|---|---|
| ttaaaaatat acaaactaat acacaccaca | 30 |

<210> SEQ ID NO 71
<211> LENGTH: 28
<212> TYPE: DNA
<213> ORGANISM: Artificial sequence
<220> FEATURE:
<223> OTHER INFORMATION: Amplification primer

<400> SEQUENCE: 71

| | |
|---|---|
| gtagttgttg ttgttgttgt tgttgttt | 28 |

<210> SEQ ID NO 72
<211> LENGTH: 29
<212> TYPE: DNA
<213> ORGANISM: Artificial sequence
<220> FEATURE:
<223> OTHER INFORMATION: Amplification primer

<400> SEQUENCE: 72

| | |
|---|---|
| aacatcttac cctctaaaca aatttatac | 29 |

<210> SEQ ID NO 73
<211> LENGTH: 29
<212> TYPE: DNA
<213> ORGANISM: Artificial sequence
<220> FEATURE:
<223> OTHER INFORMATION: Amplification primer

<400> SEQUENCE: 73

| | |
|---|---|
| gtttcgtttt tataatttgc gacgtggtc | 29 |

<210> SEQ ID NO 74
<211> LENGTH: 25
<212> TYPE: DNA
<213> ORGANISM: Artificial sequence

```
<220> FEATURE:
<223> OTHER INFORMATION: Amplification primer

<400> SEQUENCE: 74
ctcaaaacgc caaacccgaa ccgcg                                            25

<210> SEQ ID NO 75
<211> LENGTH: 32
<212> TYPE: DNA
<213> ORGANISM: Artificial sequence
<220> FEATURE:
<223> OTHER INFORMATION: Amplification primer

<400> SEQUENCE: 75
gtgatgttag ttttgttttt ataatttgtg at                                    32

<210> SEQ ID NO 76
<211> LENGTH: 27
<212> TYPE: DNA
<213> ORGANISM: Artificial sequence
<220> FEATURE:
<223> OTHER INFORMATION: Amplification primer

<400> SEQUENCE: 76 tccctcaaa acaccaaacc caaacca                                           27

<210> SEQ ID NO 77
<211> LENGTH: 27
<212> TYPE: DNA
<213> ORGANISM: Artificial sequence
<220> FEATURE:
<223> OTHER INFORMATION: Amplification primer

<400> SEQUENCE: 77
gaatttattg gtgtgtttag tagtygg                                          27

<210> SEQ ID NO 78
<211> LENGTH: 26
<212> TYPE: DNA
<213> ORGANISM: Artificial sequence
<220> FEATURE:
<223> OTHER INFORMATION: Amplification primer

<400> SEQUENCE: 78
cccraaccac aaaatcrcct atcaac                                           26

<210> SEQ ID NO 79
<211> LENGTH: 25
<212> TYPE: DNA
<213> ORGANISM: Artificial sequence
<220> FEATURE:
<223> OTHER INFORMATION: Amplification primer

<400> SEQUENCE: 79
gggagggcgt tcggtttgta cgttc                                            25

<210> SEQ ID NO 80
<211> LENGTH: 25
<212> TYPE: DNA
<213> ORGANISM: Artificial sequence
<220> FEATURE:
<223> OTHER INFORMATION: Amplification primer

<400> SEQUENCE: 80
cataaacgat cgcccaacga cgccg                                            25
```

<210> SEQ ID NO 81
<211> LENGTH: 28
<212> TYPE: DNA
<213> ORGANISM: Artificial sequence
<220> FEATURE:
<223> OTHER INFORMATION: Amplification primer

<400> SEQUENCE: 81
agtgggaggg tgtttggttt gtatgttt                                28

<210> SEQ ID NO 82
<211> LENGTH: 30
<212> TYPE: DNA
<213> ORGANISM: Artificial sequence
<220> FEATURE:
<223> OTHER INFORMATION: Amplification primer

<400> SEQUENCE: 82
caaatcataa acaatcaccc aacaacacca                              30

<210> SEQ ID NO 83
<211> LENGTH: 24
<212> TYPE: DNA
<213> ORGANISM: Artificial sequence
<220> FEATURE:
<223> OTHER INFORMATION: Amplification primer

<400> SEQUENCE: 83
aggaggaagt tttaggagtt tttg                                    24

<210> SEQ ID NO 84
<211> LENGTH: 24
<212> TYPE: DNA
<213> ORGANISM: Artificial sequence
<220> FEATURE:
<223> OTHER INFORMATION: Amplification primer

<400> SEQUENCE: 84
ctaactcacc acaaaataat aacc                                    24

<210> SEQ ID NO 85
<211> LENGTH: 24
<212> TYPE: DNA
<213> ORGANISM: Artificial sequence
<220> FEATURE:
<223> OTHER INFORMATION: Amplification primer

<400> SEQUENCE: 85
tcgtggttgg cgttcggcgc gtga                                    24

<210> SEQ ID NO 86
<211> LENGTH: 24
<212> TYPE: DNA
<213> ORGANISM: Artificial sequence
<220> FEATURE:
<223> OTHER INFORMATION: Amplification primer

<400> SEQUENCE: 86
accgccgcgc aactcgacta ccga                                    24

<210> SEQ ID NO 87
<211> LENGTH: 24
<212> TYPE: DNA
<213> ORGANISM: Artificial sequence
<220> FEATURE:
<223> OTHER INFORMATION: Amplification primer

<400> SEQUENCE: 87
ttgtggttgg tgtttggtgt gtga						24

<210> SEQ ID NO 88
<211> LENGTH: 24
<212> TYPE: DNA
<213> ORGANISM: Artificial sequence
<220> FEATURE:
<223> OTHER INFORMATION: Amplification primer

<400> SEQUENCE: 88
ataccaccac acaactcaac tacc						24

<210> SEQ ID NO 89
<211> LENGTH: 30
<212> TYPE: DNA
<213> ORGANISM: Artificial sequence
<220> FEATURE:
<223> OTHER INFORMATION: Amplification primer

<400> SEQUENCE: 89
gtgttttata aatgtgaata aatagaattt					30

<210> SEQ ID NO 90
<211> LENGTH: 28
<212> TYPE: DNA
<213> ORGANISM: Artificial sequence
<220> FEATURE:
<223> OTHER INFORMATION: Amplification primer

<400> SEQUENCE: 90
caatacactc taaaataata acaaaacc					28

<210> SEQ ID NO 91
<211> LENGTH: 26
<212> TYPE: DNA
<213> ORGANISM: Artificial sequence
<220> FEATURE:
<223> OTHER INFORMATION: Amplification primer

<400> SEQUENCE: 91
ttttagggtt gtcgggagag tcgcgg					26

<210> SEQ ID NO 92
<211> LENGTH: 27
<212> TYPE: DNA
<213> ORGANISM: Artificial sequence
<220> FEATURE:
<223> OTHER INFORMATION: Amplification primer

<400> SEQUENCE: 92
caaccgaacg aaaaaaaaac gaccccg					27

<210> SEQ ID NO 93
<211> LENGTH: 28
<212> TYPE: DNA
<213> ORGANISM: Artificial sequence
<220> FEATURE:
<223> OTHER INFORMATION: Amplification primer

<400> SEQUENCE: 93 gtggtttag ggttgttggg agagttgt					28

<210> SEQ ID NO 94

<211> LENGTH: 31
<212> TYPE: DNA
<213> ORGANISM: Artificial sequence
<220> FEATURE:
<223> OTHER INFORMATION: Amplification primer

<400> SEQUENCE: 94
aaaacaacca acaaaaaaa aaacaacccc a                                31

<210> SEQ ID NO 95
<211> LENGTH: 29
<212> TYPE: DNA
<213> ORGANISM: Artificial sequence
<220> FEATURE:
<223> OTHER INFORMATION: Amplification primer

<400> SEQUENCE: 95
ggtattagaa aattttggtt tttaggggg                                  29

<210> SEQ ID NO 96
<211> LENGTH: 26
<212> TYPE: DNA
<213> ORGANISM: Artificial sequence
<220> FEATURE:
<223> OTHER INFORMATION: Amplification primer

<400> SEQUENCE: 96
acccacccac ctactacact aaccta                                     26

<210> SEQ ID NO 97
<211> LENGTH: 26
<212> TYPE: DNA
<213> ORGANISM: Artificial sequence
<220> FEATURE:
<223> OTHER INFORMATION: Amplification primer

<400> SEQUENCE: 97
acgggaagta gttatcggga gttcgc                                     26

<210> SEQ ID NO 98
<211> LENGTH: 25
<212> TYPE: DNA
<213> ORGANISM: Artificial sequence
<220> FEATURE:
<223> OTHER INFORMATION: Amplification primer

<400> SEQUENCE: 98
gacgaaacct aaattcccac gcccg                                      25

<210> SEQ ID NO 99
<211> LENGTH: 29
<212> TYPE: DNA
<213> ORGANISM: Artificial sequence
<220> FEATURE:
<223> OTHER INFORMATION: Amplification primer

<400> SEQUENCE: 99
tggatgggaa gtagttattg ggagtttgt                                  29

<210> SEQ ID NO 100
<211> LENGTH: 28
<212> TYPE: DNA
<213> ORGANISM: Artificial sequence
<220> FEATURE:
<223> OTHER INFORMATION: Amplification primer

<400> SEQUENCE: 100
ctcaacaaaa cctaaattcc cacaccca                                              28

<210> SEQ ID NO 101
<211> LENGTH: 29
<212> TYPE: DNA
<213> ORGANISM: Artificial sequence
<220> FEATURE:
<223> OTHER INFORMATION: Amplification primer

<400> SEQUENCE: 101
gttatttgtt tttgagatyg ttgttagag                                             29

<210> SEQ ID NO 102
<211> LENGTH: 26
<212> TYPE: DNA
<213> ORGANISM: Artificial sequence
<220> FEATURE:
<223> OTHER INFORMATION: Amplification primer

<400> SEQUENCE: 102
ctaacaacta ccataacccc accttc                                                26

<210> SEQ ID NO 103
<211> LENGTH: 27
<212> TYPE: DNA
<213> ORGANISM: Artificial sequence
<220> FEATURE:
<223> OTHER INFORMATION: Amplification primer

<400> SEQUENCE: 103
agtggagaaa ggagttagyg gtgggta                                               27

<210> SEQ ID NO 104
<211> LENGTH: 27
<212> TYPE: DNA
<213> ORGANISM: Artificial sequence
<220> FEATURE:
<223> OTHER INFORMATION: Amplification primer

<400> SEQUENCE: 104
cctacctaac atacacrccc tcatccc                                               27

<210> SEQ ID NO 105
<211> LENGTH: 29
<212> TYPE: DNA
<213> ORGANISM: Artificial sequence
<220> FEATURE:
<223> OTHER INFORMATION: Amplification primer

<400> SEQUENCE: 105
ggtttagtta taggtttggt tygtttagg                                             29

<210> SEQ ID NO 106
<211> LENGTH: 27
<212> TYPE: DNA
<213> ORGANISM: Artificial sequence
<220> FEATURE:
<223> OTHER INFORMATION: Amplification primer

<400> SEQUENCE: 106
ctcacccaac aacaacaact tcacctc                                               27

<210> SEQ ID NO 107
<211> LENGTH: 30
<212> TYPE: DNA

<213> ORGANISM: Artificial sequence
<220> FEATURE:
<223> OTHER INFORMATION: Amplification primer

<400> SEQUENCE: 107
gggttatatt ygtttttttt tggtggttta                              30

<210> SEQ ID NO 108
<211> LENGTH: 26
<212> TYPE: DNA
<213> ORGANISM: Artificial sequence
<220> FEATURE:
<223> OTHER INFORMATION: Amplification primer

<400> SEQUENCE: 108
cctcccttcc taccacaaaa accctc                                  26

<210> SEQ ID NO 109
<211> LENGTH: 30
<212> TYPE: DNA
<213> ORGANISM: Artificial sequence
<220> FEATURE:
<223> OTHER INFORMATION: Amplification primer

<400> SEQUENCE: 109
gtttttagag gaaagtttat ttttgtaggg                              30

<210> SEQ ID NO 110
<211> LENGTH: 26
<212> TYPE: DNA
<213> ORGANISM: Artificial sequence
<220> FEATURE:
<223> OTHER INFORMATION: Amplification primer

<400> SEQUENCE: 110
atccccaatc cccaaccctc cttccc                                  26

<210> SEQ ID NO 111
<211> LENGTH: 25
<212> TYPE: DNA
<213> ORGANISM: Artificial sequence
<220> FEATURE:
<223> OTHER INFORMATION: Amplification primer

<400> SEQUENCE: 111
gggtcggagt ttttcggagt tgcgc                                   25

<210> SEQ ID NO 112
<211> LENGTH: 26
<212> TYPE: DNA
<213> ORGANISM: Artificial sequence
<220> FEATURE:
<223> OTHER INFORMATION: Amplification primer

<400> SEQUENCE: 112
ccgctctctt cgctaaatac gactcg                                  26

<210> SEQ ID NO 113
<211> LENGTH: 29
<212> TYPE: DNA
<213> ORGANISM: Artificial sequence
<220> FEATURE:
<223> OTHER INFORMATION: Amplification primer

<400> SEQUENCE: 113
ttttgggttg gagttttttg gagttgtgt                               29

<210> SEQ ID NO 114
<211> LENGTH: 29
<212> TYPE: DNA
<213> ORGANISM: Artificial sequence
<220> FEATURE:
<223> OTHER INFORMATION: Amplification primer

<400> SEQUENCE: 114
aacccactct cttcactaaa tacaactca                                    29

<210> SEQ ID NO 115
<211> LENGTH: 26
<212> TYPE: DNA
<213> ORGANISM: Artificial sequence
<220> FEATURE:
<223> OTHER INFORMATION: Amplification primer

<400> SEQUENCE: 115
aaaataagtt cgggtttcgg cggtac                                       26

<210> SEQ ID NO 116
<211> LENGTH: 27
<212> TYPE: DNA
<213> ORGANISM: Artificial sequence
<220> FEATURE:
<223> OTHER INFORMATION: Amplification primer

<400> SEQUENCE: 116
caataaacga acaaaacgcg aactacg                                      27

<210> SEQ ID NO 117
<211> LENGTH: 28
<212> TYPE: DNA
<213> ORGANISM: Artificial sequence
<220> FEATURE:
<223> OTHER INFORMATION: Amplification primer

<400> SEQUENCE: 117
gtaaaataag tttgggtttt ggtggtat                                     28

<210> SEQ ID NO 118
<211> LENGTH: 29
<212> TYPE: DNA
<213> ORGANISM: Artificial sequence
<220> FEATURE:
<223> OTHER INFORMATION: Amplification primer

<400> SEQUENCE: 118
cacaataaac aaacaaaaca caaactaca                                    29

<210> SEQ ID NO 119
<211> LENGTH: 25
<212> TYPE: DNA
<213> ORGANISM: Artificial sequence
<220> FEATURE:
<223> OTHER INFORMATION: Amplification primer

<400> SEQUENCE: 119
ttagtatttg gtcgcgaggt cgttc                                        25

<210> SEQ ID NO 120
<211> LENGTH: 23
<212> TYPE: DNA
<213> ORGANISM: Artificial sequence
<220> FEATURE:

-continued

```
<223> OTHER INFORMATION: Amplification primer

<400> SEQUENCE: 120
ccctaaatac cgccgctcgc ccg                                              23

<210> SEQ ID NO 121
<211> LENGTH: 28
<212> TYPE: DNA
<213> ORGANISM: Artificial sequence
<220> FEATURE:
<223> OTHER INFORMATION: Amplification primer

<400> SEQUENCE: 121
ttgttagtat ttggttgtga ggttgttt                                         28

<210> SEQ ID NO 122
<211> LENGTH: 24
<212> TYPE: DNA
<213> ORGANISM: Artificial sequence
<220> FEATURE:
<223> OTHER INFORMATION: Amplification primer

<400> SEQUENCE: 122
cccctaaata ccaccactca ccca                                             24

<210> SEQ ID NO 123
<211> LENGTH: 27
<212> TYPE: DNA
<213> ORGANISM: Artificial sequence
<220> FEATURE:
<223> OTHER INFORMATION: Amplification primer

<400> SEQUENCE: 123
gatgatgaca acgacataat ggaaacg                                          27

<210> SEQ ID NO 124
<211> LENGTH: 24
<212> TYPE: DNA
<213> ORGANISM: Artificial sequence
<220> FEATURE:
<223> OTHER INFORMATION: Amplification primer

<400> SEQUENCE: 124
gagtgtgctt ggggaacggg agct                                             24

<210> SEQ ID NO 125
<211> LENGTH: 28
<212> TYPE: DNA
<213> ORGANISM: Artificial sequence
<220> FEATURE:
<223> OTHER INFORMATION: Amplification primer

<400> SEQUENCE: 125
agttgttaag ggagcgtttc gagtttac                                         28

<210> SEQ ID NO 126
<211> LENGTH: 26
<212> TYPE: DNA
<213> ORGANISM: Artificial sequence
<220> FEATURE:
<223> OTHER INFORMATION: Amplification primer

<400> SEQUENCE: 126
ctcaaccttc gaaacgaac ccgccg                                            26
```

```
<210> SEQ ID NO 127
<211> LENGTH: 30
<212> TYPE: DNA
<213> ORGANISM: Artificial sequence
<220> FEATURE:
<223> OTHER INFORMATION: Amplification primer

<400> SEQUENCE: 127
gtagttgtta agggagtgtt ttgagtttat                                       30

<210> SEQ ID NO 128
<211> LENGTH: 28
<212> TYPE: DNA
<213> ORGANISM: Artificial sequence
<220> FEATURE:
<223> OTHER INFORMATION: Amplification primer

<400> SEQUENCE: 128
ctctcaacct tcaaaaacaa acccacca                                         28

<210> SEQ ID NO 129
<211> LENGTH: 27
<212> TYPE: DNA
<213> ORGANISM: Artificial sequence
<220> FEATURE:
<223> OTHER INFORMATION: Amplification primer

<400> SEQUENCE: 129
gggtgatgtt atcgtttttg tatcgac                                          27

<210> SEQ ID NO 130
<211> LENGTH: 25
<212> TYPE: DNA
<213> ORGANISM: Artificial sequence
<220> FEATURE:
<223> OTHER INFORMATION: Amplification primer

<400> SEQUENCE: 130
cctcccctaa cgtaaactcg aaacg                                            25

<210> SEQ ID NO 131
<211> LENGTH: 29
<212> TYPE: DNA
<213> ORGANISM: Artificial sequence
<220> FEATURE:
<223> OTHER INFORMATION: Amplification primer

<400> SEQUENCE: 131
gggggtgatg ttattgtttt tgtattgat                                        29

<210> SEQ ID NO 132
<211> LENGTH: 27
<212> TYPE: DNA
<213> ORGANISM: Artificial sequence
<220> FEATURE:
<223> OTHER INFORMATION: Amplification primer

<400> SEQUENCE: 132
cacctcccct aacataaact caaaaca                                          27

<210> SEQ ID NO 133
<211> LENGTH: 25
<212> TYPE: DNA
<213> ORGANISM: Artificial sequence
<220> FEATURE:
<223> OTHER INFORMATION: Amplification primer
```

-continued

<400> SEQUENCE: 133
ggttgcgttt cgagttgcgg agttc                                    25

<210> SEQ ID NO 134
<211> LENGTH: 26
<212> TYPE: DNA
<213> ORGANISM: Artificial sequence
<220> FEATURE:
<223> OTHER INFORMATION: Amplification primer

<400> SEQUENCE: 134
tccaatcgac aacaaaacga aacgcg                                   26

<210> SEQ ID NO 135
<211> LENGTH: 28
<212> TYPE: DNA
<213> ORGANISM: Artificial sequence
<220> FEATURE:
<223> OTHER INFORMATION: Amplification primer

<400> SEQUENCE: 135
gttggttgtg ttttgagttg tggagttt                                 28

<210> SEQ ID NO 136
<211> LENGTH: 29
<212> TYPE: DNA
<213> ORGANISM: Artificial sequence
<220> FEATURE:
<223> OTHER INFORMATION: Amplification primer

<400> SEQUENCE: 136
aactccaatc aacaacaaaa caaaacaca                                29

<210> SEQ ID NO 137
<211> LENGTH: 26
<212> TYPE: DNA
<213> ORGANISM: Artificial sequence
<220> FEATURE:
<223> OTHER INFORMATION: Amplification primer

<400> SEQUENCE: 137
ggtacaggaa aggcctcttg atgttg                                   26

<210> SEQ ID NO 138
<211> LENGTH: 26
<212> TYPE: DNA
<213> ORGANISM: Artificial sequence
<220> FEATURE:
<223> OTHER INFORMATION: Amplification primer

<400> SEQUENCE: 138
ggatctttta ctaagctgat ctctcc                                   26

<210> SEQ ID NO 139
<211> LENGTH: 26
<212> TYPE: DNA
<213> ORGANISM: Artificial sequence
<220> FEATURE:
<223> OTHER INFORMATION: Amplification primer

<400> SEQUENCE: 139
aagatttggc gttgggcggg acgttc                                   26

<210> SEQ ID NO 140
<211> LENGTH: 25

```
<212> TYPE: DNA
<213> ORGANISM: Artificial sequence
<220> FEATURE:
<223> OTHER INFORMATION: Amplification primer

<400> SEQUENCE: 140
actccaaccc gaacctcgcc gtacg                                   25

<210> SEQ ID NO 141
<211> LENGTH: 28
<212> TYPE: DNA
<213> ORGANISM: Artificial sequence
<220> FEATURE:
<223> OTHER INFORMATION: Amplification primer

<400> SEQUENCE: 141
gtaagatttg gtgttgggtg ggatgttt                                28

<210> SEQ ID NO 142
<211> LENGTH: 28
<212> TYPE: DNA
<213> ORGANISM: Artificial sequence
<220> FEATURE:
<223> OTHER INFORMATION: Amplification primer

<400> SEQUENCE: 142
aaaactccaa cccaaacctc accataca                                28

<210> SEQ ID NO 143
<211> LENGTH: 26
<212> TYPE: DNA
<213> ORGANISM: Artificial sequence
<220> FEATURE:
<223> OTHER INFORMATION: Amplification primer

<400> SEQUENCE: 143
cgttttggag ttggggttag gcggtc                                  26

<210> SEQ ID NO 144
<211> LENGTH: 28
<212> TYPE: DNA
<213> ORGANISM: Artificial sequence
<220> FEATURE:
<223> OTHER INFORMATION: Amplification primer

<400> SEQUENCE: 144
aaataaataa caacctacgc tacgaacg                                28

<210> SEQ ID NO 145
<211> LENGTH: 28
<212> TYPE: DNA
<213> ORGANISM: Artificial sequence
<220> FEATURE:
<223> OTHER INFORMATION: Amplification primer

<400> SEQUENCE: 145
tttgttttgg agttggggtt aggtggtt                                28

<210> SEQ ID NO 146
<211> LENGTH: 30
<212> TYPE: DNA
<213> ORGANISM: Artificial sequence
<220> FEATURE:
<223> OTHER INFORMATION: Amplification primer

<400> SEQUENCE: 146
```

```
ccaaataaat aacaacctac actacaaaca                                        30
```

```
<210> SEQ ID NO 147
<211> LENGTH: 24
<212> TYPE: DNA
<213> ORGANISM: Artificial sequence
<220> FEATURE:
<223> OTHER INFORMATION: Amplification primer

<400> SEQUENCE: 147
tgcgcccagt gtgagatgga gcac                                              24
```

```
<210> SEQ ID NO 148
<211> LENGTH: 25
<212> TYPE: DNA
<213> ORGANISM: Artificial sequence
<220> FEATURE:
<223> OTHER INFORMATION: Amplification primer

<400> SEQUENCE: 148
cccatccctt aggccttgtg ccagt                                             25
```

```
<210> SEQ ID NO 149
<211> LENGTH: 23
<212> TYPE: DNA
<213> ORGANISM: Artificial sequence
<220> FEATURE:
<223> OTHER INFORMATION: Amplification primer

<400> SEQUENCE: 149
taaacagaca tttatttcca gac                                               23
```

```
<210> SEQ ID NO 150
<211> LENGTH: 23
<212> TYPE: DNA
<213> ORGANISM: Artificial sequence
<220> FEATURE:
<223> OTHER INFORMATION: Amplification primer

<400> SEQUENCE: 150
gaaagaaata gtcaatatgc ttg                                               23
```

```
<210> SEQ ID NO 151
<211> LENGTH: 21
<212> TYPE: DNA
<213> ORGANISM: Artificial sequence
<220> FEATURE:
<223> OTHER INFORMATION: Amplification primer

<400> SEQUENCE: 151
agccttcggc tgactggctg g                                                 21
```

```
<210> SEQ ID NO 152
<211> LENGTH: 22
<212> TYPE: DNA
<213> ORGANISM: Artificial sequence
<220> FEATURE:
<223> OTHER INFORMATION: Amplification primer

<400> SEQUENCE: 152
ctgcccatca tcatgacctg ga                                                22
```

```
<210> SEQ ID NO 153
<211> LENGTH: 21
<212> TYPE: DNA
<213> ORGANISM: Artificial sequence
```

```
<220> FEATURE:
<223> OTHER INFORMATION: Amplification primer

<400> SEQUENCE: 153
cagctggagc ctgggggact g                                              21

<210> SEQ ID NO 154
<211> LENGTH: 22
<212> TYPE: DNA
<213> ORGANISM: Artificial sequence
<220> FEATURE:
<223> OTHER INFORMATION: Amplification primer

<400> SEQUENCE: 154
ccttgcgctg ggagagggtg ag                                             22

<210> SEQ ID NO 155
<211> LENGTH: 24
<212> TYPE: DNA
<213> ORGANISM: Artificial sequence
<220> FEATURE:
<223> OTHER INFORMATION: Amplification primer

<400> SEQUENCE: 155
tttctctgct tgtcaaatga gagt                                           24

<210> SEQ ID NO 156
<211> LENGTH: 23
<212> TYPE: DNA
<213> ORGANISM: Artificial sequence
<220> FEATURE:
<223> OTHER INFORMATION: Amplification primer

<400> SEQUENCE: 156
cttaacaaag gaggacctga gag                                            23

<210> SEQ ID NO 157
<211> LENGTH: 27
<212> TYPE: DNA
<213> ORGANISM: Artificial sequence
<220> FEATURE:
<223> OTHER INFORMATION: Amplification primer

<400> SEQUENCE: 157
ttgtagttat cttagaagat agcatgg                                        27

<210> SEQ ID NO 158
<211> LENGTH: 25
<212> TYPE: DNA
<213> ORGANISM: Artificial sequence
<220> FEATURE:
<223> OTHER INFORMATION: Amplification primer

<400> SEQUENCE: 158
acgggaatta ctattaacat aagcg                                          25

<210> SEQ ID NO 159
<211> LENGTH: 23
<212> TYPE: DNA
<213> ORGANISM: Artificial sequence
<220> FEATURE:
<223> OTHER INFORMATION: Amplification primer

<400> SEQUENCE: 159
ctgctgccgc ccctgggcct cac                                            23
```

<210> SEQ ID NO 160
<211> LENGTH: 26
<212> TYPE: DNA
<213> ORGANISM: Artificial Sequence
<220> FEATURE:
<223> OTHER INFORMATION: Amplification primer

<400> SEQUENCE: 160
gtagtgtatt agagcagagc agaatg                                    26

<210> SEQ ID NO 161
<211> LENGTH: 22
<212> TYPE: DNA
<213> ORGANISM: Artificial sequence
<220> FEATURE:
<223> OTHER INFORMATION: Amplification primer

<400> SEQUENCE: 161
cccaggagaa tgcctacctt tg                                        22

<210> SEQ ID NO 162
<211> LENGTH: 23
<212> TYPE: DNA
<213> ORGANISM: Artificial sequence
<220> FEATURE:
<223> OTHER INFORMATION: Amplification primer

<400> SEQUENCE: 162
aaactgccaa acagcccaga agg                                       23

<210> SEQ ID NO 163
<211> LENGTH: 21
<212> TYPE: DNA
<213> ORGANISM: Artificial sequence
<220> FEATURE:
<223> OTHER INFORMATION: Amplification primer

<400> SEQUENCE: 163
ctgtggttga ttgctagtgg t                                         21

<210> SEQ ID NO 164
<211> LENGTH: 23
<212> TYPE: DNA
<213> ORGANISM: Artificial sequence
<220> FEATURE:
<223> OTHER INFORMATION: Amplification primer

<400> SEQUENCE: 164
aagtgactga accttgcagt tct                                       23

<210> SEQ ID NO 165
<211> LENGTH: 24
<212> TYPE: DNA
<213> ORGANISM: Artificial sequence
<220> FEATURE:
<223> OTHER INFORMATION: Amplification primer

<400> SEQUENCE: 165
ccctcctcgg cagtgtgtgg ggtc                                      24

<210> SEQ ID NO 166
<211> LENGTH: 26
<212> TYPE: DNA
<213> ORGANISM: Artificial sequence
<220> FEATURE:
<223> OTHER INFORMATION: Amplification primer

<400> SEQUENCE: 166
gggatgtcag agctggacca gtcgaa 26

<210> SEQ ID NO 167
<211> LENGTH: 24
<212> TYPE: DNA
<213> ORGANISM: Artificial sequence
<220> FEATURE:
<223> OTHER INFORMATION: Amplification primer

<400> SEQUENCE: 167
attactgtgc ttataagtga cacg 24

<210> SEQ ID NO 168
<211> LENGTH: 23
<212> TYPE: DNA
<213> ORGANISM: Artificial sequence
<220> FEATURE:
<223> OTHER INFORMATION: Amplification primer

<400> SEQUENCE: 168
gaagttattg ccaaggaac tgt 23

<210> SEQ ID NO 169
<211> LENGTH: 25
<212> TYPE: DNA
<213> ORGANISM: Artificial sequence
<220> FEATURE:
<223> OTHER INFORMATION: Amplification primer

<400> SEQUENCE: 169
gttcgaggag ggatggtgtt tgagc 25

<210> SEQ ID NO 170
<211> LENGTH: 27
<212> TYPE: DNA
<213> ORGANISM: Artificial sequence
<220> FEATURE:
<223> OTHER INFORMATION: Amplification primer

<400> SEQUENCE: 170
ataccacaca aattcaatac ggattct 27

<210> SEQ ID NO 171
<211> LENGTH: 22
<212> TYPE: DNA
<213> ORGANISM: Artificial sequence
<220> FEATURE:
<223> OTHER INFORMATION: Amplification primer

<400> SEQUENCE: 171
aatgacactc tgaaatccag tc 22

<210> SEQ ID NO 172
<211> LENGTH: 21
<212> TYPE: DNA
<213> ORGANISM: Artificial sequence
<220> FEATURE:
<223> OTHER INFORMATION: Amplification primer

<400> SEQUENCE: 172
ctattgtgtg ataggctctg t 21

<210> SEQ ID NO 173

```
<211> LENGTH: 21
<212> TYPE: DNA
<213> ORGANISM: Artificial sequence
<220> FEATURE:
<223> OTHER INFORMATION: Amplification primer

<400> SEQUENCE: 173
tgagtggtag caaggtttac a                                       21

<210> SEQ ID NO 174
<211> LENGTH: 21
<212> TYPE: DNA
<213> ORGANISM: Artificial sequence
<220> FEATURE:
<223> OTHER INFORMATION: Amplification primer

<400> SEQUENCE: 174
atttcagcct cttccgaatc t                                       21

<210> SEQ ID NO 175
<211> LENGTH: 28
<212> TYPE: DNA
<213> ORGANISM: Artificial sequence
<220> FEATURE:
<223> OTHER INFORMATION: Amplification primer

<400> SEQUENCE: 175
ttaaaaatcg aataatactg aaataacc                                28

<210> SEQ ID NO 176
<211> LENGTH: 22
<212> TYPE: DNA
<213> ORGANISM: Artificial sequence
<220> FEATURE:
<223> OTHER INFORMATION: Amplification primer

<400> SEQUENCE: 176
ggggtgccca gcctaacaat aa                                      22

<210> SEQ ID NO 177
<211> LENGTH: 22
<212> TYPE: DNA
<213> ORGANISM: Artificial sequence
<220> FEATURE:
<223> OTHER INFORMATION: Amplification primer

<400> SEQUENCE: 177
tctctgaaga aggaggtcat gt                                      22

<210> SEQ ID NO 178
<211> LENGTH: 22
<212> TYPE: DNA
<213> ORGANISM: Artificial sequence
<220> FEATURE:
<223> OTHER INFORMATION: Amplification primer

<400> SEQUENCE: 178
ggagggaggt gcattgggta at                                      22

<210> SEQ ID NO 179
<211> LENGTH: 22
<212> TYPE: DNA
<213> ORGANISM: Artificial sequence
<220> FEATURE:
<223> OTHER INFORMATION: Amplification primer

<400> SEQUENCE: 179
```

```
aaagcagttg gtggattcaa ag                                              22

<210> SEQ ID NO 180
<211> LENGTH: 21
<212> TYPE: DNA
<213> ORGANISM: Artificial sequence
<220> FEATURE:
<223> OTHER INFORMATION: Amplification primer

<400> SEQUENCE: 180
ttattagttg gctgggcatg a                                               21

<210> SEQ ID NO 181
<211> LENGTH: 22
<212> TYPE: DNA
<213> ORGANISM: Artificial sequence
<220> FEATURE:
<223> OTHER INFORMATION: Amplification primer

<400> SEQUENCE: 181
ttctttacac atcagtcaca ag                                              22

<210> SEQ ID NO 182
<211> LENGTH: 21
<212> TYPE: DNA
<213> ORGANISM: Artificial sequence
<220> FEATURE:
<223> OTHER INFORMATION: Amplification primer

<400> SEQUENCE: 182
gggtgttgag ttaccagatg a                                               21

<210> SEQ ID NO 183
<211> LENGTH: 24
<212> TYPE: DNA
<213> ORGANISM: Artificial sequence
<220> FEATURE:
<223> OTHER INFORMATION: Amplification primer

<400> SEQUENCE: 183
aaagaaacac atctcagtga aggg                                            24

<210> SEQ ID NO 184
<211> LENGTH: 23
<212> TYPE: DNA
<213> ORGANISM: Artificial sequence
<220> FEATURE:
<223> OTHER INFORMATION: Amplification primer

<400> SEQUENCE: 184
caggaggctt gtagtttaga agg                                             23

<210> SEQ ID NO 185
<211> LENGTH: 20
<212> TYPE: DNA
<213> ORGANISM: Artificial sequence
<220> FEATURE:
<223> OTHER INFORMATION: Amplification primer

<400> SEQUENCE: 185
agttagccac tgctggtgtt                                                 20

<210> SEQ ID NO 186
<211> LENGTH: 20
<212> TYPE: DNA
```

```
<213> ORGANISM: Artificial sequence
<220> FEATURE:
<223> OTHER INFORMATION: Amplification primer

<400> SEQUENCE: 186
ccctccctcc agcacacaaa                                              20

<210> SEQ ID NO 187
<211> LENGTH: 22
<212> TYPE: DNA
<213> ORGANISM: Artificial sequence
<220> FEATURE:
<223> OTHER INFORMATION: Amplification primer

<400> SEQUENCE: 187
ccagagacat ccgttaagga ga                                           22

<210> SEQ ID NO 188
<211> LENGTH: 21
<212> TYPE: DNA
<213> ORGANISM: Artificial sequence
<220> FEATURE:
<223> OTHER INFORMATION: Amplification primer

<400> SEQUENCE: 188
ttgggtctag gagcgtttgc t                                            21

<210> SEQ ID NO 189
<211> LENGTH: 23
<212> TYPE: DNA
<213> ORGANISM: Artificial sequence
<220> FEATURE:
<223> OTHER INFORMATION: Amplification primer

<400> SEQUENCE: 189
tcttgagcat tgtggtggcc tta                                          23

<210> SEQ ID NO 190
<211> LENGTH: 22
<212> TYPE: DNA
<213> ORGANISM: Artificial sequence
<220> FEATURE:
<223> OTHER INFORMATION: Amplification primer

<400> SEQUENCE: 190
ttcgggcttc ctggagggaa ca                                           22

<210> SEQ ID NO 191
<211> LENGTH: 23
<212> TYPE: DNA
<213> ORGANISM: Artificial sequence
<220> FEATURE:
<223> OTHER INFORMATION: Amplification primer

<400> SEQUENCE: 191
gcaacatgaa gattctgaag ggt                                          23

<210> SEQ ID NO 192
<211> LENGTH: 23
<212> TYPE: DNA
<213> ORGANISM: Artificial sequence
<220> FEATURE:
<223> OTHER INFORMATION: Amplification primer

<400> SEQUENCE: 192
acagcaaact gcatttacca tcg                                          23
```

```
<210> SEQ ID NO 193
<211> LENGTH: 21
<212> TYPE: DNA
<213> ORGANISM: Artificial sequence
<220> FEATURE:
<223> OTHER INFORMATION: Amplification primer

<400> SEQUENCE: 193
ttggaaagat cgtcctggtg c                                        21

<210> SEQ ID NO 194
<211> LENGTH: 21
<212> TYPE: DNA
<213> ORGANISM: Artificial sequence
<220> FEATURE:
<223> OTHER INFORMATION: Amplification primer

<400> SEQUENCE: 194
aacttctggc cctcggagga a                                        21

<210> SEQ ID NO 195
<211> LENGTH: 22
<212> TYPE: DNA
<213> ORGANISM: Artificial sequence
<220> FEATURE:
<223> OTHER INFORMATION: Amplification primer

<400> SEQUENCE: 195
aacagcaagc atgacatatt ca                                       22

<210> SEQ ID NO 196
<211> LENGTH: 23
<212> TYPE: DNA
<213> ORGANISM: Artificial sequence
<220> FEATURE:
<223> OTHER INFORMATION: Amplification primer

<400> SEQUENCE: 196
gcagagagaa tgtgaggaac ctt                                      23

<210> SEQ ID NO 197
<211> LENGTH: 21
<212> TYPE: DNA
<213> ORGANISM: Artificial sequence
<220> FEATURE:
<223> OTHER INFORMATION: Amplification primer

<400> SEQUENCE: 197
atgcctcaga gggtagcctt g                                        21

<210> SEQ ID NO 198
<211> LENGTH: 22
<212> TYPE: DNA
<213> ORGANISM: Artificial sequence
<220> FEATURE:
<223> OTHER INFORMATION: Amplification primer

<400> SEQUENCE: 198
attacagaca tcctaagacc cg                                       22

<210> SEQ ID NO 199
<211> LENGTH: 22
<212> TYPE: DNA
<213> ORGANISM: Artificial sequence
<220> FEATURE:
```

<223> OTHER INFORMATION: Amplification primer

<400> SEQUENCE: 199
tcatcaaaca tagctcagtc ct                                              22

<210> SEQ ID NO 200
<211> LENGTH: 21
<212> TYPE: DNA
<213> ORGANISM: Artificial sequence
<220> FEATURE:
<223> OTHER INFORMATION: Amplification primer

<400> SEQUENCE: 200
ccaagggaaa gagaaacgct g                                               21

<210> SEQ ID NO 201
<211> LENGTH: 24
<212> TYPE: DNA
<213> ORGANISM: Artificial sequence
<220> FEATURE:
<223> OTHER INFORMATION: Amplification primer

<400> SEQUENCE: 201
tttctctgga ggacaagcag ttag                                            24

<210> SEQ ID NO 202
<211> LENGTH: 24
<212> TYPE: DNA
<213> ORGANISM: Artificial sequence
<220> FEATURE:
<223> OTHER INFORMATION: Amplification primer

<400> SEQUENCE: 202
tttctctgca tctcttctac ctcc                                            24

<210> SEQ ID NO 203
<211> LENGTH: 18
<212> TYPE: DNA
<213> ORGANISM: Artificial sequence
<220> FEATURE:
<223> OTHER INFORMATION: Amplification primer

<400> SEQUENCE: 203
acctggagct gttcctgc                                                   18

<210> SEQ ID NO 204
<211> LENGTH: 21
<212> TYPE: DNA
<213> ORGANISM: Artificial sequence
<220> FEATURE:
<223> OTHER INFORMATION: Amplification primer

<400> SEQUENCE: 204
gtaacagctc ttcaagctcc t                                               21

<210> SEQ ID NO 205
<211> LENGTH: 21
<212> TYPE: DNA
<213> ORGANISM: Artificial sequence
<220> FEATURE:
<223> OTHER INFORMATION: Amplification primer

<400> SEQUENCE: 205
ggtggttatg gaggatatga c                                               21

```
<210> SEQ ID NO 206
<211> LENGTH: 21
<212> TYPE: DNA
<213> ORGANISM: Artificial sequence
<220> FEATURE:
<223> OTHER INFORMATION: Amplification primer

<400> SEQUENCE: 206
ccagtaagac actactacat c                                              21

<210> SEQ ID NO 207
<211> LENGTH: 23
<212> TYPE: DNA
<213> ORGANISM: Artificial sequence
<220> FEATURE:
<223> OTHER INFORMATION: Amplification primer

<400> SEQUENCE: 207
atttggagat tcacaggaac agc                                            23

<210> SEQ ID NO 208
<211> LENGTH: 23
<212> TYPE: DNA
<213> ORGANISM: Artificial sequence
<220> FEATURE:
<223> OTHER INFORMATION: Amplification primer

<400> SEQUENCE: 208
ccactcttag ctggtaaatg aat                                            23

<210> SEQ ID NO 209
<211> LENGTH: 24
<212> TYPE: DNA
<213> ORGANISM: Artificial sequence
<220> FEATURE:
<223> OTHER INFORMATION: Amplification primer

<400> SEQUENCE: 209
aaccatcttg ctttccttaa attc                                           24

<210> SEQ ID NO 210
<211> LENGTH: 22
<212> TYPE: DNA
<213> ORGANISM: Artificial sequence
<220> FEATURE:
<223> OTHER INFORMATION: Amplification primer

<400> SEQUENCE: 210
cccacccttc ttcacccgct tt                                             22

<210> SEQ ID NO 211
<211> LENGTH: 24
<212> TYPE: DNA
<213> ORGANISM: Artificial sequence
<220> FEATURE:
<223> OTHER INFORMATION: Amplification primer

<400> SEQUENCE: 211
tacaatacca ggatcctcgc acat                                           24

<210> SEQ ID NO 212
<211> LENGTH: 21
<212> TYPE: DNA
<213> ORGANISM: Artificial sequence
<220> FEATURE:
<223> OTHER INFORMATION: Amplification primer
```

```
<400> SEQUENCE: 212
ttggaactgc gagtggctta g                                    21

<210> SEQ ID NO 213
<211> LENGTH: 23
<212> TYPE: DNA
<213> ORGANISM: Artificial sequence
<220> FEATURE:
<223> OTHER INFORMATION: Amplification primer

<400> SEQUENCE: 213
tattattgtt gcatgacatt tgc                                  23

<210> SEQ ID NO 214
<211> LENGTH: 23
<212> TYPE: DNA
<213> ORGANISM: Artificial sequence
<220> FEATURE:
<223> OTHER INFORMATION: Amplification primer

<400> SEQUENCE: 214
aaagtgcacc cacatggatg tta                                  23

<210> SEQ ID NO 215
<211> LENGTH: 22
<212> TYPE: DNA
<213> ORGANISM: Artificial sequence
<220> FEATURE:
<223> OTHER INFORMATION: Amplification primer

<400> SEQUENCE: 215
gctttattgg gattgcaagc gt                                   22

<210> SEQ ID NO 216
<211> LENGTH: 19
<212> TYPE: DNA
<213> ORGANISM: Artificial sequence
<220> FEATURE:
<223> OTHER INFORMATION: Amplification primer

<400> SEQUENCE: 216
gggctgcctg tctgacctc                                       19

<210> SEQ ID NO 217
<211> LENGTH: 22
<212> TYPE: DNA
<213> ORGANISM: Artificial sequence
<220> FEATURE:
<223> OTHER INFORMATION: Amplification primer

<400> SEQUENCE: 217
gggcggacgc atgatagctg ta                                   22

<210> SEQ ID NO 218
<211> LENGTH: 23
<212> TYPE: DNA
<213> ORGANISM: Artificial sequence
<220> FEATURE:
<223> OTHER INFORMATION: Amplification primer

<400> SEQUENCE: 218
gtcttgttct ttgacagaag ctc                                  23

<210> SEQ ID NO 219
<211> LENGTH: 21
```

```
<212> TYPE: DNA
<213> ORGANISM: Artificial sequence
<220> FEATURE:
<223> OTHER INFORMATION: Amplification primer

<400> SEQUENCE: 219
ttcacatagc acacaagtga c                                              21

<210> SEQ ID NO 220
<211> LENGTH: 22
<212> TYPE: DNA
<213> ORGANISM: Artificial sequence
<220> FEATURE:
<223> OTHER INFORMATION: Amplification primer

<400> SEQUENCE: 220
gacctctact tccttggagc tt                                             22

<210> SEQ ID NO 221
<211> LENGTH: 24
<212> TYPE: DNA
<213> ORGANISM: Artificial sequence
<220> FEATURE:
<223> OTHER INFORMATION: Amplification primer

<400> SEQUENCE: 221
cacaagcacg tgcactttat tgaa                                           24

<210> SEQ ID NO 222
<211> LENGTH: 21
<212> TYPE: DNA
<213> ORGANISM: Artificial sequence
<220> FEATURE:
<223> OTHER INFORMATION: Amplification primer

<400> SEQUENCE: 222
tagtagccgc ccatagcctg c                                              21

<210> SEQ ID NO 223
<211> LENGTH: 23
<212> TYPE: DNA
<213> ORGANISM: Artificial sequence
<220> FEATURE:
<223> OTHER INFORMATION: Amplification primer

<400> SEQUENCE: 223
aatgtttctc attaagtcag ggt                                            23

<210> SEQ ID NO 224
<211> LENGTH: 23
<212> TYPE: DNA
<213> ORGANISM: Artificial sequence
<220> FEATURE:
<223> OTHER INFORMATION: Amplification primer

<400> SEQUENCE: 224
ccagccaatg gcgactatag aga                                            23

<210> SEQ ID NO 225
<211> LENGTH: 21
<212> TYPE: DNA
<213> ORGANISM: Artificial sequence
<220> FEATURE:
<223> OTHER INFORMATION: Amplification primer

<400> SEQUENCE: 225
```

```
cccacgttta tttacatatg a                                            21
```

<210> SEQ ID NO 226
<211> LENGTH: 25
<212> TYPE: DNA
<213> ORGANISM: Artificial sequence
<220> FEATURE:
<223> OTHER INFORMATION: Amplification primer

<400> SEQUENCE: 226

```
cttttgtgta tatagata cttgc                                          25
```

<210> SEQ ID NO 227
<211> LENGTH: 21
<212> TYPE: DNA
<213> ORGANISM: Artificial Sequence
<220> FEATURE:
<223> OTHER INFORMATION: Amplification primer

<400> SEQUENCE: 227

```
gcagagtttc actgtatcaa c                                            21
```

<210> SEQ ID NO 228
<211> LENGTH: 21
<212> TYPE: DNA
<213> ORGANISM: Artificial sequence
<220> FEATURE:
<223> OTHER INFORMATION: Amplification primer

<400> SEQUENCE: 228

```
tgaagattgt agggcttaga t                                            21
```

<210> SEQ ID NO 229
<211> LENGTH: 22
<212> TYPE: DNA
<213> ORGANISM: Artificial sequence
<220> FEATURE:
<223> OTHER INFORMATION: Amplification primer

<400> SEQUENCE: 229

```
tatttgtggc tccttcccac tt                                           22
```

<210> SEQ ID NO 230
<211> LENGTH: 22
<212> TYPE: DNA
<213> ORGANISM: Artificial sequence
<220> FEATURE:
<223> OTHER INFORMATION: Amplification primer

<400> SEQUENCE: 230

```
cctcctgccc tcatgcctgt aa                                           22
```

<210> SEQ ID NO 231
<211> LENGTH: 23
<212> TYPE: DNA
<213> ORGANISM: Artificial sequence
<220> FEATURE:
<223> OTHER INFORMATION: Amplification primer

<400> SEQUENCE: 231

```
cgcgttgcat cccttggatt gta                                          23
```

<210> SEQ ID NO 232
<211> LENGTH: 23
<212> TYPE: DNA
<213> ORGANISM: Artificial sequence

```
<220> FEATURE:
<223> OTHER INFORMATION: Amplification primer

<400> SEQUENCE: 232
ccacggttgg ttaatagtcc ctt                                         23

<210> SEQ ID NO 233
<211> LENGTH: 23
<212> TYPE: DNA
<213> ORGANISM: Artificial sequence
<220> FEATURE:
<223> OTHER INFORMATION: Amplification primer

<400> SEQUENCE: 233
aagtacacaa gtggtaagta tag                                         23

<210> SEQ ID NO 234
<211> LENGTH: 22
<212> TYPE: DNA
<213> ORGANISM: Artificial sequence
<220> FEATURE:
<223> OTHER INFORMATION: Amplification primer

<400> SEQUENCE: 234
actctttgat tacaagcact gg                                          22

<210> SEQ ID NO 235
<211> LENGTH: 22
<212> TYPE: DNA
<213> ORGANISM: Artificial sequence
<220> FEATURE:
<223> OTHER INFORMATION: Amplification primer

<400> SEQUENCE: 235
atgcacacat gtttaattgt ag                                          22

<210> SEQ ID NO 236
<211> LENGTH: 20
<212> TYPE: DNA
<213> ORGANISM: Artificial sequence
<220> FEATURE:
<223> OTHER INFORMATION: Amplification primer

<400> SEQUENCE: 236
cgtaggtata cacgtgccat                                             20

<210> SEQ ID NO 237
<211> LENGTH: 23
<212> TYPE: DNA
<213> ORGANISM: Artificial sequence
<220> FEATURE:
<223> OTHER INFORMATION: Amplification primer

<400> SEQUENCE: 237
tgccaagtgc aatgttccag aaa                                         23

<210> SEQ ID NO 238
<211> LENGTH: 22
<212> TYPE: DNA
<213> ORGANISM: Artificial sequence
<220> FEATURE:
<223> OTHER INFORMATION: Amplification primer

<400> SEQUENCE: 238
tttcgggaga acccaaccta ag                                          22
```

<210> SEQ ID NO 239
<211> LENGTH: 21
<212> TYPE: DNA
<213> ORGANISM: Artificial sequence
<220> FEATURE:
<223> OTHER INFORMATION: Amplification primer

<400> SEQUENCE: 239
tgcttaggat atagcatgaa a                                              21

<210> SEQ ID NO 240
<211> LENGTH: 21
<212> TYPE: DNA
<213> ORGANISM: Artificial sequence
<220> FEATURE:
<223> OTHER INFORMATION: Amplification primer

<400> SEQUENCE: 240
tatcggcata gatatatgag t                                              21

<210> SEQ ID NO 241
<211> LENGTH: 22
<212> TYPE: DNA
<213> ORGANISM: Artificial sequence
<220> FEATURE:
<223> OTHER INFORMATION: Amplification primer

<400> SEQUENCE: 241
aaatgctttg gaatccctga ga                                             22

<210> SEQ ID NO 242
<211> LENGTH: 19
<212> TYPE: DNA
<213> ORGANISM: Artificial sequence
<220> FEATURE:
<223> OTHER INFORMATION: Amplification primer

<400> SEQUENCE: 242
tgtgcttaag tggcaggat                                                 19

<210> SEQ ID NO 243
<211> LENGTH: 24
<212> TYPE: DNA
<213> ORGANISM: Artificial sequence
<220> FEATURE:
<223> OTHER INFORMATION: Amplification primer

<400> SEQUENCE: 243
acaagtttaa gaagaacaaa gctg                                           24

<210> SEQ ID NO 244
<211> LENGTH: 24
<212> TYPE: DNA
<213> ORGANISM: Artificial sequence
<220> FEATURE:
<223> OTHER INFORMATION: Amplification primer

<400> SEQUENCE: 244
tatggacatc cagttgttcc agca                                           24

<210> SEQ ID NO 245
<211> LENGTH: 23
<212> TYPE: DNA
<213> ORGANISM: Artificial sequence
<220> FEATURE:
<223> OTHER INFORMATION: Amplification primer -continued

```
<400> SEQUENCE: 245
aggagggaag ggtaacaact cat                                          23

<210> SEQ ID NO 246
<211> LENGTH: 24
<212> TYPE: DNA
<213> ORGANISM: Artificial sequence
<220> FEATURE:
<223> OTHER INFORMATION: Amplification primer

<400> SEQUENCE: 246
agaatgtgga tgaccctcg gaag                                          24

<210> SEQ ID NO 247
<211> LENGTH: 22
<212> TYPE: DNA
<213> ORGANISM: Artificial sequence
<220> FEATURE:
<223> OTHER INFORMATION: Amplification primer

<400> SEQUENCE: 247
gtcagtctgc tcactccacc gt                                           22

<210> SEQ ID NO 248
<211> LENGTH: 22
<212> TYPE: DNA
<213> ORGANISM: Artificial sequence
<220> FEATURE:
<223> OTHER INFORMATION: Amplification primer

<400> SEQUENCE: 248
cggatgtgga aacctttcag ga                                           22

<210> SEQ ID NO 249
<211> LENGTH: 24
<212> TYPE: DNA
<213> ORGANISM: Artificial sequence
<220> FEATURE:
<223> OTHER INFORMATION: Amplification primer

<400> SEQUENCE: 249
tatcacaagc atttattgag tacc                                         24

<210> SEQ ID NO 250
<211> LENGTH: 23
<212> TYPE: DNA
<213> ORGANISM: Artificial sequence
<220> FEATURE:
<223> OTHER INFORMATION: Amplification primer

<400> SEQUENCE: 250
tattctagat atttactcct tcg                                          23

<210> SEQ ID NO 251
<211> LENGTH: 22
<212> TYPE: DNA
<213> ORGANISM: Artificial sequence
<220> FEATURE:
<223> OTHER INFORMATION: Amplification primer

<400> SEQUENCE: 251
acaaaggatg taccatgtcc aa                                           22

<210> SEQ ID NO 252
```

```
<211> LENGTH: 21
<212> TYPE: DNA
<213> ORGANISM: Artificial sequence
<220> FEATURE:
<223> OTHER INFORMATION: Amplification primer

<400> SEQUENCE: 252
cagatcaagg tgatgcacaa g                                              21

<210> SEQ ID NO 253
<211> LENGTH: 23
<212> TYPE: DNA
<213> ORGANISM: Artificial sequence
<220> FEATURE:
<223> OTHER INFORMATION: Amplification primer

<400> SEQUENCE: 253
catacagcaa agtcaactac tgc                                            23

<210> SEQ ID NO 254
<211> LENGTH: 23
<212> TYPE: DNA
<213> ORGANISM: Artificial sequence
<220> FEATURE:
<223> OTHER INFORMATION: Amplification primer

<400> SEQUENCE: 254
acgcagttca aatttcatgg ttt                                            23

<210> SEQ ID NO 255
<211> LENGTH: 21
<212> TYPE: DNA
<213> ORGANISM: Artificial sequence
<220> FEATURE:
<223> OTHER INFORMATION: Amplification primer

<400> SEQUENCE: 255
tttggagaac ctggatggcc t                                              21

<210> SEQ ID NO 256
<211> LENGTH: 21
<212> TYPE: DNA
<213> ORGANISM: Artificial sequence
<220> FEATURE:
<223> OTHER INFORMATION: Amplification primer

<400> SEQUENCE: 256
atctgcagca cccaggatga a                                              21

<210> SEQ ID NO 257
<211> LENGTH: 18
<212> TYPE: DNA
<213> ORGANISM: Artificial sequence
<220> FEATURE:
<223> OTHER INFORMATION: Amplification primer

<400> SEQUENCE: 257
agagcccacg tgggaaga                                                  18

<210> SEQ ID NO 258
<211> LENGTH: 22
<212> TYPE: DNA
<213> ORGANISM: Artificial sequence
<220> FEATURE:
<223> OTHER INFORMATION: Amplification primer

<400> SEQUENCE: 258
```
caggtatcat tcacagtgta at                                    22

<210> SEQ ID NO 259
<211> LENGTH: 22
<212> TYPE: DNA
<213> ORGANISM: Artificial sequence
<220> FEATURE:
<223> OTHER INFORMATION: Amplification primer

<400> SEQUENCE: 259
tgccatgaga tatcttgatt gt                                    22

<210> SEQ ID NO 260
<211> LENGTH: 21
<212> TYPE: DNA
<213> ORGANISM: Artificial sequence
<220> FEATURE:
<223> OTHER INFORMATION: Amplification primer

<400> SEQUENCE: 260
gggccaatgg agaaatgcag c                                     21

<210> SEQ ID NO 261
<211> LENGTH: 22
<212> TYPE: DNA
<213> ORGANISM: Artificial sequence
<220> FEATURE:
<223> OTHER INFORMATION: Amplification primer

<400> SEQUENCE: 261
tatacagtct tcccacttca ct                                    22

<210> SEQ ID NO 262
<211> LENGTH: 23
<212> TYPE: DNA
<213> ORGANISM: Artificial sequence
<220> FEATURE:
<223> OTHER INFORMATION: Amplification primer

<400> SEQUENCE: 262
ttctgcctga tcatcccatt gta                                   23

<210> SEQ ID NO 263
<211> LENGTH: 22
<212> TYPE: DNA
<213> ORGANISM: Artificial sequence
<220> FEATURE:
<223> OTHER INFORMATION: Amplification primer

<400> SEQUENCE: 263
aagctacgag aatgagcagg tg                                    22

<210> SEQ ID NO 264
<211> LENGTH: 21
<212> TYPE: DNA
<213> ORGANISM: Artificial sequence
<220> FEATURE:
<223> OTHER INFORMATION: Amplification primer

<400> SEQUENCE: 264
gtcttgttct gtgatgaggg g                                     21

<210> SEQ ID NO 265
<211> LENGTH: 22
<212> TYPE: DNA

```
<213> ORGANISM: Artificial sequence
<220> FEATURE:
<223> OTHER INFORMATION: Amplification primer

<400> SEQUENCE: 265
gaagatcagt taatgtcact cc                                              22

<210> SEQ ID NO 266
<211> LENGTH: 22
<212> TYPE: DNA
<213> ORGANISM: Artificial sequence
<220> FEATURE:
<223> OTHER INFORMATION: Amplification primer

<400> SEQUENCE: 266
tggtagaaga caagatgatt tg                                              22

<210> SEQ ID NO 267
<211> LENGTH: 23
<212> TYPE: DNA
<213> ORGANISM: Artificial sequence
<220> FEATURE:
<223> OTHER INFORMATION: Amplification primer

<400> SEQUENCE: 267
tgaatgacaa agacataaca tcc                                             23

<210> SEQ ID NO 268
<211> LENGTH: 23
<212> TYPE: DNA
<213> ORGANISM: Artificial sequence
<220> FEATURE:
<223> OTHER INFORMATION: Amplification primer

<400> SEQUENCE: 268
ctcaagttat gtgtccctat att                                             23

<210> SEQ ID NO 269
<211> LENGTH: 22
<212> TYPE: DNA
<213> ORGANISM: Artificial sequence
<220> FEATURE:
<223> OTHER INFORMATION: Amplification primer

<400> SEQUENCE: 269
ttccgctgca ttgctggcat gt                                              22

<210> SEQ ID NO 270
<211> LENGTH: 22
<212> TYPE: DNA
<213> ORGANISM: Artificial sequence
<220> FEATURE:
<223> OTHER INFORMATION: Amplification primer

<400> SEQUENCE: 270
gccttggaag tgcctaattg ct                                              22

<210> SEQ ID NO 271
<211> LENGTH: 21
<212> TYPE: DNA
<213> ORGANISM: Artificial sequence
<220> FEATURE:
<223> OTHER INFORMATION: Amplification primer

<400> SEQUENCE: 271
agtcccagac ctcaaggatc t                                               21
```

<210> SEQ ID NO 272
<211> LENGTH: 21
<212> TYPE: DNA
<213> ORGANISM: Artificial sequence
<220> FEATURE:
<223> OTHER INFORMATION: Amplification primer

<400> SEQUENCE: 272
gggtaaatca gtcagacagg c                                              21

<210> SEQ ID NO 273
<211> LENGTH: 20
<212> TYPE: DNA
<213> ORGANISM: Artificial sequence
<220> FEATURE:
<223> OTHER INFORMATION: Amplification primer

<400> SEQUENCE: 273
cagctcagtc acaggagaga                                                20

<210> SEQ ID NO 274
<211> LENGTH: 21
<212> TYPE: DNA
<213> ORGANISM: Artificial sequence
<220> FEATURE:
<223> OTHER INFORMATION: Amplification primer

<400> SEQUENCE: 274
tacagttcgc atcctcttaa c                                              21

<210> SEQ ID NO 275
<211> LENGTH: 21
<212> TYPE: DNA
<213> ORGANISM: Artificial sequence
<220> FEATURE:
<223> OTHER INFORMATION: Amplification primer

<400> SEQUENCE: 275
ctcacaggct tcaacaaggc a                                              21

<210> SEQ ID NO 276
<211> LENGTH: 21
<212> TYPE: DNA
<213> ORGANISM: Artificial sequence
<220> FEATURE:
<223> OTHER INFORMATION: Amplification primer

<400> SEQUENCE: 276
gggaggtgcc tttattgccc a                                              21

<210> SEQ ID NO 277
<211> LENGTH: 23
<212> TYPE: DNA
<213> ORGANISM: Artificial sequence
<220> FEATURE:
<223> OTHER INFORMATION: Amplification primer

<400> SEQUENCE: 277
tagcatataa ttggaaaggg ttc                                            23

<210> SEQ ID NO 278
<211> LENGTH: 23
<212> TYPE: DNA
<213> ORGANISM: Artificial sequence
<220> FEATURE:

<223> OTHER INFORMATION: Amplification primer

<400> SEQUENCE: 278
aagtgttaca gagccatgga caa                                              23

<210> SEQ ID NO 279
<211> LENGTH: 23
<212> TYPE: DNA
<213> ORGANISM: Artificial sequence
<220> FEATURE:
<223> OTHER INFORMATION: Amplification primer

<400> SEQUENCE: 279
ctttgacaca ttacagatct ggg                                              23

<210> SEQ ID NO 280
<211> LENGTH: 23
<212> TYPE: DNA
<213> ORGANISM: Artificial sequence
<220> FEATURE:
<223> OTHER INFORMATION: Amplification primer

<400> SEQUENCE: 280
catccttgca ttccttgctt gtt                                              23

<210> SEQ ID NO 281
<211> LENGTH: 27
<212> TYPE: DNA
<213> ORGANISM: Artificial sequence
<220> FEATURE:
<223> OTHER INFORMATION: Amplification primer

<400> SEQUENCE: 281
ttaaccaacg taaccatatt gaataaa                                          27

<210> SEQ ID NO 282
<211> LENGTH: 24
<212> TYPE: DNA
<213> ORGANISM: Artificial sequence
<220> FEATURE:
<223> OTHER INFORMATION: Amplification primer

<400> SEQUENCE: 282
aggatgataa actggtggtg gaat                                             24

<210> SEQ ID NO 283
<211> LENGTH: 23
<212> TYPE: DNA
<213> ORGANISM: Artificial sequence
<220> FEATURE:
<223> OTHER INFORMATION: Amplification primer

<400> SEQUENCE: 283
gcacattaaa cagcatacat acc                                              23

<210> SEQ ID NO 284
<211> LENGTH: 23
<212> TYPE: DNA
<213> ORGANISM: Artificial sequence
<220> FEATURE:
<223> OTHER INFORMATION: Amplification primer

<400> SEQUENCE: 284
ccctgttcct tgtggaaacc tat                                              23

```
<210> SEQ ID NO 285
<211> LENGTH: 23
<212> TYPE: DNA
<213> ORGANISM: Artificial sequence
<220> FEATURE:
<223> OTHER INFORMATION: Amplification primer

<400> SEQUENCE: 285
ttgcccataa ctcactgtgg cct                                         23

<210> SEQ ID NO 286
<211> LENGTH: 21
<212> TYPE: DNA
<213> ORGANISM: Artificial sequence
<220> FEATURE:
<223> OTHER INFORMATION: Amplification primer

<400> SEQUENCE: 286
aaatctggct ggaacgggac a                                           21

<210> SEQ ID NO 287
<211> LENGTH: 23
<212> TYPE: DNA
<213> ORGANISM: Artificial sequence
<220> FEATURE:
<223> OTHER INFORMATION: Amplification primer

<400> SEQUENCE: 287
tgtctttagg agacgtgaga aag                                         23

<210> SEQ ID NO 288
<211> LENGTH: 22
<212> TYPE: DNA
<213> ORGANISM: Artificial sequence
<220> FEATURE:
<223> OTHER INFORMATION: Amplification primer

<400> SEQUENCE: 288
cttccacgga ttactgacag ag                                          22

<210> SEQ ID NO 289
<211> LENGTH: 23
<212> TYPE: DNA
<213> ORGANISM: Artificial sequence
<220> FEATURE:
<223> OTHER INFORMATION: Amplification primer

<400> SEQUENCE: 289
aacttagcac aattaactgc agc                                         23

<210> SEQ ID NO 290
<211> LENGTH: 22
<212> TYPE: DNA
<213> ORGANISM: Artificial sequence
<220> FEATURE:
<223> OTHER INFORMATION: Amplification primer

<400> SEQUENCE: 290
tgcctgaaat cccactactt gg                                          22
```

```
<210> SEQ ID NO 291
<211> LENGTH: 23
<212> TYPE: DNA
<213> ORGANISM: Artificial sequence
<220> FEATURE:
<223> OTHER INFORMATION: Amplification primer

<400> SEQUENCE: 291
catttatctt gatcaaaccc acc                                              23

<210> SEQ ID NO 292
<211> LENGTH: 22
<212> TYPE: DNA
<213> ORGANISM: Artificial sequence
<220> FEATURE:
<223> OTHER INFORMATION: Amplification primer

<400> SEQUENCE: 292
atgctttctg aagagtgagc cc                                               22

<210> SEQ ID NO 293
<211> LENGTH: 22
<212> TYPE: DNA
<213> ORGANISM: Artificial sequence
<220> FEATURE:
<223> OTHER INFORMATION: Amplification primer

<400> SEQUENCE: 293
cgtggtacct aaacatggac ac                                               22

<210> SEQ ID NO 294
<211> LENGTH: 22
<212> TYPE: DNA
<213> ORGANISM: Artificial sequence
<220> FEATURE:
<223> OTHER INFORMATION: Amplification primer

<400> SEQUENCE: 294
tctcattgta ggtctcctaa ag                                               22

<210> SEQ ID NO 295
<211> LENGTH: 22
<212> TYPE: DNA
<213> ORGANISM: Artificial sequence
<220> FEATURE:
<223> OTHER INFORMATION: Amplification primer

<400> SEQUENCE: 295
tttgaagcac taagatcaat ac                                               22

<210> SEQ ID NO 296
<211> LENGTH: 18
<212> TYPE: DNA
<213> ORGANISM: Artificial sequence
<220> FEATURE:
<223> OTHER INFORMATION: Amplification primer

<400> SEQUENCE: 296
ttgcgaacgc gtctgtga                                                    18
```

GENOMIC SCREEN FOR EPIGENETICALLY SILENCED GENES ASSOCIATED WITH CANCER

This application claims the benefit of priority under 35 U.S.C. §119(e)(1) of U.S. Ser. No. 60/362,422, filed Mar. 7, 2002, the entire content of which is incorporated herein by reference.

This invention was made in part with government support under Grant No. CA54396 awarded by the National Cancer Institute. The United States government may have certain rights in this invention.

BACKGROUND OF THE INVENTION

1. Field of the Invention

The invention relates generally to methods of detecting genes that are epigenetically silenced in cancer cells, and more specifically to a genomic screen useful for identifying colorectal cancer cells and gastric cancer cells.

2. Background Information

Although cancers generally are considered to be due to genetic changes such as mutations of a gene, it has become clear that epigenetic mechanisms, which do not result in mutations of the DNA sequence, also can result in cancers. The most commonly observed epigenetic change involves silencing of gene expression due to methylation of the gene sequence, particularly the 5' upstream gene regulatory sequences. Methylation of cytosine residues located 5' to guanosine in CpG dinucleotides, particularly in CpG-rich regions (CpG islands), often is involved in the normal regulation of gene expression in higher eukaryotes. For example, extensive methylation of CpG islands is associated with transcriptional inactivation of selected imprinted genes, as well as the genes on the inactivated X chromosome in females. Aberrant methylation of normally unmethylated CpG islands also has been found in immortalized and transformed cells, and has been associated with transcriptional inactivation of defined tumor suppressor genes in human cancers.

Changes to genes that are associated with cancer, including mutations that result in loss of expression of gene or expression of a defective gene product, and epigenetic mechanisms such as methylation-silencing of gene transcription, provide markers useful for determining whether a cell is susceptible to loss of normal growth control and, therefore, potentially a cancer cell. For example, a mutation of the BRCA1 gene has been associated with breast cancer. As such, diagnostic tests can be performed using cells, for example, from a woman with a family history of breast cancer to determine whether the woman has the BRCA1 mutation that is a marker for breast cancer. The prostate specific antigen (PSA) is another example of a marker, in this case for prostate cancer. Although neither the defect resulting in expression of the PSA nor the normal function of PSA in the body is known, PSA nevertheless provides a valuable cancer marker because it allows the identification of men predisposed to prostate cancer or at a very early stage of the disease such that effective therapy can be implemented. More recently, methylation-silenced transcription of a suppressor of cytokine signaling/cytokine-inducible SH2 protein family member, the SOCS-1 gene was found in various cancers, including hepatocellular carcinoma, multiple myeloma, and acute leukemias. As such, screening assays directed to detecting the methylation status of the SOCS-1 gene can provide diagnostic information relating to such cancer.

As cancer often is a silent disease that does not present clinical signs or symptoms until the disease is well advanced, the availability and use of markers that allow the identification of individuals susceptible to a cancer, or even that allow detection of a cancer at an early stage, can be of great benefit. Unfortunately, such markers are not available for most cancers. As such, many cancer patients do not seek medical assistance until the cancer is at a stage that requires radical therapy, or is untreatable. Thus, a need exists for markers that can be used to detect cancer cells. The present invention satisfies this need and provides additional advantages.

SUMMARY OF THE INVENTION

The present invention relates to methods of identifying epigenetically silenced genes, for example, methylation silenced genes, that are associated with a cancer. In one embodiment, the present invention relates to a method of identifying at least one epigenetically silenced gene associated with at least one cancer. Such a method can be performed, for example, by contacting an array of nucleotide sequences representative of a genome with nucleic acid subtraction products, which comprise nucleic acid molecules corresponding to RNA expressed in cancer cells contacted with at least one agent that reactivates expression of epigenetically silenced genes but not RNA expressed in normal cells corresponding to the cancer cells, under conditions suitable for selective hybridization of nucleic acid subtraction products to complementary nucleotide sequences of the array; and detecting selective hybridization of nucleic acid subtraction products to a subpopulation of nucleotide sequences of the array, wherein nucleic acid molecules corresponding to RNA expressed in the normal cells corresponding the cancer cells do not hybridize to the subpopulation of nucleotide sequences under such conditions suitable for selective hybridization, whereby the nucleic acid subtraction products that selectively hybridize to the subpopulation of nucleotide sequences of the array represent epigenetically silenced genes of the cancer cells, thereby identifying at least one epigenetically silenced genes associated with at least one cancer.

The agent that reactivates expression of epigenetically silenced genes can be any such agent, for example, a methyltransferase inhibitor (e.g., 5-aza-2'-deoxycytidine; DAC), a histone deacetylase inhibitor (e.g., trichostatin A; TSA), or a combination of agents such as a combination of DAC and TSA. Accordingly, in one aspect of the present embodiment, the nucleic acid subtraction products include nucleic acid molecules corresponding to RNA expressed in cancer cells contacted with DAC or with TSA. In another aspect, the nucleic acid subtraction products include nucleic acid molecules corresponding to RNA expressed in cancer cells contacted with DAC and TSA.

Epigenetically silenced genes associated with a cancer are exemplified herein by the genes listed in Table 1. For example, epigenetically silenced genes that can be reactivated due to contact of cancer cells with DAC, i.e., methylation silenced genes, are exemplified by PTGS2, CDKN2A, TIMP3, S100A10, SFRP1, SFRP2, SFRP4, SFRP5, CXX1, SEZZ6L, KIAA0786, TIMP2, PCDH8, FOLH1, SNRPN, HOXA1, GRO3, DLX7. Similarly, epigenetically silenced genes that can be reactivated due to contact of cancer cells with DAC and TSA are exemplified by POR1, MBNL, TRADD, PDIP, RAD23B, RPL13, GNAI2, PPP1R21A, FPGT, TRIM32, or a combination thereof.

A method of the invention can identify epigenetically silenced genes associated with one or more cancers, including, for example, one or more carcinomas and/or sarcomas. Such a method is exemplified herein by identifying epigenetically silenced genes associated with a colorectal cancer, with a gastric cancer, and with a colorectal cancer and a gastric cancer.

In another embodiment, the present invention relates to a method of identifying at least one methylation silenced gene associated with at least one cancer. Such a method can be performed, for example, by contacting an array of nucleotide sequences representative of a genome with nucleic acid subtraction products, which comprise nucleic acid molecules corresponding to RNA expressed in cancer cells contacted with a demethylating agent but not nucleic acid molecules corresponding to RNA expressed in normal cells corresponding to the cancer cells, under conditions suitable for selective hybridization of nucleic acid subtraction products to complementary nucleotide sequences of the array; and detecting selective hybridization of nucleic acid subtraction products to a subpopulation of nucleotide sequences of the array, wherein nucleic acid molecules corresponding to RNA expressed in the normal cells corresponding the cancer cells do not hybridize to the subpopulation of nucleotide sequences under said conditions suitable for selective hybridization, whereby the nucleic acid subtraction products that selectively hybridize to the subpopulation of nucleotide sequences of the array represent methylation silenced genes of the cancer cells, thereby identifying at least one methylation silenced genes associated with at least one cancer.

The nucleic acid molecules corresponding to RNA of a cancer cell can be DNA (e.g., cDNA) or RNA (e.g., cRNA). Generally, the nucleic acid molecules corresponding to RNA of a cell are detectably labeled, for example, with a radioisotope, a paramagnetic isotope, a luminescent compound, a chemiluminescent compound, a fluorescent compound, a metal chelate, an enzyme, a substrate for an enzyme, a receptor, or a ligand for a receptor; or are capable of being detected, for example, using a detectably labeled probe, such that hybridization of the nucleic acid molecules to nucleotide sequences of the array can be detected.

According to a method of the invention, at least one (e.g., 1, 2, 3, 4, 5, or more) methylation silenced gene can be associated with at least one (e.g. 1, 2, 3, or more) cancer. The cancer can be, for example, a carcinoma or a sarcoma, including one or more specific types of cancer, e.g., an alimentary/gastrointestinal tract cancer, a liver cancer, a skin cancer, a breast cancer, an ovarian cancer, a prostate cancer, a lymphoma, a leukemia, a kidney cancer, a lung cancer, a muscle cancer, a bone cancer, or a brain cancer. In one example, methylation silenced PTGS2, CDKN2A, TIMP3, S100A10, SFRP1, CXX1, SEZZ6L, KIAA0786, TIMP2, PCDH8, FOLH1, SNRPN, HOXA1, GRO3, and DLX7 genes, alone or in combination, were identified as being associated with colorectal cancer, gastric cancer, or both colorectal cancer and gastric cancer. In another example, members of a family of genes, including SFRP1, SFRP2, SFRP4, SFRP5, alone or in combination, were identified as methylation silenced genes associated with colorectal cancer and/or gastric cancer.

The present invention also relates to a method for identifying a cell that exhibits or is predisposed to exhibiting unregulated growth. Such a method can be performed, for example, by detecting, in a test cell, epigenetic silencing of at least one gene as set forth in Table 1, or a combination thereof, thereby identifying the test cell as a cell that exhibits or is predisposed to exhibiting unregulated growth. For example, the epigenetic silenced gene can be a PTGS2, CDKN2A, TIMP3, S100A10, SFRP1, SFRP2, SFRP4, SFRP5, CXX1, SEZZ6L, KIAA0786, TIMP2, PCDH8, FOLH1, SNRPN, HOXA1, GRO3, DLX7, POR1, MBNL, TRADD, PDIP, RAD23B, RPL13, GNAI2, PPP1R21A, FPGT, or TRIM32 gene, or a combination of such genes. The cell exhibiting, or predisposed to exhibiting unregulated growth, can be a neoplastic cell, which can be, for example, a premalignant cell such as a cell of a gastrointestinal polyp, or can be a cancer cell, for example, a carcinoma cell such as a colorectal cancer cell or a gastric cancer cell, or a sarcoma cell.

In one embodiment, the epigenetic silencing is methylation silencing, and the method for identifying a cell that exhibits or is predisposed to exhibiting unregulated growth is performed by detecting methylation silencing. Methylation silencing can be detected, for example, by contacting a region comprising a 5' regulatory region of the nucleic acid molecule comprising the gene with a methylation sensitive restriction endonuclease, which cleaves a recognition site in the 5' regulatory region comprising a methylated cytosine residue of a CpG dinucleotide, whereby cleavage of the nucleic acid molecule is indicative of methylation silencing of the gene of the test cell. For example, the methylation sensitive restriction endonuclease is Acc III, Ban I, BstN I, Msp I, or Xma I. Alternatively, or in addition, methylation silencing can be detected by contacting a region comprising a 5' regulatory region of the nucleic acid molecule comprising the gene with a methylation sensitive restriction endonuclease, which cleaves a recognition site in the 5' regulatory region comprising a methylated cytosine residue of a CpG dinucleotide, provided the cytosine residue of the CpG dinucleotide is unmethylated, whereby a lack of cleavage of the nucleic acid molecule is indicative of methylation silencing of the gene of the test cell. For example, the methylation sensitive restriction endonuclease is Acc II, Ava I, BssH II, BstU I, Hpa II, or Not I.

Methylation silencing of a gene also can be detected by contacting a 5' regulatory region of the nucleic acid molecule comprising the gene of the test cell with a chemical reagent that selectively modifies either an unmethylated cytosine residue or a methylated cytosine residue, and detecting a product generated due to said contacting, wherein the product is indicative of methylation of a cytosine residue in a CpG dinucleotide of the gene, thereby detecting methylation silencing of the gene of the test cell. For example, the product can be detected using an electrophoresis method, a chromatography method, a mass spectrometry method, or a combination of such methods.

In one aspect of the present method, the chemical reagent is hydrazine, thereby producing a hydrazine treated 5' regulatory region of the gene. Such a method can further include contacting the hydrazine treated 5' regulatory region with a reagent that cleaves hydrazine modified cytosine residues to generate a product comprising fragments of the nucleic acid molecule comprising the gene; separating the fragments according to molecular weight; and detecting a gap at a position known to contain a cytosine residue in the 5' regulatory region of the gene, wherein the gap is indicative of methylation of a cytosine residue in the CpG dinucleotide in the gene, thereby detecting methylation silencing of the gene of the test cell. The reagent that cleaves the hydrazine modified cytosine residue can be, for example, piperidine.

In another aspect of the present method, the chemical reagent comprises bisulfite ions, whereby unmethylated cytosine residues in the 5' regulatory region of the gene are converted to bisulfite modified cytosine residues. Such a method can further include exposing the bisulfite ion treated gene to alkaline conditions, whereby bisulfite modified cytosine residues are converted to uracil residues; and detecting an amount or distribution of uracil residues in the 5' regulatory region of the bisulfite ion treated gene of the test cell, wherein a decrease in the amount or distribution of uracil residues in the 5' regulatory region of gene from the test cell, as compared to the amount or distribution of uracil residues in a corresponding bisulfite ion treated unmethylated gene following exposure to alkaline conditions, is indicative of methylation of cytosine residues in CpG dinucleotides in the 5' regulatory region of the gene, thereby detecting methylation silencing of the gene of the test cell. The amount or distribution of uracil residues can be detected, for example, by determining the nucleotide sequence of the bisulfite modified 5' regulatory region of the gene following exposure to alkaline conditions. Alternatively, or in addition, the amount or distribution of uracil residues can be detected by contacting the bisulfite ion treated gene sequence, following exposure to alkaline conditions, with an oligonucleotide that selectively hybridizes to the 5' region regulatory of the gene containing uracil residues, and detecting selective hybridization of the oligonucleotide.

An oligonucleotide useful in such a method can be, for example, an oligonucleotide having a nucleotide sequence as set forth in SEQ ID NO: 23, 24, 111, 112, 115, 116, 119, 120, 125, 126, 129, 130, 133, 134, 139, 140, 143, or 144. To facilitate detection, in one aspect the oligonucleotide can include a detectable label, thus providing a means to detect selective hybridization by detecting the label. The detectable label can be any label that is conveniently detectable, including, for example, is a radioisotope, a paramagnetic isotope, a luminescent compound, a chemiluminescent compound, a fluorescent compound, a metal chelate, an enzyme, a substrate for an enzyme, a receptor, or a ligand for a receptor. In another aspect, the oligonucleotide can be a substrate for a primer extension reaction, wherein detecting selective hybridization comprises detecting a product of the primer extension reaction. For example, the oligonucleotide (primer) can be a methylation specific primer such as an oligonucleotide having a nucleotide sequence as set forth in SEQ ID NO: 23, 24, 111, 112, 115, 116, 119, 120, 125, 126, 129, 130, 133, 134, 139, 140, 143, or 144, which can selectively hybridize to and allow extension of nucleotide sequence comprising a methylated region of an SFRP1, SFRP2, SFRP4, or SFRP5 gene.

An amount or distribution of uracil residues also can be detected, for example, by contacting the 5' regulatory region of a gene with an amplification primer pair comprising a forward primer and a reverse primer under conditions suitable for amplification, wherein at least one primer of the primer pair comprises an oligonucleotide that selectively hybridizes to a nucleotide sequence of the 5' regulatory region containing uracil residues, whereby generation of an amplification product is indicative of methylation of cytosine residues in CpG dinucleotides in the 5' regulatory region of the gene, thereby detecting methylation silencing of the gene of the test cell. Amplification primer pairs useful for such a method are exemplified in Tables 2 and 3, and include, for example, a primer pair as set forth in SEQ ID NO: 23 and 24, SEQ ID NOS: 111 and 112, SEQ ID NOS: 115 and 116, SEQ ID NOS: 119 and 120, SEQ ID NOS: 125 and 126, SEQ ID NOS: 129 and 130, SEQ ID NOS: 133 and 134, SEQ ID NOS: 139 and 140, or SEQ ID NOS: 143 and 144, which are methylation specific primers useful for detecting methylation of an SFRP1, SFRP2, SFRP4, or SFRP5 gene 5' regulatory region.

In addition, the amount or distribution of uracil residues can be detected by contacting the 5' regulatory region of the gene with an amplification primer pair comprising a forward primer and a reverse primer under conditions suitable for amplification, wherein both primers of the primer pair selectively hybridize to a nucleotide sequence of the 5' regulatory region containing cytosine residues, but not to a corresponding nucleotide sequence of the 5' regulatory region containing uracil residues, and whereby generation of an amplification product is indicative of a lack of methylation of cytosine residues in CpG dinucleotides in the 5' regulatory region of the gene, thereby detecting methylation silencing of the gene of the test cell. Amplification primer pair useful for such a method are exemplified in Tables 2 and 3, and include, for example, a primer pair as set forth in SEQ ID NOS: 25 and 26, SEQ ID NOS: 113 and 114, SEQ ID NOS: 117 and 118, SEQ ID NOS: 121 and 122, SEQ ID NOS: 127 and 128, SEQ ID NOS: 131 and 132, SEQ ID NOS: 135 and 136, SEQ ID NOS: 141 and 142, or SEQ ID NOS: 145 and 146, which are unmethylation specific primers useful for detecting a lack of methylation of an SFRP1, SFRP2, SFRP4, or SFRP5 gene 5' regulatory region.

The amount or distribution of uracil residues also can be detected by contacting the 5' regulatory region of the gene with a first amplification primer pair and a second amplification primer pair under conditions suitable for amplification, wherein the first amplification primer pair comprises a forward primer and a reverse primer, wherein at least one primer of the first primer pair comprises an oligonucleotide that selectively hybridizes to a nucleotide sequence of the 5' regulatory region of the gene containing uracil residues, and wherein the second amplification primer pair comprises a forward primer and a reverse primer, wherein both primers of the second primer pair selectively hybridize to a nucleotide sequence of the 5' regulatory region of the gene containing cytosine residues, but not to a corresponding nucleotide sequence of the 5' regulatory region of the gene containing uracil residues, and wherein an amplification product, if any, generated by the first primer pair has a first length, and wherein an amplification product, if any, generated by the second primer pair has a second length, which is different from the first length, whereby the length of the amplification products is indicative of uracil residues and, therefore, methylation of cytosine residues in CpG dinucleotides in the 5' regulatory region of the gene, thereby detecting methylation silencing of the gene of the test cell.

Methylation silencing of a gene associated with a cancer also can be identified by contacting a test cell with a demethylating agent, and detecting increased expression of an RNA encoded by the gene as compared to a level of expression of the RNA in a test cell not contacted with a demethylating agent. Such a method can further include detecting methylation, if any, of cytosine residues in a CpG dinucleotide in a CpG island of the 5' regulatory region of the gene in a corresponding cell exhibiting regulated growth, or an extract of the corresponding cell The demethylating agent can be a methyltransferase inhibitor such as 5-aza-2'-deoxycytidine. Increased expression of an RNA can be detected using any method for detecting RNA, including, for example, northern blot analysis, a reverse transcription-polymerase chain reaction assay, or selective hybridization to an array of nucleotide sequences as disclosed herein. Accordingly, the methods of the invention can be performed in a high throughput format, wherein the test cell, or extract of the test cell, comprises one of a plurality of test cells, or extracts of the test cells, or a combination thereof, and each of the test cells, or extracts of the test cells, of the plurality is the same or different, or a combination thereof. According to a high throughput method of practicing the present invention, the test cells, or extracts of the test cell, can be arranged in an array, which can be an addressable array, on a solid support such as a microchip, a glass slide, or a bead.

A test cell examined according to a method of the invention can be a cell from a cell culture, e.g., an established cell line, or primary cells placed in culture, or can comprise a sample obtained from a subject, for example, a human subject. As such, the sample can be an organ sample, a tissue sample, or a cell sample, for example, an alimentary/gastrointestinal tract tissue sample, a liver sample, a skin sample, a lymph node sample, a kidney sample, a lung sample, a muscle sample, a bone sample, or a brain sample. For example, a gastrointestinal tract sample can include a stomach sample, a small intestine sample, a colon sample, a rectal sample, or a combination thereof. A sample also can comprise a biological fluid sample, for example, a bone marrow, blood, serum, lymph, cerebrospinal fluid, saliva, sputum, stool, urine, or ejaculate sample, which can contain cells therein or products of cells, particularly nucleic acid molecules.

The present invention also relates to a method of reducing or inhibiting unregulated growth of a cell exhibiting epigenetic silenced transcription of at least one gene associated with a cancer. Such a method can be practiced, for example, by restoring expression of a polypeptide encoded by the epigenetic silenced gene in the cell, thereby reducing or inhibiting unregulated growth of the cell. Such expression can be restored, for example, by contacting the cell with a demethylating agent (e.g, a methyltransferase inhibitor), a histone deacetylase inhibitor, or a combination thereof.

In one embodiment, the epigenetic silenced gene is a methylation silenced gene, and the method includes contacting the cell with at least one demethylating agent, for example, DAC. In one aspect, the cell can be contacted with the demethylating agent in vitro, e.g., in a culture medium or other medium conducive to survival of the cell. If desired, the cell contacted with the demethylating agent further can be administered to a subject. In another aspect, the agent can be administered to subject such that the cell exhibiting unregulated growth is contacted with the agent.

In another embodiment, the method includes introducing a polynucleotide encoding the polypeptide into the cell, whereby the polypeptide is expressed from the polynucleotide, thereby restoring expression of the polypeptide in the cell. The polynucleotide can, but need not, be contained in a vector, e.g., a viral vector, and/or can be formulated in a matrix that facilitates introduction of the polynucleotide into a cell, e.g., liposomes or microbubbles. The polynucleotide can be introduced into a cell by contacting the cell with the polynucleotide ex vivo, in which case the cell containing the polynucleotide can, but need not, be administered to a subject. The polynucleotide also can be introduced into a cell by contacting the cell with the polynucleotide in vivo.

The epigenetic silenced gene can be any gene identified using a method as disclosed herein, and examining a particular cell type such as a particular cancer cell type. Epigenetic silenced genes in colorectal cancer cells are exemplified herein by the genes listed in Table 1, for which GenBank Accession Nos. Polynucleotide sequences encompassing portions of the genes of Table 1 can be obtained, for example, by RT-PCR of nucleic acid molecules obtained from colorectal cancer cells using amplification primer pairs as set forth in Table 3 (SEQ ID NOS: 149 to 296; e.g., SEQ ID NOS: 149 and 150, or SEQ ID NOS: 151 and 152, etc.). Epigenetic silenced genes in colorectal cancer cells and/or gastric cancer cells are exemplified by PTGS2, CDKN2A, TIMP3, S100A10, SFRP1, CXX1, SEZZ6L, KIAA0786, TIMP2, PCDH8, FOLH1, and SNRPN, which do not exhibit detectable basal expression, and are re-expressed upon treatment with DAC, but not with TSA; HOXA1, GRO3, and DLX7, which exhibit a basal level of expression that is increased upon treatment with DAC, but not TSA; and POR1, MBNL, TRADD, PDIP, RAD23B, RPL13, GNAI2, PPP1R21A, FPGT, and TRIM32, which are up-regulated by TSA alone, whereas their basal expression and up-regulation with DAC vary among genes.

The present invention further relates to a method for treating a cancer patient, wherein cancer cells in the patient exhibit epigenetic silenced expression of at least one gene. Such a method can be performed, for example, by restoring expression of one or more epigenetic silenced genes in cancer cells in the patient. For example, where at least one epigenetic silenced gene is a methylation silenced gene, the patient can be treated by administering a demethylating agent to the subject in an amount sufficient to restore expression of the methylation silenced gene(s) in cancer cells in the subject. Alternatively, or in addition, the patient can be treated by administering at least one polynucleotide encoding at least one polypeptide encoded by one or more of the epigenetic silenced genes to the subject under conditions sufficient for expression of the at least one polypeptide in cancer cells in the subject. Where a polynucleotide is administered to the patient, the polynucleotide can be contained in a vector (e.g., a viral vector) preferably an expression vector, and/or can be formulated in a matrix that facilitates uptake of the polynucleotide by a target cancer cell (e.g., in a liposome).

The cancer to be treated according to a method of the invention can be any type of cancer, including, for example, a carcinoma or a sarcoma. For example, wherein the cancer is a colorectal cancer, a gastric cancer, or colorectal cancer and gastric cancer, a patient can be treated by restoring expression of one or more epigenetic silenced genes, including, PTGS2, CDKN2A, TIMP3, S100A10, SFRP1, CXX1, SEZZ6L, KIAA0786, TIMP2, PCDH8, FOLH1, SNRPN, HOXA1, GRO3, DLX7, POR1, MBNL, TRADD, PDIP, RAD23B, RPL13, GNAI2, PPP1R21A, FPGT, TRIM32, a family member thereof, or a combination thereof. The SFRP genes, including SFRP1, SFRP2, SFRP4, and SFRP5, provide an example of a family of genes in which one or more is epigenetically silenced in colorectal cancer cells, gastric cancer cells, or both.

The present invention also relates to a method for selecting a therapeutic strategy for treating a cancer patient. Such a method can be performed, for example, by identifying at least one methylation silenced gene associated with the cancer, according to a method as disclosed herein (i.e., by contacting an array of nucleotide sequences representative of a genome with nucleic acid subtraction products and detecting selective hybridization of nucleic acid subtraction products to a subpopulation of nucleotide sequences of the array; and selecting an agent useful for restoring expression of one or more of the identified methylation silenced gene in cancer cells of the patient. For example, the selected agent can be a polynucleotide encoding an identified methylation silenced gene, for example, a polynucleotide encoding a polypeptide encoded by a PTGS2, CDKN2A, TIMP3, S100A10, SFRP1, CXX1, SEZZ6L, KIAA0786, TIMP2, PCDH8, FOLH1, SNRPN, HOXA1, GRO3, or DLX7 gene, a family member of such a gene, or a combination of such genes. The selected agent for restoring expression of a methylation silenced gene also can be a demethylating agent such as DAC.

Accordingly, the present invention further relates to a method of treating a subject suffering from a colorectal cancer, a gastric cancer, or both, wherein cells associated with the cancer contain at least one methylation silenced gene. Such a method can be performed, for example, by administering an amount of an agent that restores expression of the at least one methylation silenced gene to the subject sufficient to restore expression of the methylation silenced gene in cells associated with the cancer. The agent can be a polynucleotide encoding the at least one methylation silenced gene, for example, a polynucleotide encoding a polypeptide encoded by a PTGS2, CDKN2A, TIMP3, S100A10, SFRP1, CXX1, SEZZ6L, KIAA0786, TIMP2, PCDH8, FOLH1, SNRPN, HOXA1, GRO3, and/or DLX7 gene, a family member thereof, or a combination thereof; or can be a demethylating agent such as DAC. An agent useful for treating a subject suffering from a colorectal cancer, a gastric cancer, or both, can be contacted with cells of the cancer ex vivo, after which the cells can be administered back into the patient; or the agent can be administer to a site of the cancer cells in the patient.

The present invention further relates to an isolated oligonucleotide, which has a nucleotide sequence as set forth in any one of SEQ ID NOS: 1 to 296, as well as to a plurality of isolated oligonucleotides, which includes at least two of the isolated oligonucleotides as set forth in SEQ ID NOS: 1 to 296. In addition, the invention relates to an amplification primer pair, which includes a forward primer and a reverse primer as set forth in SEQ ID NOS: 1 to 296 (e.g., SEQ ID NOS: 1 and 2, SEQ ID NOS: 3 and 4, SEQ ID NOS: 5 and 6, etc.), wherein the amplification primer pair can amplify a nucleotide sequence of a gene as listed in Table 1. In one aspect, an amplification primer pair of the invention can be used to specifically amplify a methylated 5' regulatory region of the nucleic acid molecule, such amplification primer pairs being exemplified by SEQ ID NOS: 23 and 24, SEQ ID NOS: 111 and 112, SEQ ID NOS: 115 and 116, SEQ ID NOS: 119 and 120, SEQ ID NOS: 125 and 126, SEQ ID NOS: 129 and 130, SEQ ID NOS: 133 and 134, SEQ ID NOS: 139 and 140 or SEQ ID NOS: 143 and 144, which can amplify SFRP family members having a methylated 5' regulatory region. In another aspect, an amplification primer pair of the invention can be used to specifically amplify an unmethylated 5' regulatory region of the nucleic acid molecule, such amplification primer pairs being exemplified by SEQ ID NOS: 25 and 26, SEQ ID NOS: 113 and 114, SEQ ID NOS: 117 and 118, SEQ ID NOS: 121 and 122, SEQ ID NOS: 127 and 128, SEQ ID NOS: 131 and 132, SEQ ID NOS: 135 and 136, SEQ ID NOS: 141 and 142 or SEQ ID NOS: 145 and 146, which can amplify SFRP family members having an unmethylated 5' regulatory region.

The present invention also relates to a kit, which contains at least one isolated oligonucleotide of the invention, including, for example, a plurality of such isolated oligonucleotides. In one embodiment, a plurality of isolated oligonucleotides of a kit of the invention includes at least one amplification primer pair (i.e., a forward primer and a reverse primer), and can include a plurality of amplification primer pairs, including, for example, amplification primer pairs as set forth in Table 2, Table 3, and/or Table 4. As such, a kit of the invention can contain, for example, one or a plurality of methylation specific amplification primer pairs, unmethylation specific amplification primer pairs, or a combination of methylation specific amplification primer pairs and unmethylation specific amplification primer pair, including methylation specific primer pairs and unmethylation specific primer pairs useful for amplifying a methylated form or an unmethylated form of a particular gene that is known to be or suspected of being methylation silenced in one or more types of cancer cells.

A kit of the invention can further include additional reagents, which can be useful, for example, for a purpose for which the oligonucleotides of the kit are useful. For example, where a kit contains one or a plurality of methylation specific and/or unmethylation specific amplification primers, the kit can further contain, for example, control polynucleotides, which can be methylated or unmethylated; one or more reagents that modify methylated cytosine residues, and/or one or more reagents for performing an amplification reaction. Where the kit contains one or plurality of oligonucleotides that selectively hybridize to a methylated or to an unmethylated gene sequence, the kit can further contain, for example, a methylation sensitive restriction endonuclease.

BRIEF DESCRIPTION OF THE DRAWINGS

FIG. 2 provides a summary of MSP analyses of the SFRP genes in 124 primary CRC samples (see Example 1). Gene names are indicated at the top. Each row represents a primary CRC tumor. Gray boxes and open boxes indicate methylation and no methylation, respectively.

DETAILED DESCRIPTION OF THE INVENTION

Figure 1:
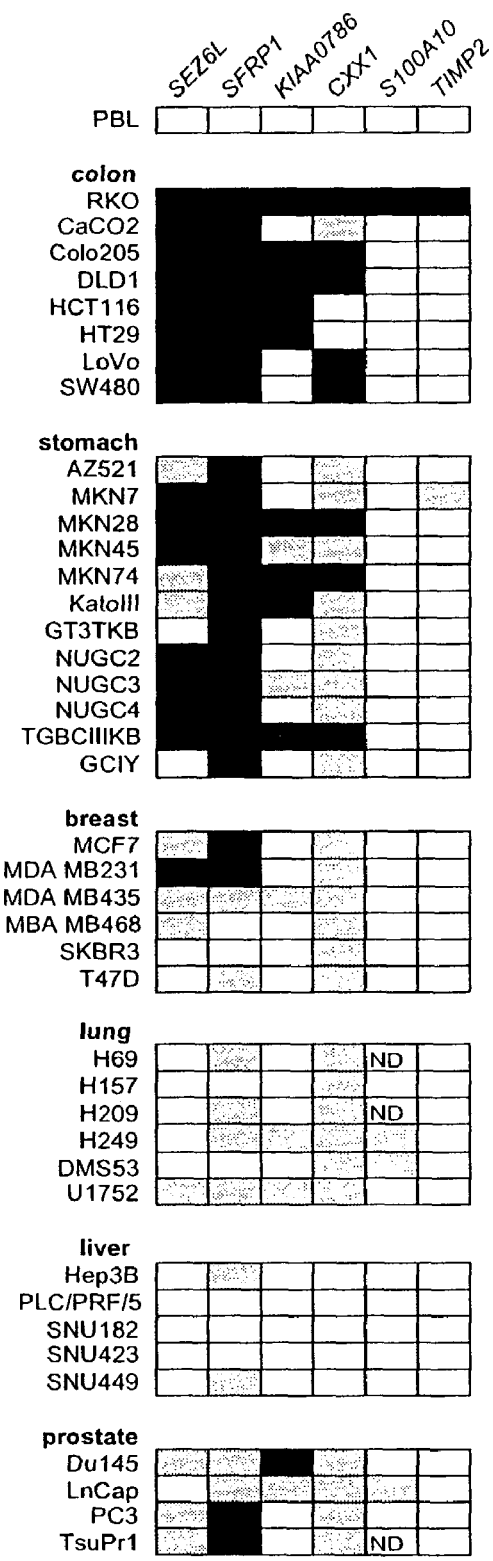
FIG. 1 provides a summary of methylation specific PCR (MSP) analyses of 6 genes from Group 1a (see Table 1) in a series of human cancer cell lines from various origins. Gene names are indicated on the top, and cell line names are indicated on the left. Black boxes indicate full methylation, gray boxes and open boxes indicate partial methylation and no methylation, respectively. "ND" indicates not determined (because of lack of amplification in MSP).

The present invention is based on the development of a method for identifying epigenetically silenced genes in a cell genome, for example, a cancer cell genome. The method is exemplified by the identification of 74 genes that are epigenetically silenced in colorectal carcinoma (CRC) cells, including genes that are silenced due to methylation and/or histone deacetylation. As disclosed herein, a pattern of tumor profiling was revealed, as exemplified by the identification of methylation silencing of SFRP1, SEZ6L, LPPH1 and CXX1 genes in CRC and gastric carcinoma (GC). Such tumor profiling extended to related family members of the SFRP1 gene, wherein, in CRC and GC, hypermethylation of SFRP2, SFRP4, and SFRP5 also was detected (SFRP3 lacks CpG islands in the 5' regulatory region). Accordingly, the present invention provides a method for identifying epigenetically silenced genes associated with a cancer, and further provides methods of detecting a cancer associated with epigenetic silencing of gene expression, methods of treating a patient having such a cancer, and compositions useful for practicing such methods.

Aberrant hypermethylation of gene promoters is recognized as a major mechanism associated with inactivation of tumor suppressor genes in cancer. Transcriptional silencing can be mediated by methylation and/or histone deacetylase (HDAC) activity, with the methylation being dominant. As disclosed herein, a cDNA microarray based analysis was used to screen for genes that are epigenetically silenced in human CRC. A screen of over 10,000 genes identified a substantial number of epigenetically silenced genes, including several exhibiting promoter hypermethylation (i.e., methylation silenced) and others with unmethylated promoters, for which increased expression was produced by HDAC inhibition (see Example 1). Validity of the disclosed method is provided by determining that many of the hypermethylated genes have high potential for roles in tumorigenesis by virtue of their predicted function or chromosome position. A group of genes was identified that are preferentially hypermethylated in CRC and GC, including the SFRP1, gene, which belongs to a gene family that, as disclosed herein, also were frequently hypermethylated in CRC. In addition to suggesting a mechanism for loss of tumor suppressor gene function, the present results provide a molecular marker panel that can detect essentially all CRC (see FIG. 2).

Cancer progression is fostered not only by genetically, but also by epigenetically, determined alterations in gene function. The latter involve aberrantly hypermethylated CpG islands in gene promoters with loss of transcription of the genes. Recognition of this promoter hypermethylation has developed a growing effort to randomly screen the cancer genome to identify such loci. These search strategies, including identification of CpG island hypermethylation in regions of high frequency loss of heterozygosity (LOH) and throughout the genome, have all proven to have utilities for identification of tumor specifically hypermethylated CpG islands. However, each suffers from either identifying some sites not associated with gene promoters, potential bias of utilized methylation sensitive restriction sites for CpG island subsets or lack of the site in numerous islands, and/or the need to laboriously search for nearby genes once the altered locus is identified.

The presently disclosed microarray based strategy obviates the disadvantages of previous methods by coupling gene expression status to epigenetic regulation. Furthermore, the approach exploits the observation that silencing of hypermethylated genes in cancer can be dependent on both dense CpG island methylation and HDAC activity (Cameron et al., Nature Genet. 21:103-107, 1999, which is incorporated herein by reference). As exemplified using colon cancer cells, the disclosed method robustly identifies new genes for which transcriptional repression can have a key role in tumorigenesis. Remarkably, the disclosed genomic screening method allowed an identification of gene hypermethylation events that cluster to specific tumor types, and can simultaneously involve multiple members of a single gene family (Example 1).

Accordingly, methods are provided for identifying epigenetically silenced genes, for example, methylation silenced genes, that are associated with a cancer. In one embodiment, the invention provides a method of identifying at least one epigenetically silenced gene associated with at least one cancer. As used herein, the term "at least one" means 1, 2, 3, 4, 5, 6, 7, 8, 9, 10, or more. For example, the disclosed microarray method identified 74 genes that were epigenetically silenced in colorectal cancer cells. Furthermore, it was determined that several of the genes that were identified as epigenetically silenced in CRC also were epigenetically silenced in gastric cancer cells. As such, the method identified epigenetically silenced genes associated with CRC and/or GC.

The term "epigenetically silenced" or "epigenetic silenced", when used in reference to a gene, means that the gene is not being transcribed, or is being transcribed at a level that is decreased with respect to the level of transcription of the gene in a corresponding control cell (e.g., a normal cell), due to a mechanism other than a genetic change. Epigenetic mechanisms of gene silencing are well known and include, for example, hypermethylation of CpG dinucleotides in a CpG island of the 5' regulatory region of a gene, and structural changes in chromatin due, for example, to histone acetylation, such that gene transcription is reduced or inhibited. Methods for detecting epigenetic silencing of a gene are disclosed herein and include, for example, detecting re-expression (reactivation) of the gene following contact of a cell with an agent that relieves the epigenetic silencing, for example, with a demethylating agent where the silencing is due to hypermethylation.

As used herein, the term "methylation" or "hypermethylation", when used in reference to a gene, means that cytosine residues of CpG dinucleotides in a CpG island associated with the gene are methylated at the 5'-position, i.e., 5'-methylcytosine. The term "methylation status" is used herein to refer to a relative abundance, including the presence or absence, of methylated cytosine residues of CpG dinucleotides in a CpG island. In general, the cytosine residues in a CpG island are not methylated in a transcriptionally active gene and, therefore, the detection of methylated cytosine residues in a CpG island indicates that expression of the gene is reduced or inhibited. Accordingly, as discussed above, reference herein to a "methylation silenced" gene means that the gene is not being transcribed, or is being transcribed at a level that is decreased with respect to the level of transcription of the gene in a corresponding control cell (generally a normal cell) due to hypermethylation of CpG dinucleotides in a CpG island of the 5' regulatory region of the gene. A consequence of methylation silenced gene expression is that a cell containing the gene has reduced levels of, or completely lacks, a polypeptide encoded by the gene (i.e., the gene product) such that any function normally attributed to the gene product in the cell is reduced or absent.

A method of identifying an epigenetically silenced gene associated with a cancer can be performed, for example, by contacting an array of nucleotide sequences representative of a genome with nucleic acid subtraction products (i.e., nucleic acid molecules corresponding to RNA expressed in cancer cells contacted with at least one agent that reactivates expression of epigenetically silenced genes, but not RNA expressed in normal cells corresponding to the cancer cells) under conditions suitable for selective hybridization of nucleic acid subtraction products to complementary nucleotide sequences of the array; and detecting selective hybridization of nucleic acid subtraction products to a subpopulation of nucleotide sequences of the array, wherein nucleic acid molecules corresponding to RNA expressed in the normal cells corresponding the cancer cells do not hybridize to the subpopulation of nucleotide sequences under such conditions suitable for selective hybridization, whereby the nucleic acid subtraction products that selectively hybridize to the subpopulation of nucleotide sequences of the array represent epigenetically silenced genes of the cancer cells (see Example 1). Reference to "nucleic acid molecules corresponding to RNA" of a cell means RNA such as mRNA or polyA+ RNA, cDNA generated using RNA from the cell as a template, or cRNA generated using RNA or cDNA as a template. For practicing a method of the invention, the nucleic acid molecules corresponding to RNA of a cell generally are detectably labeled, for example, with a radioisotope, a paramagnetic isotope, a luminescent compound, a chemiluminescent compound, a fluorescent compound, a metal chelate, an enzyme, a substrate for an enzyme, a receptor, or a ligand for a receptor; or are capable of being detected, for example, using a detectably labeled probe, such that hybridization of the nucleic acid molecules to nucleotide sequences of the array can be detected.

As used herein, the term "array of nucleotide sequences representative of a genome" means an organized group of nucleotide sequences that are linked to a solid support, for example, a microchip or a glass slide, wherein the sequences can hybridize specifically and selectively to nucleic acid molecules expressed in a cell. The array is selected based on the organism from which the cells to be examined are derived and/or on a tissue or tissues that are to be examined. Generally, the array is representative of the genome of a eukaryotic cell or cell type, particularly a mammalian cell or cell type, and preferably a human cell, including a cell of one or more tissues, as desired (e.g., colorectal epithelial cells). In general, an array of probes that is "representative" of a genome will identify at least about 10% of the expressed nucleic acid molecules in a cell, generally at least about 20% or 40%, usually about 50% to 70%, typically at least about 80% or 90%, and particularly 95% to 99% or more of the expressed nucleic acid molecules of a cell or organism. It should be recognized that the greater the representation, the more likely that a method of the invention can identify all genes that are epigenetically silenced in a cancer. Arrays containing nucleotide sequences representative of specified genomes can be prepared using well known methods, or obtained from a commercial source (e.g., Invitrogen Corp.; Affymetrix), as exemplified by a Human GeneFilters™ Microarray, Release II, array (Research Genetics; now a subsidiary of Invitrogen Corp.) used in the present studies (Example 1).

The agent that reactivates expression of epigenetically silenced genes can be a methyltransferase inhibitor (e.g., 5-aza-2'-deoxycytidine; DAC), a histone deacetylase inhibitor (e.g., trichostatin A; TSA), or a combination of agents such as a combination of DAC and TSA. RNA can be isolated from cells such as cancer cells treated with such an agent or agent, and the RNA, or a cDNA product of the RNA can be contacted with RNA molecules from corresponding cells (e.g., cancer cells) that were not treated with the agent(s) under conditions such that RNA (or cDNA) expressed only in the treated cells can be isolated, thus obtaining nucleic acid subtraction products. Methods for performing a nucleic acid subtraction reaction are well known (Hedrick et al., Nature 308:149-155, 1984, which is incorporated herein by reference), and kits for performing such methods are available from commercial sources (e.g., Gibco/BRL; see Example 1).

Figure 2:
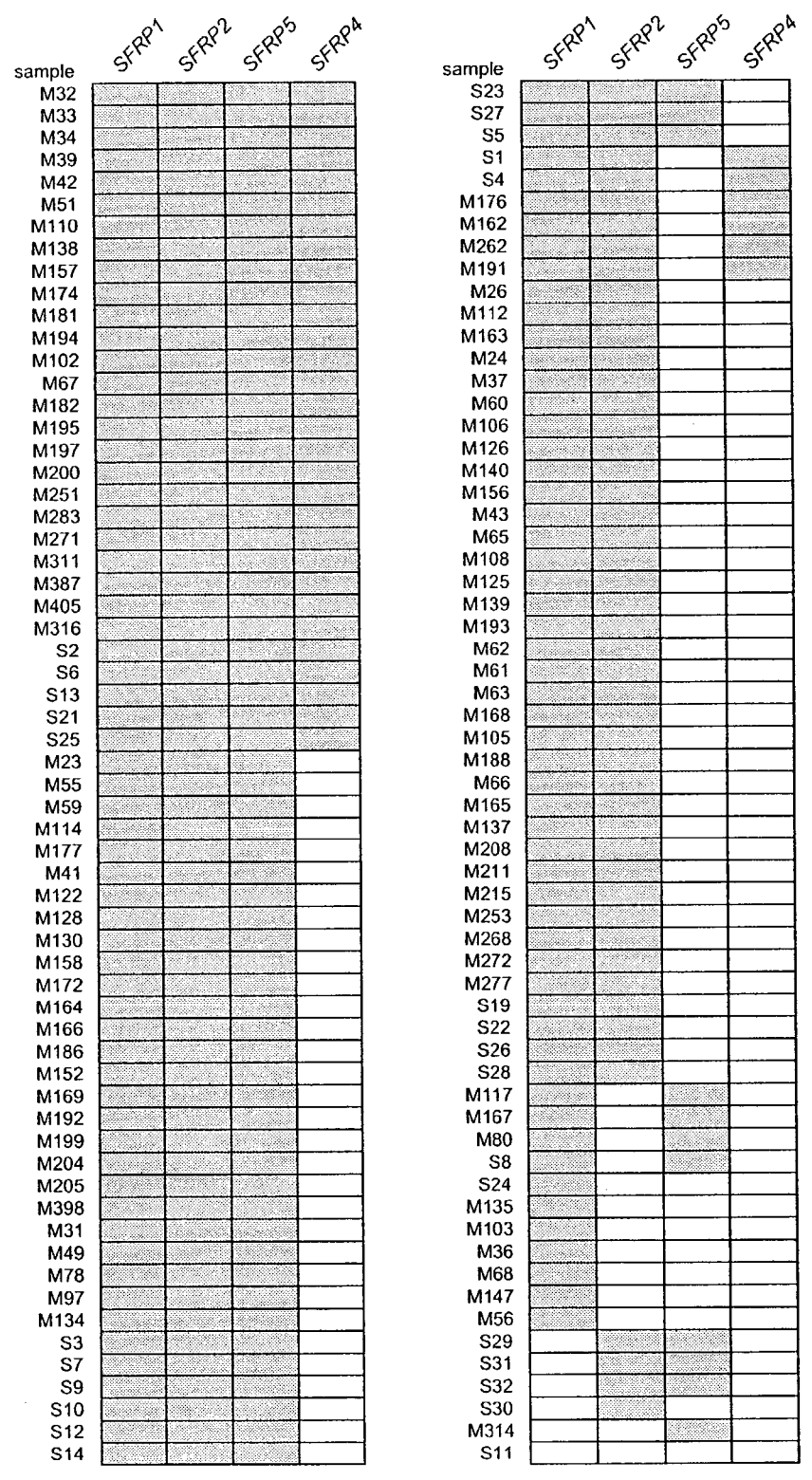

According to a method of the invention, at least one (e.g., 1, 2, 3, 4, 5, or more) epigenetically silenced gene can be associated with at least one (e.g. 1, 2, 3, or more) cancer. The cancer can be, for example, a carcinoma or a sarcoma, including one or more specific types of cancer, e.g., an alimentary/gastrointestinal tract cancer, a liver cancer, a skin cancer, a breast cancer, an ovarian cancer, a prostate cancer, a lymphoma, a leukemia, a kidney cancer, a lung cancer, a muscle cancer, a bone cancer, or a brain cancer. Epigenetically silenced genes associated with a cancer are exemplified herein by the genes listed in Table 1 (and for which GenBank Accession numbers are provided; see, for example, world wide web, at the URL "ncbi.nlm.nih.gov"), which are associated with CRC and/or GC. With reference to Table 1, epigenetically silenced genes in CRC cells that can be reactivated due to contact of the cells with DAC (i.e., methylation silenced genes) are exemplified by PTGS2, CDKN2A, TIMP3, S100A10, SFRP1, CXX1, SEZZ6L, KIAA0786, TIMP2, PCDH8, FOLH1, SNRPN, HOXA1, GRO3, and DLX7; and epigenetically silenced genes that can be reactivated due to contact of cancer cells with TSA are exemplified by POR1, MBNL, TRADD, PDIP, RAD23B, RPL13, GNAI2, PPP1R21A, FPGT, and TRIM32. Furthermore, as disclosed herein, related family members of the identified epigenetically silenced genes also can be epigenetically silenced, including, for example, SFRP2, SFRP4, and SFPR5, which are related to SFRP1, and which, alone or in combination, were associated with 123 of 124 CRC samples tested (see Example 1; FIG. 2).

The silencing of gene transcription associated with aberrant DNA methylation of CpG dinucleotides in normally unmethylated gene promoter regions is the most widely studied epigenetic abnormality in tumorigenesis. The binding of protein complexes consisting of methyl-CpG-binding domains, transcriptional co-repressors, chromatin remodeling proteins and histone deacetylases to hypermethylated DNA regions results in a transcriptionally repressed (silenced) chromatin state. In eukaryotic cells, methylation of cytosine residues that are immediately 5' to a guanosine residue occurs predominantly in CG poor regions. In contrast, CpG islands generally remain unmethylated in normal cells, except during X chromosome inactivation and parental specific imprinting, where methylation of 5' regulatory regions is associated with transcriptional repression. De novo methylation of the retinoblastoma (Rb) gene has been demonstrated in a small fraction of retinoblastomas (Sakai et al., Am. J. Hum. Genet. 48:880, 1991), and aberrant methylation of the VHL gene was found in a subset of sporadic renal cell carcinomas (Herman et al., Proc. Natl. Acad. Sci. USA 91:9700-9704, 1994). Expression of a tumor suppressor gene can also be abolished by de novo DNA methylation of a normally unmethylated 5' CpG island (see, for example, Issa et al., Nature Genet. 7:536, 1994; Merlo et al., Nature Med. 1:686, 1995; Herman et al., Cancer Res. 56:722, 1996).

Aberrant methylation of promoter regions in CpG islands also has been associated with the development of cancer. In hematopoietic malignancies, for example, hypermethylation of E-cadherin (Graff et al., Cancer Res. 55:5195-5199, 1995), DAP-kinase (Katzenellenbogen et al., Blood 93:4347-4353, 1999), and the cell cycle regulators $p15^{INK4B}$ and $p16^{INK4A}$, is associated with gene inactivation (Herman et al., Cancer Res. 57:837-841 1997; Melki et al., Blood 95:3208-3213, 2000; Ng et al., Clin. Canc. Res. 7:1724-1729, 2001). Transcriptional silencing due to hypermethylation also has been detected in the CDKN2A gene (Herman et al., Cancer Res. 55:4525-4530, 1995), MGMT (Esteller et al., Cancer Res. 59:793-797, 1999), and MLH1 gene (Herman et al., Proc. Natl. Acad. Sci. USA 95:6870-6875, 1998).

Hypermethylation of a CpG island at chromosome position 17p13.3 has been observed in multiple common types of human cancers (Makos et al., Proc. Natl. Acad. Sci. USA 89:1929, 1992; Makos et al., Cancer Res. 53:2715, 1993; Makos et al., Cancer Res. 53:2719, 1993), and coincides with timing and frequency of 17p loss and p53 mutations in brain, colon, and renal cancers. Silenced gene transcription associated with hypermethylation of the normally unmethylated promoter region CpG islands has been implicated as an alternative mechanism to mutations of coding regions for inactivation of tumor suppressor genes (Baylin et al., Cancer Cells 3:383, 1991; Jones and Buckley, Adv. Cancer Res. 54:1-23, 1990). This change also has been associated with the loss of expression of VHL, a renal cancer tumor suppressor gene on 3p (Herman et al., supra, 1994), the estrogen receptor gene on 6q (Ottaviano et al., Cancer Res. 54:2552, 1994), and the H19 gene on 11p (Steenman et al., Nature Genetics, 7:433, 1994). Methylation-silenced transcription of the SOCS-1 gene is associated with various cancers, including hepatocellular carcinoma, multiple myeloma, and acute leukemias (Yoshikawa et al., Nat. Genet. 28:29-35, 2001, which is incorporated herein by reference).

Accordingly, the present invention provides a method for identifying a cell that exhibits or is predisposed to exhibiting unregulated growth by detecting, in a test cell, epigenetic silencing of at least one gene as set forth in Table 1, or a combination thereof. For example, the epigenetic silenced gene can be a PTGS2, CDKN2A, TIMP3, S100A10, SFRP1, SFRP2, SFRP4, SFRP5, CXX1, SEZZ6L, KIAA0786, TIMP2, PCDH8, FOLH1, SNRPN, HOXA1, GRO3, DLX7, POR1, MBNL, TRADD, PDIP, RAD23B, RPL13, GNAI2, PPP1R21A, FPGT, or TRIM32 gene, or a combination of such genes. The cell exhibiting, or predisposed to exhibiting unregulated growth, can be a neoplastic cell, which can be, for example, a premalignant cell such as a cell of a gastrointestinal polyp, or can be a cancer cell, for example, a carcinoma cell such as a colorectal cancer cell or a gastric cancer cell, or a sarcoma cell.

In one embodiment, a method of the invention requires, in part, a comparison of the methylation status of a gene in a test cell or sample with the methylation status of a corresponding gene in a corresponding cell exhibiting regulated growth. As used herein, the term "corresponding" means a reference material, with which a test material is being compared. Generally, the reference material provides a control or standard with which the test material is compared. For example, reference to a corresponding unmethylated SFRP gene, with respect to an SFRP gene being examined for methylation status, means that the unmethylated SFRP gene is the same type of gene as the a SFRP gene being examined for methylation status, e.g., the test gene and the corresponding unmethylated gene are both human a SFRP1, genes. Reference to a corresponding cell exhibiting regulated growth, with respect to a test cell, generally refers to a normal cell, i.e., a cell that has a cell cycle and growth pattern characteristic of a population of such cells in a healthy individual, for example, a normal colon epithelial cell where the test cell being examined is suspected of being a CRC cell.

A method of the invention is practiced using a sample comprising a test cell, or an extract of the test cell that includes nucleic acid molecules of the cell, particularly genomic DNA, including all or a portion comprising the CpG island of a 5' regulatory region of the gene that is to be examined for methylation status. Generally, the test cell is a cell that is suspected of being a cell that exhibits unregulated growth, for example, a biopsy sample of suspicious lesion, or is a cell that is (or was) in proximity to a premalignant or malignant cell, for example, cell samples taken at one or few places outside of the region of a suspicious lesion, such test cell providing an indication, for example, of the extent to which a surgical procedure should be performed, or a cell sample taken from a surgical margin, such test cells being useful for determining whether a cancer has been completely removed, or for determining whether a cancer has recurred.

A test cell examined according to a method of the invention also can be a primary cell that has been obtained from a subject and placed in culture, for example, for the purpose of establishing a primary cell culture that exhibits substantially the same growth characteristics as the cells from which the culture was established, or for the purpose of treating and/or expanding the cells for readministration to the subject. For example, colon epithelial cells can be obtained from a cancer patient suffering from a CRC, wherein the cells exhibit methylation silenced expression of one or more genes associated with the cancer. The cells can be treated in culture using one or more agent to be tested for an ability to restores expression of the silenced gene(s), thus providing a means to identify an agent that can be useful for treating the cancer patient, or another patient having a CRC characterized by methylation silencing of one or more of the same genes.

A test cell can be obtained from a subject in any way typically used in clinical setting for obtaining a sample containing the cells. For example, the test cells (or a sample comprising the test cells) can be obtained by a biopsy procedure such as needle biopsy of an organ or tissue containing the cells to be tested. As such, the test cells can be obtained from a gastrointestinal tract sample (e.g., a biopsy of a polyp), a liver sample, a bone marrow sample, a skin sample, a lymph node sample, a kidney sample, a lung sample, a muscle sample, a bone sample, a brain sample, or the like. The test cell also can be a component of a biological fluid, for example, blood, lymph, cerebrospinal fluid, saliva, sputum, stool, urine, or ejaculate. If appropriate, the test cells also can be obtained by lavage, for example, for obtaining test cells from the colon, uterus, abdominal cavity, or the like, or using an aspiration procedure, for example, for obtaining a bone marrow sample.

A method of the invention also can be practiced using an extract of a test cell, wherein the extract includes nucleic acid molecules of the test cell, particularly genomic DNA, including all or a CpG island containing portion of the gene or genes to be examined. The extract can be a crude extract comprising, for example, a freeze-thawed sample of a tissue containing the test cells; can comprise partially purified genomic DNA, which can include, for example, components of the nuclear matrix; or can comprise substantially purified genomic DNA, which is obtained, for example, following treatment with a protease and alcohol precipitation. In certain embodiments, the test cell also can be a component of a histologic sample that is embedded in paraffin.

Where the epigenetic silencing includes methylation silencing, the method for identifying a cell that exhibits or is predisposed to exhibiting unregulated growth is performed by detecting methylation of one or more target genes in the cell. Methylation of a CpG dinucleotide in a CpG island of a gene can be detected using any of various well known methods for detecting CpG methylation of a nucleic acid molecule. Such methods include contacting the gene with one or a series of chemical reagents that selectively modify either unmethylated cytosine residues or methylated cytosine residues, but not both, such that the presence or absence of the modification can be detected; contacting the gene sequence with a methylation sensitive restriction endonuclease, which has a recognition site that includes a CpG dinucleotide, and that cleaves a recognition site either having a methylated cytosine residue of the CpG or lacking a methylated cytosine residue of the CpG, but not both, such that the presence or absence of cleavage of the sequence can be detected; or contacting a nucleic acid molecule comprising the gene with an oligonucleotide probe, primer, or amplification primer pair that selectively hybridizes to the gene sequence and allows a determination to made as to whether the CpG methylation is present. Examples of such methods are provided herein, and modifications and variations on such methods are well known in the art.

Methylation of a target gene can be detected, for example, by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, whereby cleavage of the nucleic acid molecule is indicative of methylation and, therefore, methylation silencing of the gene of the test cell. Methylation sensitive restriction endonucleases are well known and include, for example, Acc III, Ban I, BstN I, Msp I, and Xma I. Alternatively, or in addition, methylation silencing can be detected by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, provided the cytosine residue of the CpG dinucleotide is unmethylated, whereby a lack of cleavage of the nucleic acid molecule is indicative of methylation silencing of the gene of the test cell. Such methylation sensitive restriction endonucleases are exemplified by Acc II, Ava I, BssH II, BstU I, Hpa II, and Not I.

The presence or absence of cleavage of a nucleic acid molecule comprising a target gene sequence by a methylation sensitive restriction endonuclease can be identified using any method useful for detecting the length or continuity of a polynucleotide sequence. For example, cleavage of the target gene sequence can be detected by Southern blot analysis, which allows mapping of the cleavage site, or using any other electrophoretic method or chromatographic method that separates nucleic acid molecules on the basis of relative size, charge, or a combination thereof. Cleavage of a target gene also can be detected using an oligonucleotide ligation assay, wherein, following contact with the restriction endonuclease, a first oligonucleotide that selectively hybridizes upstream of and adjacent to a restriction endonuclease cleavage site and a second oligonucleotide that selectively hybridizes downstream of and adjacent to the cleavage site are contacted with the target gene sequence, and further contacted with a ligase such that, in the absence of cleavage the oligonucleotides are adjacent to each other and can be ligated together, whereas, in the absence of cleavage, ligation does not occur. By determining the size or other relevant parameter of the oligonucleotides following the ligation reaction, ligated oligonucleotides can be distinguished from unligated oligonucleotides, thereby providing an indication of restriction endonuclease activity.

Methylation silencing of a gene also can be detected by contacting a 5' regulatory region of the nucleic acid molecule comprising the gene of the test cell with a chemical reagent that selectively modifies either an unmethylated cytosine residue or a methylated cytosine residue, and detecting a product generated due to said contacting, wherein the product is indicative of methylation of a cytosine residue in a CpG dinucleotide of the gene, thereby detecting methylation silencing of the gene of the test cell. For example, the product can be detected using an electrophoresis method, a chromatography method, a mass spectrometry method, or a combination of such methods.

In one aspect of this embodiment, the gene is contacted with hydrazine, which modifies cytosine residues, but not methylated cytosine residues, then the hydrazine treated gene sequence is contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding unmethylated gene sequence, gaps are apparent at positions in the test gene contained methylated cytosine residues. As such, the presence of gaps is indicative of methylation of a cytosine residue in the CpG dinucleotide in the target gene of the test cell.

In another aspect, a nucleic acid molecule comprising the target gene is contacted with a chemical reagent comprising bisulfite ions, for example, sodium bisulfite, which converts unmethylated cytosine residues to bisulfite modified cytosine residues, then the bisulfite ion treated gene sequence is exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. As such, the sulfonate group can be removed by exposure to alkaline conditions, resulting in the formation of uracil. The DNA then can amplified, for example, by PCR, and sequenced to determine the methylation status of all CpG sites. Uracil is recognized as a thymine by Taq polymerase and, upon PCR, the resultant product contains cytosine only at the position where 5-methylcytosine was present in the starting template DNA. By comparing the amount or distribution of uracil residues in the bisulfite ion treated gene sequence of the test cell with a similarly treated corresponding unmethylated gene sequence, detection of a decrease in the amount or distribution of uracil residues in the gene from the test cell is indicative of methylation of cytosine residues in CpG dinucleotides in the target gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

As used herein, the term "selective hybridization" or "selectively hybridize" or "specific hybridization" refers to an interaction of two nucleic acid molecules that occurs and is stable under moderately stringent or highly stringent conditions. As such, selective hybridization preferentially occurs, for example, between an oligonucleotide and a target nucleic acid molecule, and not substantially between the oligonucleotide and a nucleic acid molecule other than the target nucleic acid molecule, including not with nucleic acid molecules encoding related but different members of a gene family. Generally, an oligonucleotide useful as a probe or primer that selectively hybridizes to a target nucleic acid molecule is at least about 12 to 15 nucleotides in length, generally at least about 18 to 20 nucleotides in length, usually at least about 21 to 25 nucleotides in length, and particularly about 26 to 35 nucleotides in length or. Examples of oligonucleotides useful in practicing the methods of the invention are disclosed herein as SEQ ID NOS: 1 to 296 more (see Tables 2, 3 and 4).

Conditions that allow for selective hybridization can be determined empirically, or can be estimated based, for example, on the relative GC:AT (or GC:AU) content of the hybridizing oligonucleotide and the target nucleic acid molecule, the length of the hybridizing oligonucleotide, and the number, if any, of mismatches between the oligonucleotide and target sequence to which it is to hybridize (see, for example, Sambrook et al., "Molecular Cloning: A laboratory manual (Cold Spring Harbor Laboratory Press 1989)). As such, the conditions used to achieve a particular level of stringency will vary, depending on the nature of the hybridizing nucleic acid molecules. An additional consideration is whether one of the nucleic acids is immobilized, for example, on a filter. An example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 62° C. (high stringency conditions). Hybridization and/or washing can be carried out using only one of these conditions, for example, high stringency conditions, or each of the conditions can be used, for example, for 10 to 15 minutes each, in the order listed above, repeating any or all of the steps listed.

Selective hybridization of an oligonucleotide with a target gene (e.g., a gene as listed in Table 1) can be detected, for example, by performing the method using an oligonucleotide that includes a detectable label. The detectable label can be any molecule that conveniently can be linked to the oligonucleotide and detected using readily available equipment. For example, the detectable label can be a fluorescent compound such a Cy3, Cy5, Fam, fluorescein, rhodamine, or a green fluorescent protein or enhanced or modified form thereof; a radionuclide such as sulfur-35, technicium-99, phosphorus-32, tritium or iodine-125; a paramagnetic spin label such as carbon-13, Gd-157, Mn-55, Dy-162, Cr-52, or Fe-56; a luminescent compound such as an aequorin; a chemiluminescent compound; a metal chelate; an enzyme such as luciferase or β-galactosidase, or a substrate for an enzyme; or a receptor or a ligand for a receptor, for example, biotin. The means for detecting the detectable label will be selected based on the characteristics of the label, as will the means for linking the label to an oligonucleotide (see, for example, Hermanson, "Bioconjugate Techniques" (Academic Press 1996), which is incorporated herein by reference).

Selective hybridization also can be detected, for example, by utilizing the oligonucleotide as a substrate for a primer extension reaction, further contacting the sample with deoxyribonucleotides (dNTPs), including, if desired, a detectable dNTP (e.g., a fluorescently labeled dNTP, a digoxigenin labeled dNTP, or a biotin labeled dNTP), and a DNA dependent DNA polymerase under conditions sufficient for the primer extension reaction to proceed, and detecting a product of the primer extension reaction. Conditions for performing a primer extension reaction are well known in the art (see, for example, Sambrook et al., supra, 1989).

The amount or distribution of uracil residues in a bisulfite ion treated nucleic acid molecule comprising a target gene sequence following exposure to alkaline conditions also can be detected using an amplification reaction such as PCR. An amplification reaction is performed under conditions that allow selective hybridization of the forward and reverse primers of an amplification primer pair to the target nucleic acid molecule. Generally, the reaction is performed in a buffered aqueous solution, at about pH 7-9, usually about pH 8. In addition, the reaction generally is performed in a molar excess of primers to target nucleic acid molecule, for example, at a ratio of about 100:1 primer:genomic DNA. Where the amount of the target nucleic acid molecule in a sample is not known, for example, in a diagnostic procedure using a biological sample, a range of primer amounts can be used in samples run in parallel, although generally even the addition of a small amount of primers will result in a sufficient molar excess such that the amplification reaction can proceed.

The deoxyribonucleoside triphosphates, dATP, dCTP, dGTP, and dTTP, can be added to the synthesis mixture either separately or as a mixture, which can further include the primers, in adequate amounts and the resulting solution is heated to about 90°-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction, generally a polymerase, and the reaction is allowed to occur under conditions as disclosed herein (see Example 1) or otherwise known in the art. Where the polymerase is heat stable, it can be added together with the other reagents. The polymerase can be any enzyme useful for directing the synthesis of primer extension products, including, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes, as are well known in the art and commercially available. The amplification products can be identified as methylated or non-methylated by a sequencing method, oligomer restriction (Saiki et al., BioTechnology 3:1008-1012, 1985), allele-specific oligonucleotide probe analysis (Conner et al., Proc. Natl. Acad. Sci. USA 80:278, 1983), oligonucleotide ligation assays (Landegren et al., Science 241:1077, 1988), and the like (see, also, Landegren et al., Science 242:229-237, 1988).

In one embodiment, the amplification is performed by contacting the target gene sequence (e.g., a gene as listed in Table 1) with an amplification primer pair comprising a forward primer and a reverse primer under conditions suitable for amplification, wherein at least one primer of the primer pair comprises an oligonucleotide that selectively hybridizes to a target gene sequence containing uracil residues, whereby generation of an amplification product is indicative of methylation of cytosine residues in CpG dinucleotides in the target gene of the test cell. In another embodiment, the amplification reaction is performed by contacting the target gene sequence with an amplification primer pair comprising a forward primer and a reverse primer under conditions suitable for amplification, wherein both primers of the primer pair selectively hybridize to a target gene sequence containing cytosine residues, but not to a target gene sequence containing uracil residues, whereby generation of an amplification product is indicative of a lack of methylation of cytosine residues in CpG dinucleotides in the target gene of the test cell.

In still another embodiment, a methylation-specific amplification reaction such as methylation-specific PCR (MSP) is used alone, or in combination with bisulfite treatment, to detect the methylation status of a nucleic acid molecule (see U.S. Pat. Nos. 6,265,171; 6,200,756; and 6,017,704, each of which is incorporated herein by reference; see, also, Example 1). MSP is a particularly sensitive method that allows detection of low numbers of methylated alleles and the use of small amounts of a nucleic acid sample, including paraffin-embedded materials, and also can be conveniently adapted to a multiplex analysis, including, for example, simultaneous detection of unmethylated and methylated products in a single sample, thus providing an internal control.

The amplification primer pairs used in an MSP reaction are designed to specifically distinguish between bisulfite untreated or unmodified DNA, and methylated and unmethylated DNA. MSP primer pairs for unmethylated DNA (unmethylation specific primer pairs) generally have a thymidine residue in the 3'-CpG pair to distinguish it from the cytosine residue retained in methylated DNA, and the complement is designed for the antisense primer. MSP primer pairs usually contain relatively few cytosine or guanine residues in the sequence because cytosine is absent in the sense (forward) primer and the guanine is absent in the antisense (reverse) primer; cytosine becomes modified to uracil, which is amplified as thymidine in the amplification product. MSP unmethylation (MSP(U)) specific primer pairs and MSP methylation (MSP(M)) specific are exemplified in Tables 2 and 3. For example, amplification primer pairs useful for such a method include, for example, a primer pair as set forth in SEQ ID NO: 23 and 24, SEQ ID NOS: 111 and 112, SEQ ID NOS: 115 and 116, SEQ ID NOS: 119 and 120, SEQ ID NOS: 125 and 126, SEQ ID NOS: 129 and 130, SEQ ID NOS: 133 and 134, SEQ ID NOS: 139 and 140, or SEQ ID NOS: 143 and 144, which are methylation specific primers useful for detecting methylation of an SFRP1, SFRP2, SFRP4, or SFRP5 gene 5' regulatory region; and a primer pair as set forth in SEQ ID NOS: 25 and 26, SEQ ID NOS: 113 and 114, SEQ ID NOS: 117 and 118, SEQ ID NOS: 121 and 122, SEQ ID NOS: 127 and 128, SEQ ID NOS: 131 and 132, SEQ ID NOS: 135 and 136, SEQ ID NOS: 141 and 142, or SEQ ID NOS: 145 and 146, which are unmethylation specific primers useful for detecting a lack of methylation of an SFRP1, SFRP2, SFRP4, or SFRP5 gene 5' regulatory region. In view of the exemplified methylation-specific and unmethylation-specific primer pairs, and the availability of nucleotide sequences comprising portions of target genes such as those listed in Table 1, it will be recognized that additional methylation-specific and unmethylation-specific primer pairs useful for amplification of a methylated or an unmethylated gene as listed in Table 1 or other identified target gene, as well as for family members related to the listed genes such as the SFRP family members, readily can be made.

Accordingly, in one aspect, MSP is used for detecting the amount or distribution of uracil residues in a bisulfite ion treated target genes following alkaline treatment. Such a method can be performed by contacting the gene sequence with a first amplification primer pair and a second amplification primer pair under conditions suitable for amplification, wherein the first amplification primer pair comprises a forward primer and a reverse primer, and at least one primer of the first primer pair comprises an oligonucleotide that selectively hybridizes to a nucleotide sequence of the target gene that contains uracil residues, and wherein the second amplification primer pair comprises a forward primer and a reverse primer, and both primers of the second primer pair selectively hybridize to a target gene containing cytosine residues, but not to a target gene sequence containing uracil residues, and wherein an amplification product, if any, generated by the first primer pair has a first length, and an amplification product, if any, generated by the second primer pair has a second length, which is different from the first length, whereby the length of the amplification products is indicative of the amount or distribution of uracil residues and, therefore, of methylation of cytosine residues in CpG dinucleotides in the target gene of the test cell.

The amount or distribution of uracil residues also can be detected by contacting the 5' regulatory region of the gene with a first amplification primer pair and a second amplification primer pair under conditions suitable for amplification, wherein the first amplification primer pair comprises a forward primer and a reverse primer, wherein at least one primer of the first primer pair comprises an oligonucleotide that selectively hybridizes to a nucleotide sequence of the 5' regulatory region of the gene containing uracil residues, and wherein the second amplification primer pair comprises a forward primer and a reverse primer, wherein both primers of the second primer pair selectively hybridize to a nucleotide sequence of the 5' regulatory region of the gene containing cytosine residues, but not to a corresponding nucleotide sequence of the 5' regulatory region of the gene containing uracil residues, and wherein an amplification product, if any, generated by the first primer pair has a first length, and wherein an amplification product, if any, generated by the second primer pair has a second length, which is different from the first length, whereby the length of the amplification products is indicative of uracil residues and, therefore, methylation of cytosine residues in CpG dinucleotides in the 5' regulatory region of the gene, thereby detecting methylation silencing of the gene of the test cell.

Methylation silencing of a gene in a cell exhibiting or suspected of exhibiting unregulated growth (e.g., a gene associated with a cancer) also can be identified by contacting a test cell with a demethylating agent, and detecting increased expression of an RNA encoded by the gene as compared to a level of expression of the RNA in a test cell not contacted with a demethylating agent. Such a method can further include detecting methylation, if any, of cytosine residues in a CpG dinucleotide in a CpG island of the 5' regulatory region of the gene in a corresponding cell exhibiting regulated growth, or an extract of the corresponding cell The demethylating agent can be a methyltransferase inhibitor such as DAC. Increased expression of an RNA can be detected using any method for detecting RNA, including, for example, northern blot analysis, a reverse transcription-polymerase chain reaction assay, or selective hybridization to an array of nucleotide sequences as disclosed herein. Accordingly, the methods of the invention can be performed in a high throughput format, wherein the test cell, or extract of the test cell, comprises one of a plurality of test cells, or extracts of the test cells, or a combination thereof, and each of the test cells, or extracts of the test cells, of the plurality is the same or different, or a combination thereof.

In adapting the methods of the invention to a high throughput format, the test cells, or extracts of the test cell, can be arranged in an array, which can be an addressable array, on a solid support such as a microchip, a glass slide, or a bead, and the cells (or extracts) can be contacted serially or in parallel with an oligonucleotide probe or primer (or primer pair) as disclosed herein. Samples arranged in an array or other reproducible pattern can be assigned an address (i.e., a position on the array), thus facilitating identification of the source of the sample. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays. Conveniently, cells or extracts at a position in the array can be contacted with two or more oligonucleotide probes or primers (or primer pairs), wherein the oligonucleotides are differentially labeled or comprise a reaction that generates distinguishable products, thus providing a means for performing a multiplex assay. Such assays can allow the examination of one or more, particularly 2, 3, 4, 5, 10, 15, 20, or more genes to identify epigenetically silenced genes in a test cell.

The present invention also provides oligonucleotides, which can be useful as probes or primers for identifying an epigenetic silenced gene (or the absence thereof). As used herein, the term "oligonucleotide", "polynucleotide", or "nucleic acid molecule" is used broadly to mean a sequence of two or more deoxyribonucleotides or ribonucleotides that are linked together by a phosphodiester bond. The term "gene" also is used herein to refer to a polynucleotide sequence contained in a genome. It should be recognized, however, that a nucleic acid molecule comprising a portion of a gene can be isolated from a cell or can be examined as genomic DNA, for example, by a hybridization reaction or a PCR reaction. Thus, while in a genome, it may not always be clear as to a specific nucleotide position where a gene begins or ends, for purposes of the present invention, a gene is considered to be a discrete nucleic acid molecule that includes at least the nucleotide sequence set forth in the GenBank Accession Numbers shown in Table 1 for various genes identified and or examined herein.

For convenience of discussion, the term "oligonucleotide" is used herein to refer to a polynucleotide that is used as a probe or primer, whereas the term "polynucleotide" or "nucleic acid molecule" is used more broadly to encompass any sequence of two or more nucleotides, including an oligonucleotide. In addition, the term "nucleotide sequence is used to refer to the molecules that are present on an array. As such, it should be recognized that the various terms used herein to conveniently distinguish different nucleic acid molecules. As such, the terms include RNA and DNA, which can be a gene or a portion thereof, a cDNA, a synthetic polydeoxyribonucleic acid sequence, or the like. Generally, an oligonucleotide or polynucleotide can be single stranded or double stranded, as well as a DNA/RNA hybrid, although it will be recognized that the strands of a double stranded oligonucleotide that is to be used as a probe or primer will be separated, for example, by heating a solution containing the oligonucleotide above the melting temperature of the particular oligonucleotide.

The terms "oligonucleotide", "polynucleotide", and the like as used herein include naturally occurring nucleic acid molecules, which can be isolated from a cell, as well as fragments thereof as produced, for example, by a restriction endonuclease digestion, and synthetic molecules, which can be prepared, for example, by methods of chemical synthesis or by enzymatic methods such as by PCR. In various embodiments, an oligonucleotide or polynucleotide of the invention can contain nucleoside or nucleotide analogs, or a backbone bond other than a phosphodiester bond, for example, a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994); Ecker and Crooke, *BioTechnology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium, a cell or in a living subject, since the modified polynucleotides can be designed to be less (or, if desired, more) susceptible to degradation.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide (or oligonucleotide) also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). As such, the polynucleotide can be prepared using a method such as conventional phosphotriester and phosphodiester methods, including, for example, an automated method such as that using diethylphosphoramidites (see Beaucage et al., *Tetrahedron Lett.*, 22:1859-1862, 1981), or a method whereby the oligonucleotides are synthesized on a modified solid support (see U.S. Pat. No. 4,458,066).

An oligonucleotide of the invention, which can selectively hybridize to a target nucleic acid molecule and can be used as a reagent for detecting expression and/or methylation (or lack of methylation; "unmethylation") of a gene, is designed to selectively hybridize to a nucleotide sequence within about 2000 nucleotides upstream (5') or downstream (3') of the target gene, and generally within about 1000 nucleotides of the region comprising the CpG island that is to be examined for cytosine methylation, usually within about 500 nucleotides of the site to be examined. In addition, as indicated above, an oligonucleotide of the invention, or useful in a method of the invention, is at least about 12 nucleotides in length, generally at least about 14 or 15 nucleotides in length, usually at least about 18 to 20 nucleotides, and can be about 25, 30, 35 or more nucleotides in length, such that it can selectively hybridize to a target nucleic acid molecule (see, for example, Tables 2, 3, and 4). It will be recognized that the length of the oligonucleotide will depend, in part, on the target gene. For example, when the target gene is one of a family of closely related genes having regions of substantial sequence similarity, a longer oligonucleotide can be used to assure selective hybridization to the target gene and minimal, if any, cross-hybridization to the related gene sequence(s).

Oligonucleotides of the invention are designed to be substantially complementary to at least one strand of a double stranded nucleic acid molecule corresponding to a genomic locus (or to each of both strands where an intervening sequence is to be amplified) and, where they are to be used for differentiating methylated from unmethylated cytosine residues, will include the appropriate guanine or cytosine residues, as discussed above. Oligonucleotides of the invention are exemplified by amplification primer pairs useful 1) for RT-PCR of a nucleotide sequence of a target gene (see, for example, Table 4, SEQ ID NOS: 149 to 296); 2) for methylation specific or unmethylation specific amplification of a nucleotide sequence of a target gene (see, for example, Table 2, wherein MSP(M) indicates methylation specific primer pairs (e.g., SEQ ID NOS: 3 and 4) and MSP(U) indicates unmethylation specific primer pairs (e.g., SEQ ID NOS: 5 and 6), see, also, Table 3); or 3) for bisulfite PCR (see, for example, Table 2, SEQ ID NOS: 1 and 2).

Accordingly, the present invention provides an oligonucleotide selected from any one of SEQ ID NOS: 1 to 296, and further provides a plurality of such oligonucleotides, which includes at least two (e.g., 2, 3, 4, 5, or more) of the oligonucleotides set forth as SEQ ID NOS: 1 to 296, wherein the amplification primer pair can amplify a nucleotide sequence of a gene as listed in Table 1, in some cases depending, for example, on whether the target sequence is methylated or unmethylated. The present invention also provides an amplification primer pair, which comprises a forward primer and a reverse primer, particularly a primer pair that includes one, and particularly two, of the oligonucleotides of SEQ ID NOS: 1 to 296, which can be a forward primer, a reverse primer or both of a primer pair as set forth in Tables 2, 3 and 4 (e.g., SEQ ID NOS: 1 and 2, SEQ ID NOS: 3 and 4; SEQ ID NOS: 5 and 6, etc.).

In one aspect, an amplification primer pair of the invention can be used to specifically amplify a methylated 5' regulatory region of the nucleic acid molecule, such amplification primer pairs being exemplified by SEQ ID NOS: 23 and 24, SEQ ID NOS: 111 and 112, SEQ ID NOS: 115 and 116, SEQ ID NOS: 119 and 120, SEQ ID NOS: 125 and 126, SEQ ID NOS: 129 and 130, SEQ ID NOS: 133 and 134, SEQ ID NOS: 139 and 140 or SEQ ID NOS: 143 and 144, which can amplify SFRP family members having a methylated 5' regulatory region (see Tables 2 and 3). In another aspect, an amplification primer pair of the invention can be used to specifically amplify an unmethylated 5' regulatory region of the nucleic acid molecule, such amplification primer pairs being exemplified by SEQ ID NOS: 25 and 26, SEQ ID NOS: 113 and 114, SEQ ID NOS: 117 and 118, SEQ ID NOS: 121 and 122, SEQ ID NOS: 127 and 128, SEQ ID NOS: 131 and 132, SEQ ID NOS: 135 and 136, SEQ ID NOS: 141 and 142 or SEQ ID NOS: 145 and 146, which can amplify SFRP family members having an unmethylated 5' regulatory region (see Tables 2 and 3).

The present invention also relates to a kit, which contains at least one isolated oligonucleotide of the invention, including, for example, a plurality of such isolated oligonucleotides. In one embodiment, a plurality of isolated oligonucleotides of a kit of the invention includes at least one amplification primer pair (i.e., a forward primer and a reverse primer), and can include a plurality of amplification primer pairs, including, for example, amplification primer pairs as set forth in Table 2, Table 3, and/or Table 4. As such, a kit of the invention can contain, for example, one or a plurality of methylation specific amplification primer pairs, unmethylation specific amplification primer pairs, or a combination methylation specific amplification primer pairs and unmethylation specific amplification primer pair, including methylation specific primer pairs and unmethylation specific primer pairs useful for amplifying a methylated form or an unmethylated form of a particular gene that is known to be or suspected of being methylation silenced in one or more types of cancer cells.

A kit of the invention can further include additional reagents, which can be useful, for example, for a purpose for which the oligonucleotides of the kit are useful. For example, where a kit contains one or a plurality of methylation specific and/or unmethylation specific amplification primers, the kit can further contain, for example, control polynucleotides, which can be methylated or unmethylated; one or more reagents that modify methylated cytosine residues, and/or one or more reagents for performing an amplification reaction. Where the kit contains one or plurality of oligonucleotides that selectively hybridize to a methylated or to an unmethylated gene sequence, the kit can further contain, for example, a methylation sensitive restriction endonuclease. A kit of the invention also can contain at least a second primer pair, which can, but need not, be one of the above listed primer pairs, and can be useful, for example, for a nested amplification reaction. Such additional primer pairs can be designed based on the expected sequence of the amplified portion of the target gene using the sequence information available in the relevant GenBank Accession No. for the target gene (see Table 1).

In one embodiment, a kit of the invention contains a methylation specific primer pair and an unmethylation specific primer pair, which are specific for the same target gene, thus allowing a user of the kit to determine whether a particular target gene is methylated or unmethylated. In another embodiment, the kit contains a plurality of such methylation specific and unmethylation specific primer pairs, thus allowing a user to determine the methylation of one or more target genes. For example, such a kit can contain a primer pair as set forth in SEQ ID NOS: 3 and 4 (see Table 2; MSP(M)) and a primer pair as set forth in SEQ ID NOS: 5 and 6 (Table 2; MSP(U)), thus providing amplification primer pairs useful for determining whether the 5' regulatory region of the S100A10 gene (see, also, GenBank Acc. No. AA44051; Table 1) is methylated or unmethylated. Additional combinations of methylation and/or unmethylation specific primer pairs can be determined by referring to Tables 2 and 3, thus providing kits that allow a determination of the methylation status of different genes and/or of different members of a gene family such as the SFRP gene family. Such a kit can further contain a primer pair that includes oligonucleotides that selectively hybridize to an expected amplification product generated using the methylation specific or unmethylation specific primer pair, thus providing reagents useful for performing a nested amplification procedure.

A kit of the invention also can contain a detectable label that can be linked to or incorporated into an oligonucleotide of the kit, or a plurality of different detectable labels such that, depending the needs of the user, can be selected for a particular use, and, if desired, reagents for linking or incorporating the detectable label into the oligonucleotide. Alternatively, or in addition, the kit can contain one or more reagents useful for performing a hybridization reaction such that selective hybridization conditions readily are attained; and/or can contain one or more standard nucleic acid molecules, for example, a standard target SFRP1, nucleotide sequence that contains methylated cytosine residues corresponding the region to which the oligonucleotide is designed to selectively hybridize, or a standard target SFRP1 nucleotide sequence that contains unmethylated cytosine residues corresponding to the target sequence, or a combination thereof. Such standards provide several advantages, including, for example, allowing a confirmation that a reaction using a test cell, or extract thereof, functioned properly, or allowing for comparisons among samples examined at different times or collected from different sources.

Where a kit contains one or more oligonucleotides useful for performing a primer extension (or amplification) reaction, the kit can further include reagents for performing the selective hybridization reaction such that the oligonucleotide provides a substrate for the extension reaction; and/or one or more reagents for performing the primer extension (or amplification) reaction, for example, dNTPs, one or more of which can be detectably labeled or otherwise modified for conveniently linking a detectable label; one or a selection of polymerases; and/or one or more standard target nucleic acid molecules. Where a kit of the invention contains two or more oligonucleotides (or primer pairs) such as those exemplified herein or otherwise useful for practicing the methods of the invention, the kit provides a convenient source of reagents from which the skilled artisan can select one or more oligonucleotides (or primer pairs), as desired.

The present invention also relates to a method of reducing or inhibiting unregulated growth of a cell exhibiting epigenetic silenced transcription of at least one gene associated with a cancer. Such a method can be practiced, for example, by restoring expression of a polypeptide encoded by the epigenetic silenced gene in the cell, thereby reducing or inhibiting unregulated growth of the cell. Such expression can be restored, for example, by contacting the cell with a demethylating agent (e.g, a methyltransferase inhibitor), a histone deacetylase inhibitor, or a combination thereof.

In one embodiment, the epigenetic silenced gene is a methylation silenced gene, and the method includes contacting the cell with at least one demethylating agent, for example, DAC. In one aspect, the cell can be contacted with the demethylating agent in vitro, e.g., in a culture medium or other medium conducive to survival of the cell. If desired, the cell contacted with the demethylating agent further can be administered to a subject. In another aspect, the agent can be administered to subject such that the cell exhibiting unregulated growth is contacted with the agent.

In another embodiment, the method includes introducing a polynucleotide encoding the polypeptide into the cell, whereby the polypeptide is expressed from the polynucleotide, thereby restoring expression of the polypeptide in the cell. The polynucleotide can, but need not, be contained in a vector, e.g., a viral vector, and/or can be formulated in a matrix that facilitates introduction of the polynucleotide into a cell, e.g., liposomes or microbubbles. The polynucleotide can be introduced into a cell by contacting the cell with the polynucleotide ex vivo, in which case the cell containing the polynucleotide can, but need not, be administered to a subject. The polynucleotide also can be introduced into a cell by contacting the cell with the polynucleotide in vivo.

The epigenetic silenced gene can be any gene identified using a method as disclosed herein, and examining a particular cell type such as a particular cancer cell type. Epigenetic silenced genes in colorectal cancer cells are exemplified herein by the genes listed in Table 1, for which GenBank Accession Nos. Polynucleotide sequences encompassing portions of the genes of Table 1 can be obtained, for example, by RT-PCR of nucleic acid molecules obtained from colorectal cancer cells using amplification primer pairs as set forth in Table 3 (SEQ ID NOS: 149 to 296). Epigenetic silenced genes in colorectal cancer cells and/or gastric cancer cells are exemplified by PTGS2, CDKN2A, TIMP3, S100A10, SFRP1, CXX1, SEZZ6L, KIAA0786, TIMP2, PCDH8, FOLH1, and SNRPN, which do not exhibit detectable basal expression, and are re-expressed upon treatment with DAC, but not with TSA; HOXA1, GRO3, and DLX7, which exhibit a basal level of expression that is increased upon treatment with DAC, but not TSA; and POR1, MBNL, TRADD, PDIP, RAD23B, RPL13, GNAI2, PPP1R21A, FPGT, and TRIM32, which are up-regulated by TSA alone, whereas their basal expression and up-regulation with DAC vary among genes.

The present invention also relates to a method for selecting a therapeutic strategy for treating a cancer patient. Such a method can be performed, for example, by identifying at least one methylation silenced gene associated with the cancer, according to a method as disclosed herein (i.e., by contacting an array of nucleotide sequences representative of a genome with nucleic acid subtraction products and detecting selective hybridization of nucleic acid subtraction products to a subpopulation of nucleotide sequences of the array; and selecting an agent useful for restoring expression of one or more of the identified methylation silenced gene in cancer cells of the patient. For example, the selected agent can be a polynucleotide encoding an identified methylation silenced gene, for example, a polynucleotide encoding a polypeptide encoded by a PTGS2, CDKN2A, TIMP3, S100A10, SFRP1, CXX1, SEZZ6L, KIAA0786, TIMP2, PCDH8, FOLH1, SNRPN, HOXA1, GRO3, or DLX7 gene, a family member of such a gene, or a combination of such genes. The selected agent for restoring expression of a methylation silenced gene also can be a demethylating agent such as DAC.

Accordingly, the invention provide a method for treating a cancer patient, wherein cancer cells in the patient exhibit epigenetic silenced expression of at least one gene. Such a method can be performed, for example, by restoring expression of one or more epigenetic silenced genes in cancer cells in the patient. For example, where at least one epigenetic silenced gene is a methylation silenced gene, the patient can be treated by administering a demethylating agent to the subject in an amount sufficient to restore expression of the methylation silenced gene(s) in cancer cells in the subject. Alternatively, or in addition, the patient can be treated by administering at least one polynucleotide encoding at least one polypeptide encoded by one or more of the epigenetic silenced genes to the subject under conditions sufficient for expression of the at least one polypeptide in cancer cells in the subject. Where a polynucleotide is administered to the patient, the polynucleotide can be contained in a vector (e.g., a viral vector) preferably an expression vector, and/or can be formulated in a matrix that facilitates uptake of the polynucleotide by a target cancer cell (e.g., in a liposome).

The cancer to be treated according to a method of the invention can be any type of cancer, including, for example, a carcinoma or a sarcoma. For example, wherein the cancer is a colorectal cancer, a gastric cancer, or colorectal cancer and gastric cancer, a patient can be treated by restoring expression of one or more epigenetic silenced genes, including, PTGS2, CDKN2A, TIMP3, S100A10, SFRP1, CXX1, SEZZ6L, KIAA0786, TIMP2, PCDH8, FOLH1, SNRPN, HOXA1, GRO3, DLX7, POR1, MBNL, TRADD, PDIP, RAD23B, RPL13, GNAI2, PPP1R21A, FPGT, TRIM32, a family member thereof, or a combination thereof. The SFRP genes, including SFRP1, SFRP2, SFRP4, and SFRP5, provide an example of a family of genes in which one or more is epigenetically silenced in colorectal cancer cells, gastric cancer cells, or both.

In one embodiment, a method is provided for treating a subject suffering from a colorectal cancer, a gastric cancer, or both, wherein cells associated with the cancer contain at least one methylation silenced gene. Such a method can be performed, for example, by administering an amount of an agent that restores expression of the at least one methylation silenced gene to the subject sufficient to restore expression of the methylation silenced gene in cells associated with the cancer. The agent can be a polynucleotide encoding the at least one methylation silenced gene, for example, a polynucleotide encoding a polypeptide encoded by a PTGS2, CDKN2A, TIMP3, S100A10, SFRP1, CXX1, SEZZ6L, KIAA0786, TIMP2, PCDH8, FOLH1, SNRPN, HOXA1, GRO3, and/or DLX7 gene, a family member thereof, or a combination thereof; or can be a demethylating agent such as DAC. An agent useful for treating a subject suffering from a colorectal cancer, a gastric cancer, or both, can be contacted with cells of the cancer ex vivo, after which the cells can be administered back into the patient; or the agent can be administer to a site of the cancer cells in the patient.

As a result of methylation silenced transcription of one or more genes in a cell, the gene product(s) is not present in the cell and, therefore, there is a loss of function associated with the absence of the encoded gene product(s). For example, SFRP gene family members can counter WNT/frizzled signaling (Finch et al., *Proc. Natl. Acad. Sci., USA* 94:6770-6775, 1997; Rattner et al., *Proc. Natl. Acad. Sci., USA* 94:2859-2963, 1997). As such, loss of function of one or more SFRP genes can abrogate an entire tumor suppressor pathway. Similarly, the PCDH8 gene encodes a member of a cell adhesion molecule family, loss of function of which is known to be important in tumor invasion and metastasis (Strehl et al., *Genomics* 53:81-89, 1998). Accordingly, the methods of the invention are based on providing a cell that exhibits unregulated growth due to epigenetic silenced, particularly methylation silenced, gene expression with the polypeptide encoded by the methylation silenced gene, thereby restoring regulated growth to the cell. As disclosed herein, the polypeptide can be provided to the cell directly, can be expressed from an exogenous polynucleotide that is introduced into the cell and encodes the polypeptide, or by restoring expression of the endogenous methylation silenced gene in the cell. By restoring the polypeptide to a cell exhibiting unregulated growth, or characteristics generally associated with unregulated growth, including, for example, the ability to grow in soft agar, a lack of contact inhibited growth, or refractoriness to programmed cell death, are alleviated.

Expression of one or more methylation silenced genes such as one or more genes shown in Table 1 can restored, for example, by contacting the cells with a demethylating agent such as DAC, which, when incorporated into the genes during replication of the cell results in progeny cells containing unmethylated genes, which can be transcribed. The cells contacted with the demethylating agent can be cells in culture, wherein the demethylating agent is added to the cell culture medium in an amount sufficient to result in demethylation of the target genes, without being toxic to the cells. The cells in culture can be cells of an established cell line, or can be cells, which can be a mixed population of cells, that have been removed from a subject and are being contacted ex vivo, for example, to determine whether contact with the particular demethylating agent can restore expression of the target gene (s), and therefore, can be useful when administered to the subject. Such ex vivo treatment of the cells also can be useful for restoring expression of the target gene, after which the cells, which optionally can be expanded in culture, can be administered back to the subject. Such a method, as well as any of the methods of treatment as disclosed herein, can further include treatments otherwise known in the art as useful for treating a subject having the particular cancer, or that can be newly useful when used in combination with the present methods.

Cells exhibiting methylation silenced gene expression also can be contacted with the demethylating agent in vivo by administering the agent to a subject. Where convenient, the demethylating agent can be administered using, for example, a catheterization procedure, at or near the site of the cells exhibiting unregulated growth in the subject, or into a blood vessel in which the blood is flowing to the site of the cells. Similarly, where an organ, or portion thereof, to be treated can be isolated by a shunt procedure, the agent can be administered via the shunt, thus substantially providing the agent to the site containing the cells. The agent also can be administered systemically or via other routes as disclosed herein or otherwise known in the art.

A polypeptide, which is reduced or absent due to an epigenetic silenced gene, also can be provided to a cell by introducing a polynucleotide encoding the polypeptide into the cell, whereby the polypeptide is expressed from the polynucleotide in the cell. As such, the present invention provides methods of gene therapy, which can be practiced in vivo or ex vivo. For example, where the cell is characterized by methylation silenced transcription of the SFRP1 gene, a polynucleotide having a nucleotide sequence as set forth in GenBank Accession No. N32514 (see Table 1) can be introduced into the target cell.

The polynucleotide can include, in addition to polypeptide coding sequence, operatively linked transcriptional regulatory elements, translational regulatory elements, and the like, and can be in the form of a naked DNA molecule, which can be contained in a vector, or can be formulated in a matrix such as a liposome or microbubbles that facilitates entry of the polynucleotide into the particular cell. As used herein, the term "operatively linked" refers to two or more molecules that are positioned with respect to each other such that they act as a single unit and effect a function attributable to one or both molecules or a combination thereof. For example, a polynucleotide encoding an SFRP1, polypeptide can be operatively linked to a second (or more) coding sequence, such that a chimeric polypeptide can be expressed from the operatively linked coding sequences. The chimeric polypeptide can be a fusion protein, in which the two (or more) encoded polypeptides are translated into a single polypeptide, i.e., are covalently bound through a peptide bond; or can be translated as two discrete peptides that, upon translation, can operatively associate with each other to form a stable complex. Similarly, a polynucleotide sequence encoding a desired polypeptide can be operatively linked to a regulatory element, in which case the regulatory element confers its regulatory effect on the polynucleotide similarly to the way in which the regulatory element would effect a polynucleotide sequence with which it normally is associated with in a cell.

A fusion protein generally demonstrates some or all of the characteristics of each of its polypeptide components, and, therefore, can be useful for restoring gene expression in the cell and can further provide additional advantages. For example, the fusion protein can include a polypeptide, which is otherwise reduced or absent due to epigenetic silencing of its encoding gene, operatively linked to a cell compartment localization domain such that expression of the fusion protein in a cell or loading of the cell with fusion protein allows translocation of the encoded polypeptide to the intracellular compartment such as the nucleus, in which it effects its activity. Cell compartmentalization domains, for example, are well known and include a plasma membrane localization domain, a nuclear localization signal, a mitochondrial membrane localization signal, an endoplasmic reticulum localization signal, and the like, as well as signal peptides, which can direct secretion of a polypeptide from a cell (see, for example, Hancock et al., *EMBO J.* 10:4033-4039, 1991; Buss et al., *Mol. Cell Biol.* 8:3960-3963, 1988; U.S. Pat. No. 5,776,689 each of which is incorporated herein by reference). The fusion protein also can comprise a desired polypeptide operatively linked to a peptide that acts as a ligand for a receptor, a peptide useful as a tag for identifying a cell in which the polypeptide is expressed, or for isolating the fusion protein, or any other peptide or polypeptide of interest, providing the fusion protein has the protein activity of the desired polypeptide, e.g., an SFRP polypeptide activity in countering WNT/frizzled activity. Peptide tags such as a polyhistidine tag peptide, e.g., His-6, which can be detected using a divalent cation such as nickel ion, cobalt ion, or the like; a FLAG epitope, which can be detected using an anti-FLAG antibody (see, for example, Hopp et al., *BioTechnology* 6:1204 (1988); U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione, are well known in the art, and provide a means of detecting the presence of a polypeptide operatively linked thereto. Such tags provide the additional advantage that they can facilitate isolation of the operatively linked polypeptide, for example, where it is desired to obtain the polypeptide in a substantially purified form, such a polypeptide also being useful for practicing methods of the invention.

A polynucleotide encoding a polypeptide otherwise encoded by an epigenetic silenced can be used alone, or can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and encoded polypeptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide encoding the desired polypeptide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

A tetracycline (tet) inducible promoter can be particularly useful for driving expression of a polynucleotide encoding a desired polypeptide. Upon administration of tetracycline, or a tetracycline analog, to a subject containing a polynucleotide operatively linked to a tet inducible promoter, expression of the encoded polypeptide is induced. The polynucleotide also can be operatively linked to tissue specific regulatory element, for example, a liver cell specific regulatory element such as an α-fetoprotein promoter (Kanai et al., *Cancer Res.* 57:461-465, 1997; He et al., *J. Exp. Clin. Cancer Res.* 19:183-187, 2000) or an albumin promoter (Power et al., *Biochem. Biophys. Res. Comm.* 203:1447-1456, 1994; Kuriyama et al., *Int. J. Cancer* 71:470-475, 1997); a muscle cell specific regulatory element such as a myoglobin promoter (Devlin et al., *J. Biol. Chem.* 264:13896-13901, 1989; Yan et al., *J. Biol. Chem.* 276:17361-17366, 2001); a prostate cell specific regulatory element such as the PSA promoter (Schuur et al., *J. Biol. Chem.* 271:7043-7051, 1996; Latham et al., *Cancer Res.* 60:334-341, 2000); a pancreatic cell specific regulatory element such as the elastase promoter (Ornitz et al., *Nature* 313:600-602, 1985; Swift et al., *Genes Devel.* 3:687-696, 1989); a leukocyte specific regulatory element such as the leukosialin (CD43) promoter (Shelley et al., *Biochem. J.* 270:569-576, 1990; Kudo and Fukuda, *J. Biol. Chem.* 270:13298-13302, 1995); or the like, such that expression of the polypeptide is restricted to particular cell in an individual, or to particular cells in a mixed population of cells in culture, for example, an organ culture. Regulatory elements, including tissue specific regulatory elements, many of which are commercially available, are well known in the art (see, for example, InvivoGen; San Diego Calif.).

Viral expression vectors can be particularly useful for introducing a polynucleotide into a cell, particularly a cell in a subject. Viral vectors provide the advantage that they can infect host cells with relatively high efficiency and can infect specific cell types. For example, a polynucleotide encoding a desired polypeptide can be cloned into a baculovirus vector, which then can be used to infect an insect host cell, thereby providing a means to produce large amounts of the encoded polypeptide. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, hepatitis virus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference).

A polynucleotide, which can be contained in a vector, can be introduced into a cell by any of a variety of methods known in the art (Sambrook et al., supra, 1989; Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. A particularly useful method comprises incorporating the polynucleotide into microbubbles, which can be injected into the circulation. An ultrasound source can be positioned such that ultrasound is transmitted to the tumor, wherein circulating microbubbles containing the polynucleotide are disrupted at the site of the tumor due to the ultrasound, thus providing the polynucleotide at the site of the cancer. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events. A polynucleotide of the invention, or a vector containing the polynucleotide can be contained in a cell, for example, a host cell, which allows propagation of a vector containing the polynucleotide, or a helper cell, which allows packaging of a viral vector containing the polynucleotide. The polynucleotide can be transiently contained in the cell, or can be stably maintained due, for example, to integration into the cell genome.

A method of the invention also can be practiced by directly providing desired polypeptide to a cell exhibiting unregulated growth. The polypeptide can be produced and isolated, and formulated as desired, using methods as disclosed herein. The polypeptide can be contacted with the cell in vitro under conditions that result in sufficient permeability of the cell such that the polypeptide can cross the cell membrane, or can be microinjected into the cells. Where the desired polypeptide is contacted with a cell in situ in an organism, it can comprise a fusion protein, which includes a peptide or polypeptide component that facilitates transport across the cell membrane, for example, a human immunodeficiency virus (HIV) TAT protein transduction domain, and can further comprise a nuclear localization domain operatively linked thereto. Alternatively, or in addition, the polypeptide can be formulated in a matrix that facilitates entry of the polypeptide into a cell.

For administration to a living subject, an agent such as a demethylating agent, a polynucleotide, or a polypeptide useful for practicing a therapeutic method of the invention generally is formulated in a composition suitable for administration to the subject. Thus, the invention provides compositions containing an agent that is useful for restoring regulated growth to a cell exhibiting unregulated growth due to methylation silenced transcription of one or more genes. As such, the agents are useful as medicaments for treating a subject suffering from a pathological condition associated with such unregulated growth.

Such compositions generally include a carrier that can is acceptable for formulating and administering the agent to a subject. Such acceptable carriers are well known in the art and include, for example, aqueous solutions such as water or physiologically buffered saline or other solvents or vehicles such as glycols, glycerol, oils such as olive oil or injectable organic esters. An acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of an acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

The agent can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful in a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.*, 91:2580-2585 (1993), which is incorporated herein by reference). In addition, a polynucleotide agent can be introduced into a cell using, for example, adenovirus-polylysine DNA complexes (see, for example, Michael et al., *J. Biol. Chem.* 268:6866-6869 (1993), which is incorporated herein by reference).

The route of administration of the composition containing the therapeutic agent will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are disclosed herein or otherwise known in the art (see, for example, Blondelle et al., supra, 1995; Ecker and Crook, supra, 1995). In addition, a polypeptide agent can be prepared using D-amino acids, or can contain one or more domains based on peptidomimetics, which are organic molecules that mimic the structure of a domain; or based on a peptoid such as a vinylogous peptoid.

A composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the composition to treat a pathologic condition in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

The composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The following example is intended to illustrate but not limit the invention.

Example 1

Genomic Screen for Epigenetic Silenced Gene Associated with Colorectal Cancer

This example provides a method for detecting genes that are epigenetically down-regulated in cancer cells, and confirms the validity of the method by identifying genes that are epigenetically down-regulated in and diagnostic of colorectal cancer cells (see, also, Suzuki et al., *Nature Genet.* 31:141-149, 2002, which is incorporated herein by reference).

Methods

Cell Culture and Tissue Samples

Cell lines were cultured in RPMI 1640 or Minimal Essential Medium (MEM) supplemented with 10% fetal bovine serum. Tissue samples of colorectal cancer and normal colon mucosa were from specimens obtained at the time of clinically indicated surgical procedures.

DAC and TSA Treatment and RNA Preparation

RKO cells were treated with 5-aza-2'-deoxycytidine (DAC; Sigma) and/or trichostatin A (TSA; Wako) as described (Cameron et al., supra, 1999). Briefly, the treatment consisted of DAC (200 nM) for 48 hr, with drug and medium replaced at the 24 hr time point after beginning of treatment, followed by addition of TSA to a final concentration of 300 nM (from a 1.5 mM ethanol dissolved stock) and incubation for an additional 24 hr. Cells also were treated with DAC alone or TSA alone, or mock treated, using the same volumes of PBS and/or ethanol, and/or same amount of the drugs. Some colorectal cancer (CRC) cell lines also were treated for RT-PCR analysis to assess more robust levels of gene expression; treatment was with 5 µM DAC for 72 hr, with drug and medium being replaced every 24 hr. Total RNA was extracted using the TRIZOL Reagent (Gibco/BRL), and used for microarray analysis, cDNA subtraction and RT-PCR.

cDNA Subtraction

Prior to cDNA subtraction, poly A RNA was isolated from total RNA using the MESSAGE MAKER Reagent Assembly kit (Gibco/BRL). cDNA subtraction was performed with the combination treated RKO cell line as the tester, and mock treated cells as the driver by using the PCR-Select™ cDNA subtraction kit (Clontech). Synthesized cDNA was digested with Rsa I, and tester cDNA was ligated to adaptors included in the kit. After hybridization, PCR amplification of the subtracted cDNA was performed using the ADVANTAGE cDNA PCR kit (Clontech).

Microarray Analysis

Microarray analysis was performed using the Mammalian GeneFilters Microarrays™ system (Research Genetics). Filters were generated for approximately 5,000 of the genes analyzed in the Johns Hopkins Comprehensive microarray core, and filters for an additional 5,000 genes were purchased (Human GeneFilters Microarrays™ Release II; Research Genetics). A total of 10,814 genes and ESTs were analyzed. Hybridization of the filters was performed according to manufacturer's recommendation. Briefly, 5 µg of total RNA was reverse transcribed and labeled using oligo $(dT)_{12-18}$ primer and $^{32}$dCTP with SUPERSCRIPT II reverse transcriptase (Gibco/BRL). Hybridization of the filters was allowed to proceed for 12 to 18 hr. Data was analyzed using the PSCAN program (National Institutes of Health). For subtraction-microarray analysis, the 2nd PCR product from cDNA subtraction was labeled with $^{33}$P using the MULTIPRIME DNA labeling system (Amersham). Hybridization and data analysis were performed as described above. Microarray analysis was repeated independently at least three times for each condition, and results for probing the arrays with cDNA for total RNA from mock treated cells were compared to those for hybridizations with subtraction PCR products.

Semi-Quantitative RT-PCR

DNase I (Ambion) treated total RNA (2 µg) was reverse transcribed for single stranded cDNA using oligo $(dT)_{12-18}$ primer with SUPERSCRIPT II reverse transcriptase (Gibco/BRL). PCR reactions were performed in a volume of 50 µl containing 1×PCR buffer (Gibco/BRL), 1.5 mM of $MgCl_2$, 0.3 mM of dNTP, 0.25 µM of each primer and 2 U of Taq polymerase (Gibco/BRL). One hundred ng of cDNA was used for PCR amplification, and all of the genes were amplified with multiple cycle numbers (20 to 35 cycles) to determine appropriate conditions to obtain semi-quantitative differences in their expression levels. GAPDH PCR (25 and 28 cycles) was performed to ensure cDNA quality and loading accuracy. Amplification primer pairs were as shown in Table 4 (SEQ ID NOS: 149 to 296.

Methylation Analysis

Bisulfite modification of genomic DNA was performed as described (Baylin et al., *Proc. Natl. Acad. Sci. USA* 93:9821-9826, 1996, which is incorporated herein by reference). Methylation status was determined by PCR analysis of bisulfite-modified genomic DNA using two procedures. In the first procedure, all genes investigated were analyzed by bisulfite-PCR, followed by digestion with multiple methylated CpG site-specific restriction enzymes (COBRA; Xiong and Laird, *Nucleic Acids Res.* 25:2532-2534, 1997, which is incorporated herein by reference). The second procedure used methylation specific PCR (MSP) for all genes analyzed in multiple cancer cell lines and tissue samples (Baylin et al., supra, 1996). All of the bisulfite PCR and MSP primers were designed according to genomic sequences around presumed transcription start sites of investigated genes.

Methylation and Expression Analysis of the SFRP Genes

Methylation analysis of SFRP2 and SFRP4 was performed using three different MSP primer pairs to cover the 5' CpG islands of each gene. For SFRP5 methylation analysis, two different MSP primer pairs were used. For RT-PCR, SFRP2 sense and antisense primers were designed for exons 2 and 3, respectively; SFRP4 sense and antisense primers were designed for exons 2 and 5, respectively; and SFRP5 sense and antisense primers were designed for exons 2 and 3, respectively. For each gene, the MSP primer pair that best assessed the methylation status of the gene with respect to the expression data in cell lines was used; these primers also were used for analysis of primary CRC tissues.

Results

Microarray Analysis and Categorization of Up-Regulated Genes cDNA microarray technology was used to identify genes up-regulated RKO CRC cells after treatment with low dose DAC, which minimally blocks DNA methylation, and/or TSA, which inhibit histone deacetylase (HDAC) activity. In initial studies, the low dose of DAC used and the short treatment time for the cells resulted in only a few gene alleles being demethylated, which may have led to up-regulation of gene expression (Cameron et al., supra, 1999), and resulted in insufficient sensitivity as evidenced by a failure to detect control genes arrayed on the filters that were known to be synergistically reactivated by the drug combination in RKO cells (Cameron et al., supra, 1999; Toyota et al., *Cancer Res.* 60:4044-4048, 2000). Accordingly, the sensitivity of the screen was increased by performing an initial cDNA subtraction step between mock treated cells (driver) and DAC and TSA treated cells (tester). The PCR product after the second round of subtraction was then used as a probe for microarray hybridization.

Of four control genes that were arrayed on the filters, and known to be methylated in RKO cells, only hMLH1 re-expression could not be detected; however, the other three control genes, p16, TIMP3 and PTGS2 (COX2), were successfully detected, as validated by subsequent PCR study. For unknown genes, those genes that showed no expression in the mock filter (i.e., those with the same intensity as empty spots when probed with non-subtracted cDNA from mock treated cells), and showed detectable expression after probing with the subtraction products between mock and treated cells, were selected for subsequent analysis by semi-quantitative RT-PCR in cells subjected to mock, DAC alone, TSA alone, or combination drug treatment.

From a total of 10,814 genes examined by subtraction microarray, 74 were up-regulated by DAC and/or TSA treatment. These 74 genes could be divided into two groups: Group 1 genes (n=51), which showed no change in expression with TSA alone, a minimal increase in expression following low dose DAC alone, but much stronger induction by the combined DAC and TSA (Table 1); and Group 2 genes (n=23), which show up-regulation by TSA alone, and have a variable initial expression or response to DAC alone. In addition, Group 1 genes could be further subdivided into two groups: Group 1a genes (n=24), which are completely inactivated in mock cells; and Group 1b genes (n=27), which show basal expression detected by RT-PCR.

Fifty-six of the total non-EST genes (Table 1) had characterized chromosomal positions; a putative transcription start site was identified for 46 of the genes by searching all available genome databases. In addition, 5' CpG islands (GC content>60%, CpG to GpC>0.6 and minimum length 200 bp) were identified for 27 of the 56 genes (Gardiner-Garden and Frommer, *J. Mol. Biol.* 20, 261-282, 1987). Failure to find CpG islands in the putative near upstream regions of the remaining genes could indicate either the absence of a CpG rich proximal promoter, a CpG island containing control region located further upstream than could be determined using available genomic data, or that the region identified is not the true transcription start site.

Methylation Analysis of 5' CpG Islands in RKO Cells

The methylation status of the identified CpG islands was analyzed using bisulfite-PCR in combination with methylated CpG site-specific restriction enzymes (Xiong and Laird, supra, 1997) and MSP (Herman et al., supra, 1996), and the results were compared to the expression status. All 12 of the Group 1a genes (including 3 positive control genes) with identifiable 5' CpG islands contained dense methylation of these regions in RKO cells (Table 1) and exhibited no basal expression detected by RT-PCR. Of the 5 Group 1b genes for which 5' CpG islands were identified, three showed partial methylation (Table 1) that corresponded with their low basal expression levels; the other two genes did not exhibit any methylation. In contrast, none of 10 Group 2 genes, independent of basal expression, showed any 5' CpG island methylation (Table 1).

Methylation and Expression Analysis of Group 1a Genes in CRC Lines

The Group 1a genes were further examined with respect to their relevance for cancer. The methylation status and expression of Group 1a genes was examined in a series of 8 CRC cell lines. Hypermethylation of the SFRP1, SEZ6L, PCDH8 and FOLH1, genes was detected in all CRC lines investigated. Five of the 8 cell lines showed total or predominant methylation of KIAA0786. CXX1 was of special interest, because it is located on the X chromosome and is normally inactivated and methylated on one allele and active and unmethylated on the other in female cells. However, only methylated or predominantly methylated CXX1 alleles were detected in 5 of the 8 CRC lines, including RKO cells, and all were derived from male patients except for HT29. SNRPN also is notable in that it is maternally imprinted in humans and hypermethylated in the promoter region CpG island of the silenced allele, and, as expected, normal peripheral blood lymphocytes showed partial methylation in the CpG island around the transcription start site (Sutcliffe et al., *Nature Genet.* 8:52-58, 1994). In contrast, RKO, HCT116, and SW480 CRC cells showed complete methylation and lacked basal expression. S100A10 and TIMP2 methylation was observed only in RKO cells. Importantly, in the methylated cell lines, each of the above genes lacked basal expression, which was restored by incubation with DAC. Despite a lack of methylation, KIAA0786 was not basally expressed in SW480 cells, yet it was reactivated by treatment with DAC.

Methylation Analysis of Group 1a Genes in Primary CRC Tissues

The methylation status of Group 1a genes was examined in primary colon cancers and corresponding normal colon tissues. SFRP1 methylation was observed in primary CRC samples with a strikingly high frequency (17/20), whereas no methylation was detected in 6 of 17 normal tissues from the same individuals with the tumors, or in normal tissue of three individuals whose tumors showed no methylation. In 11 cases, SFRP1 methylation was observed both in tumors and normal counterparts, but tumors showed stronger methylation signals. SFRP1, methylation also was examined in normal colon tissues from two patients without CRC; no methylation was detected.

SEZ6L and KIAA0786 also showed a very high frequency of hypermethylation in primary CRC (13 of 20 cases, and 8 of 20 cases, respectively). Like SFRP1, however, no methylation was detected in these genes in normal colon from individuals whose tumors harbored no methylation, or in the normal colon in 11 of 13 (SEZ6L) and 4 of 8 (KIAA0786) individuals whose tumors were methylated. Some methylation of SEZ6L and KIAA0786 was detected in normal colon from 2 and 4 individuals, respectively, but the tumors showed stronger methylation signals.

As expected, all tissue samples including normal colon mucosa from female patients showed partial methylation of CXX1, which is located on the X-chromosome. However, 3 of 14 male patients showed CXX1, methylation in a tumor-specific manner. S100A10 and TIMP2 methylation was not observed in any primary CRC sample. FOLH1 and PCDH8 were equally methylated in every CRC sample and normal counterpart examined.

Methylation Patterns of Group 1a Genes Link CRC and Gastric Cancers

The present results indicate that SFRP1, SEZ6L, CXX1, KIAA0786, S100A10 and TIMP2 are involved in tumor development and/or progression. As such, these genes were examined in tumor cell lines of other cancer types. A striking pattern of tumor profiling emerged in that complete hypermethylation of SFRP1, SEZ6L, LPPH1 and CXX1, was common in CRC and gastric cancers, whereas only partial or no methylation generally was observed in all other cancer types studied (FIG. 1). The exceptions to this pattern for SFRP1, were notable. The proapoptotic activity of the SFRP1, gene has been demonstrated in MCF7 breast cancer cells, which did not express this gene in the basal state (Melkonyan et al, *Proc. Natl. Acad. Sci. USA* 94:13636-13641, 1997). As disclosed herein, complete methylation of the CpG island region was detected in MCF7 cells, as well as in MDA MB231 breast cancer cells, and 2 of 4 prostate cancer cell lines studied (FIG. 1).

Methylation and Expression Analysis of SFRP Family Members

To further characterize the grouping of hypermethylated genes discussed above, and the potential role for one of the most interesting genes, SFPR1, in CRC cells, additional SFRP genes were examined. Of the five SFRP genes that have been identified, four were found to have dense CpG islands around their first exons. SFRP3, which lacked a 5' CpG island, was expressed at a basal level in each of 7 CRC cell lines tested. However, with a very high frequency, each of the other three SFRP genes was hypermethylated in CRC cell lines, and the hypermethylation was associated with a lack of basal expression, which was restored by DAC treatment.

Methylation analysis of the SFRP genes in primary CRC tissues (n=124) was of particular interest. The genes were not hypermethylated in normal colon, except for trace methylation of SFRP2 in a patient with a colon cancer in which the gene is hypermethylated. Furthermore, normal colon tissue, and cell lines derived from other tissues, expressed the genes in the absence of promoter methylation. However, hypermethylation was observed for all four genes in primary CRC tumors. The frequencies differed in this large analysis, which included expanded data for SFRP1, (SFRP1, 118 of 124, 95.1%; SFRP2, 11 of 124 89.5%; SFRP4, 36 of 124, 29.0%; and SFRP5, $^{73}/_{124}$, 58.9%). Strikingly, 24.1% of cases (30 of 124) showed methylation of all of four SFRP genes with CpG islands, and at least one of the four was methylated in 123 of 124 tumors (99.2%; FIG. 2).

These results demonstrate that logical mining of the initial microarray data markedly extended the gene discovery consequences. The results also reveal an involvement of epigenetic silencing of a gene family which, in CRC, can abrogate a block to WNT oncogene activity. This hypermethylation of the SFRP gene family appears to provide the highest molecular marker coverage yet described for a common human cancer (see Esteller et al., Cancer Res. 61:3225-3229, 2001).

By exploiting the observation that the transcriptional silencing of hypermethylated genes in cancer cells depends on a synergy between the methylation and the activity of HDACs, with the methylation having the dominant effect (Cameron et al., supra, 1999), a method of screening cancer cell genomes for such genes has been developed. The present results validate this concept concerning the nature of chromatin associated with cancer genes silenced in association with promoter hypermethylation, and demonstrate that the methods efficiently identifies genes having a high potential for a role in tumorigenesis.

From the standpoint of transcriptionally repressive chromatin, the disclosed strategy has provided important information about the promoters of genes with various responses to the inhibitors utilized. The results for Group 1a genes confirmed that densely methylated genes will not re-express if exposed to HDAC inhibition alone. In contrast, the results for Group 2 genes revealed that those genes that do re-express or up-regulate expression following HDAC inhibition, alone, have a lack of promoter methylation, even when CpG islands were present in their 5' regions. The present study discloses genes that were up-regulated after treatment of cells with the demethylating agent, DAC, even though the promoters of these genes were unmethylated. Similar findings were previously reported (Soengas et al., Nature 409, 207-211 (2001). While methylation of upstream genes, such as transcription factors, could secondarily result in activation of these genes, another possibility is that inhibitors of DNA methyltransferases (DNMTs), such as DAC, affect these proteins other than by blocking their methylating capacities. Recent studies revealed that DNMTs have the potential directly, and through interaction with HDACs and other corepressor proteins, to repress transcription independently of their methylating activities (Rountree et al., Nature Genet. 25:269-277, 2000; Bachman et al., J. Biol. Chem. 276:32282-32287, 2001; Fuks et al., Nature Genet. 24:88-91, 2000; Fuks et al., EMBO J. 20:2536-2544, 2001; Robertson et al. Nature Genet. 25:338-342, 2000).

Although the present studies initially used established cell lines, which could create a bias towards detection of genes that are altered only in culture or for which promoter hypermethylation is not tumor specific (see, for example, Smiraglia et al., Hum. Mol. Genet 10:1413-1419, 2001), careful analysis of paired primary tumors and normal tissues indicate that the disclosed method is efficient for identifying genes (11 of 12) for which altered expression is associated with hypermethylated 5' CpG islands in primary as well as cultured cells. Seven of the 12 genes detected by the microarray approach, including p16, COX2, TIMP3, SEZ6L, SFRP1, KIAA0786 and CXX1, were methylated specifically in primary tumors or only in regions of normal colon from CRC patients having methylation of those genes in their CRC tumors. Another gene, TIMP2, while not methylated in normal colon, primary CRC tumors, or PBL, was very frequently hypermethylated in malignant lymphomas. A ninth gene, SNRPN, which is an imprinted gene, exhibited methylation in the promoter of the silenced allele. Two other genes were methylated in both normal colon and primary CRC; only S100A10 was not methylated in primary tissues, although analysis of this gene was not extensive, and it has been reported to be down-regulated in prostate cancer (Chetcuti et al., Cancer Res. 61:6331-6334, 2001).

The disclosed microarray approach further identified a substantial number of genes that are hypermethylated in a tumor specific fashion. For example, some genes such as SFRP1 were methylated in some, but not all, normal colon mucosa tissues from patients with CRC, but not subject without CRC. This methylation in the normal tissues can reflect a "field effect", in which premalignant changes occur over a broad region of the colon, or can indicate a tendency for certain CpG islands to become methylated with age in normal colon, as was found for a group of genes frequently hypermethylated in CRC (Toyota et al., Proc. Natl. Acad. Sci. USA 96:8681-8686, 1999). A field effect is more likely because the ages of individuals with no methylation in normal tissues ranged from 53 to 64 years of age, and one 46 year old patient showed methylation in both normal and tumor tissues.

An advantage of the present approach is that most of the genes that were identified have known properties or implied functions that are important for tumorigenesis. For example, most of the Group 1a genes, and many in the other groups, are located in chromosome regions that undergo frequent LOH in cancers, e.g., SFRP1, at chromosome 8p12, SEZ6L at 22q11, and TIMP2 at 17q25 (Table 1). In addition, many of the genes identified encode components of pathways involved in cancer. For example, among the Group 1a genes, SFRP1 antagonizes WNT oncogene signaling (Finch et al., supra, 1997), and breast cancer cells transfected with SFRP1 showed increased sensitivity to proapoptotic stimuli (Melkonyan et al., supra, 1997). SFRP1 under-expression has been observed in the majority of breast carcinomas (Ugolini et al., Oncogene 18:1903-1910, 1999; Ugolini et al., Oncogene 20:5810-5817, 2001). Mouse SEZ6 and rat latrophilin expression is limited to brain, but their human homologues (SEZ6L and KIAA0786) were identified from frequently deleted regions in lung and breast cancers respectively, although their functions in humans remain unclear (Nishioka et al., *Oncogene* 19:6251-6260, 2000; White et al., *Oncogene* 17:3513-3519, 1998). TIMP2 is a member of the tissue inhibitor of matrix metalloproteinase (TIMP) family, which includes TIMP3, a gene that frequently is inactivated by hypermethylation in various malignancies (Bachman et al., *Cancer Res.* 59:798-802, 1999). S100A10, also termed annexin II light chain or p11, forms a heterotetrameric complex with another calcium-binding protein, annexin II heavy chain (p36; Kube et al., *Gene* 102:255-259, 1991). Frequent loss of p36 and p11 protein expression was reported in prostate cancers, possibly due to methylation silencing of the p36 gene (Chetcuti et al., supra, 2001). CXX1 is a putative prenylated protein (Frattini et al., *Genomics* 46:167-169, 1997). SNRPN, which may be involved in pre-mRNA splicing, is located on 15q11-q13, a region that is implicated in Prader-Will syndrome and Angelman syndrome (Nicholls et al., *Trends Genet.* 14:194-200, 1998).

FOLH1, and PCDH8 also have interesting characteristics. Folate metabolism affects DNA methylation, and a folate metabolic enzyme, methylenetetrahydrofolate reductase, may affect susceptibility to human malignancies (Matsuo et al., *Blood* 97:3205-3209, 2001; Song et al., *Cancer Res.* 61:3272-3275, 2001). FOLH1 is involved in folate uptake and may have a role in DNA methylation in cancers (Heston, W. D., *Urology* 3A Suppl: 104-112, 1997). PCDH8 is a member of a cell-cell adhesion molecule family (Strehl et al., *Genomics* 53:81-89, 1998), for which loss of function is important for invasion and metastasis. However, FOLH1, and PCDH8 did not show tumor specific or tumor predominant methylation. FOLH1, was originally characterized as a prostate specific membrane antigen (PSMA), and is strongly expressed in prostate cancers; it has not been studied in colorectal tumors. Among normal tissues, PCDH8 is expressed exclusively in fatal and adult brain. Thus, methylation of FOLH1 and PCDH8 can be a tissue specific phenomenon related to gene expression, since these genes are silent in CRC cell lines and treatment of such cells with DAC leads to re-expression.

The identification of a frequent preference for hypermethylation of multiple genes in gastrointestinal tumors, including hypermethylation of a gene family, SFRP, suggests that a common defect in chromatin constitution can bias multiple genes, which can include a family of related genes, to epigenetic silencing in association with promoter hypermethylation. This results suggests additional methods for identifying genes that are differentially regulated in cancer cells as compared to normal cells.

From a functional standpoint, all of the SFRP genes are considered to counter WNT/frizzled signaling (Finch et al., supra, 1997; Rattner et al., *Proc. Natl. Acad. Sci. USA* 94:2859-2863, 1997; Chang et al., *Hum. Mol. Genet.* 8:575-583, 1999; Abu-Jawdeh et al., *Lab. Invest.* 79:439-447, 1999) As such, loss of function of SFRP genes can abrogate an entire tumor suppressor pathway. For example, APC mutations are common in colon cancer, and can lead to constitutive WNT pathway action (Morin et al., *Science* 275:1787-1790, 1997; Behrens et al., *Science* 280:596-599, 1998). Initial results indicated that APC mutations are frequent throughout CRC tumors with all combinations of hypermethylation of the SFRP genes. However, APC has additional functions (Mimori-Kiyosue and Tsukita, *J. Cell Biol.* 154:1105-1109, 2001). Thus, loss of inhibition of WNT activity through other mechanisms indicates a new functional pathway important to colorectal tumorigenesis.

The presently disclosed approach provides a means to identify the entire spectrum of genes silenced by epigenetic mechanisms in individual cancer types. The finding that the methylation patterns for the newly identified genes map with the specific cancer type initially screened, and a related tumor type (see FIG. 1), confirms the importance of promoter hypermethylation for profiling of human cancers. Notably, CRC and gastric tumors are among the few tumor types to manifest the microsatellite instability phenotype due to losses of mismatch repair function; in each case, the link was a hypermethylation event involving the promoter of the MLH1 gene (Baylin and Herman, *Trends Genet.* 16:168-174, 2000, which is incorporated herein by reference). Thus, panels of such markers are useful for examining and manipulating the pathways that regulate tumorigenesis. Furthermore, the present results demonstrate that a limited number of hypermethylated genes are sufficient to compose comprehensive marker panels for sensitive detection of specific types of human cancer. The above methods provide a means to identify such gene panels in other disorders.

Although the invention has been described with reference to the above example, it will be understood that modifications and variations are encompassed within the spirit and scope of the invention. Accordingly, the invention is limited only by the claims, which follow Tables 1 to 4.

TABLE 1

Genes upregulated by DAC and TSA treatment in RKO cells

| Acc no.[a] | Gene name | Symbol | Location | CpG island[b] | Methylation[c] |
|---|---|---|---|---|---|
| Group 1a | | | | | |
| R80217 | prostaglandin-endoperoxide synthase 2 (prostaglandin G/H synthase and cyclooxygenase)[d] | PTGS2[d] | 1q25.2-q25.3 | yes | yes |
| AA877595 | cyclin-dependent kinase inhibitor 2A (melanoma, p16, inhibits CDK4)[d] | CDKN2A[d] | 9p21 | yes | yes |
| AA099153 | tissue inhibitor of metalloproteinase 3 (Sorsby fundus dystrophy, pseudoinflammatory)[d] | TIMP3[d] | 22q12.3 | yes | yes |
| AA444051 | S100 calcium-binding protein A10 | S100A10 | 1q21 | yes | yes |
| N32514 | secreted frizzled-related protein 1 | SFRP1 | 8p12-p11.1 | yes | yes |
| W72596 | CAAX box 1 | CXX1 | Xq26 | yes | yes |
| H29013 | seizure-related gene 6 (mouse)-like | SEZ6L | 22q11.2-12.1 | yes | yes |
| W74533 | latrophilin | KIAA0786 | 1p31.1 | yes | yes |
| AA486280 | tissue inhibitor of metalloproteinase 2 | TIMP2 | 17q25 | yes | yes |
| H29216 | protocadherin 8 | PCDH8 | 13q14.3-q21.1 | yes | yes |

TABLE 1-continued

Genes upregulated by DAC and TSA treatment in RKO cells

| Acc no.[a] | Gene name | Symbol | Location | CpG island[b] | Methylation[c] |
|---|---|---|---|---|---|
| N64840 | folate hydrolase (prostate-specific membrane antigen) 1 | FOLH1 | 11p11.2 | yes | yes |
| AI017332 | human SNRPN mRNA, 3' UTR, partial sequence | SNRPN | 15q12 | yes | yes |
| N54793 | pregnancy specific β-1-glycoprotein 6 | PSG6 | 19q13.2 | no | |
| H87471 | kynureninase (L-kynurenine hydrolase) | KYNU | 2p23.3-q14.3 | no | |
| AA001432 | laminin, α3 (nicein (150 kD), kalinin (165 kD), BM600 (150 kD), epilegrin) | LAMA3 | 18q11.2 | no | |
| AA034939 | laminin, alpha 2 (merosin, congenital muscular dystrophy, LAMA2) | LAMA2 | 6q22-q23 | no | |
| AI298976 | small inducible cytokine subfamily C, member 1 (lymphotactin) | SCYC1 | 1q21-q25 | no | |
| AA291484 | cytochrome P450, subfamily IVB, polypeptide 1 | CYP4B1 | 1p34-p12 | no | |
| R62603 | Collagen, type VI, α3 | COL6A3 | 2q37 | no | |
| T73558 | deoxyribonuclease I-like 3 | DNASE1L3 | 3p21.1-3p14.3 | no | |
| AA404246 | Homo sapiens hypothetical protein MGC13047 | 10 | | no | |
| AA156424 | EST | | | | |
| H16554 | EST | | | | |
| N67972 | EST | | | | |
| Group 1b | | | | | |
| AA173290 | homeo box A1 | HOXA1 | 7p15.3 | yes | partial |
| AA935273 | GRO3 oncogene | GRO3 | 4q21 | yes | partial |
| AA256304 | distal-less homeobox 7 | DLX7 | 17q21.33 | yes | partial |
| H17115 | stromal antigen 3 | STAG3 | 7 | yes | no |
| AA454880 | heterogeneous nuclear ribonucleoprotein D (AU-rich element RNA-binding protein 1, 37 kD) | HNRPD | 4q21.1-q21.2 | yes | no |
| AA496149 | 3-hydroxy-3-methylglutaryl-Coenzyme A synthase 2 (mitochondrial) | HMGCS2 | 1p13-p12 | no | |
| AA176491 | myogenic factor 6 (herculin) | MYF6 | 12q21 | no | |
| H16793 | chromosome 8 open reading frame 4 | C8orf4 | 8p11.2 | no | |
| H10079 | KIAA0751 gene product | | 8 | no | |
| H59614 | similar to putative insulin-like growth factor II associated protein | | 11p15.5 | uk | |
| AA457731 | SNARE protein | YKT6 | 6 | uk | |
| AA419251 | interferon induced transmembrane protein 1(9-27) | IFITM1 | 11 | uk | |
| N48178 | KIAA0403 protein | | 6 | uk | |
| AA027147 | hypothetical protein MGC3040 | | 3 | uk | |
| H18646 | hypothetical protein FLJ10697 | | 10 | uk | |
| AA013268 | Homo sapiens mRNA containing (CAG)4 repeat, clone CZ-CAG-7 | | UK | uk | |
| AA039857 | EST | | | | |
| AA101632 | EST | | | | |
| AA464518 | EST | | | | |
| AA427754 | EST | | | | |
| H16733 | EST | | | | |
| H88953 | EST | | | | |
| N90849 | EST | | | | |
| N22486 | EST | | | | |
| T62979 | EST | | | | |
| R53558 | EST | | | | |
| R39555 | EST | | | | |
| Group 2 | | | | | |
| AA425908 | partner of RAC1 (arfaptin 2) | PORT | 11p15 | yes | no |
| AA405717 | muscleblind (Drosophila melanogaster)-like | MBNL | 3 | yes | no |
| AA916906 | TNFRSF1A-associated via death domain | TRADD | 16q22 | yes | no |
| AA404394 | for protein disulfide isomerase-related | PDIP | 3 | yes | no |
| AA489678 | RAD23 (S. cerevisiae) homolog B | RAD23B | 3p25.1 | yes | no |
| AA447514 | ribosomal protein L13 | RPL13 | 16q24.3 | yes | no |
| AA071330 | guanine nucleotide binding protein (G protein), α-inhibiting activity polypeptide 2 | GNAI2 | 3p21 | yes | no |
| AA669126 | protein phosphatase 1, regulatory (inhibitor) subunit 12A | PPP1R21A | 12q15-q21 | yes | no |
| R38619 | fucose-1-phosphate guanyltransferase | FPGT | 1 | yes | no |
| AA055503 | tripartite motif-containing 32 | TRIM32 | 9q32-q34.11 | yes | no |
| T66981 | egf-like module containing mucin-like, hormone receptor-like sequence 1 | EMR1 | 19p13.3 | no | |
| AA480906 | protein kinase C binding protein 1 | PRKCBP1 | 20q12 | no | |
| N45318 | phosphoglycerate mutase 2 (muscle) | PGAM2 | 7p13-p12 | no | |
| N30096 | glutathione S-transferase A3 | GSTA3 | 6p12 | no | |
| AA427733 | advillin | ADVIL | 12 | no | |
| N92901 | fatty acid binding protein 4, adipocyte | FABP4 | 8q21 | no | |
| T60149 | hypothetical protein FL13449 | | 13 | uk | |
| AA453578 | human DNA sequence from clone RP11-3J10 on chromosome 9-12-13.3 | | 9p12-p13.3 | uk | |

TABLE 1-continued

Genes upregulated by DAC and TSA treatment in RKO cells

| Acc no.[a] | Gene name | Symbol | Location | CpG island[b] | Methylation[c] |
|---|---|---|---|---|---|
| W81520 | *Homo sapiens* gene from PAC 106H8, similar to Dynamin | | 1 | | uk |
| AA446486 | EST | | | | |
| AA447992 | EST | | | | |
| H94605 | EST | | | | |
| W46439 | EST | | | | |

[a]GenBank accession number.
[b]Yes: CpG island was found around presumed transcription start site or near upstream region; no: no CpG island was found around presumed transcription start site or near upstream region;
uk: upstream genomic sequence is unknown.
[c]Yes: fully methylated; partial: partially methylated; no: no methylation.
[d]Positive control genes.

TABLE 2

Primer sequences for methylation study

| Gene name | Method | sense | antisense |
|---|---|---|---|
| S100A10 | bisulfite PCR | TGAAGAGAAGTTTATAAGAAYGTTTTGT* (1)*** | CAACAAATCCRAAGCTAAAAACTACCCA** (2) |
| | MSP (M) | TCGCGTCGTTTTTTTTATTTATTCGTC (3) | AAACTCACCTTAACCGAAACGCGACG (4) |
| | MSP (U) | GTTTTTGTGTTGTTTTTTTTATTTATTTGTT (5) | AACAAAACTCACCTTAACCAAAAACACA (6) |
| CXX1 | bisulfite PCR | GGAGTTTATGAGAGGGTTGGAGTTT (7) | ATCACCCACTACAAAACRAACCCTA** (8) |
| | MSP (M) | TGGATACGTATTTTCGGCGACGTTTC | CAACGACGCGTCGCPAACCGAATCG |
| | MSP (U) | TGGTTTTTGTGGATATGTATTTTTGGTGAT | AATTCCTCCAACAACACATCACAAACCA |
| SEZ6L | bisulfite PCR | GGGGAATTGGYGTTAAATTTTGTAGGG* | AAACAACTTCCRAAACCCCCTAAAC** |
| | MSP (M) | TTCGGAAGTTGTTTCGGTTCGC | CGAACATCGTAACTACAAAAAACGCG |
| | MSP (U) | GGGTTTTGGAAGTTGTTTTGGTTTGT | AACCACAAACATCATAACTACAAAAAACACA |
| SFRP1 | bisulfite PCR 1 | TGGTTTTGTTTTTTAAGGGGTGTTGAGT (19) | ACACTAACTCCRAAAACTACAAAACTAAA** (20) |
| | bisulfite PCR 2 | TTAGTTTTGTAGTTTTYGGAGTTAGTG* | TCCTACCRCAAACTTCCAAAAACCTCC** |
| | MSP (M) | TGTAGTTTTCGGAGTTAGTGTCGCGC | CCTACGATCGAAAACGAOGCGAACG |
| | MSP (U) | GTTTTGTAGTTTTTGGAGTTAGTGTTGTGT | CTCAACCTACAATCAAAAACAACACAAACA |
| LPHH1 | bisulfite PCR | GTTAAAGTTTAGTTGGTTTTAYGTAATTAT* | CTTTTAATTTCCRTAACCCTCCTTTTAT** |
| | MSP (M) | ATTAATTTTGGAGCGTTTTTCGCGCGTC | TCCACGCACCGMCCAAAAACCCCG |
| | MSP (U) | ATGTATTAATTTTGGAGTGTTTTTTGTGTGTT | TCTCCACACACCAAACCAAAAACCCCA |
| TIMP2 | bisulfite PCR | AGATAAAGAGGAGAGAAAGTTTG | CCPACAACAAAAACCRAAC* |
| | MSP (M) | ATTCGTAGAAGGTAGCGCGGTCGTC | CTCACCTACCCCGCTCGACCGCG |
| | MSP (U) | ATATATTTGTAGAAGGTAGTGTGGTTGTT | TCCTCACCTACCCCACTCAACCACA |
| SNRPN | bisulfite PCR | GTTATYGGTATAGTTGATTTTGT* (39) | CTCCCCCCAAATCATTCCRATAA** (40) |
| FOLH1 | bisulfite PCR | GAGGTATTAGTGAGATTGAGAGAGATTT | CCCTAAAAWACCMCMCA.AAATCCCA |
| | MSP (M) | TTCGTCGTGGTGGTTGGAGGGCGC | CAACGCACACCAACGCGAACGACG |
| | MSP (U) | TTATTTTGTTGTGGTGGTTGGAGGGTGT | CCCCAACACACAACCAACACAAACAACA |
| PCDH8 | bisulfite PCR | AAGGGATTGTTAGAGGTAGGYGGAG* | CACAAAACTCATACCTCCAACCTCA |
| HOXA1 | bisulfite PCR | TTATGGAGGAAGTGAGAAAGTTGG | TCTACACCCCCCTACCCACTAAAA |
| GRO3 | bisulfite PCR | TAGGAATTTGGGGTAGAAAATGAATATTT | ACCCRAACTATATAACTCCCCAAAATC** |

TABLE 2-continued

Primer sequences for methylation study

| Gene name | Method | sense | antisense |
|---|---|---|---|
| DLX7 | bisulfite PCR | GGAGAGTTAGGYGGGTTAGAGTTGA* | CTACAAAAAAAATAACCATATCTCC |
| | MPS (M) | GATTTTTCGCGGCGGTATCGTAGCGC | CAACCCCTTCCTTCGTTAAACAACGCG |
| | MSP (U) | GATTAGATTTTTGTGGTGGTATTGTAGTGT | AACAACCCCTTCCTTCATTAAACAACACA |
| HNRNP | bisulfite PCR | GAAGGGGGTAGGTTAGGGAGAGG (59) | CCACCATAACTCCCTCCTACTC (60) |
| | MSP (M) | TGATCGGGACGCGTCGTTTTTCGTC | CTTCGCCTCCCACTCTCGCGCGACG |
| | MSP (U) | TTATGTGATTGGGATGTGTTGTTTTTTGTT | CCCTTCACCTCCCACTCTCACACAACA |
| STAG3 | bisulfite PCR | TGGTATTTAGGAGGTTGGTGAAATA | ACCCTCAATCTCCTACTCCATTAAA |
| | MSP (M) | GCGGGGTTMAGCGGGTCGTTCGC | AAAAATATACGAACTAATACGCGCCACG |
| | MSP (U) | GGGTGGGGTTAAAGTGGGTTGTTTGT | TTAAAATATACAAACTAATACACACCACA |
| POR1 | bisulfite PCR | GTAGTTGTTGTTGTTGTTGTTGTTT | AACATCTTACCCTCTAAACAAATTTATAC |
| | MSP (M) | GTTTCGTTTTTATAATTTGCGACGTGGTC | CTCAAAACGCCAAACCCGAACCGCG |
| | MSP (U) | GTGATGTTAGTTTTGTTTTTATAATTTGTGAT | TCCCCTCAAAACACCAAACCCAAACCA |
| MBNL | bisulfite PCR | GAATTTATTGGTGTGTTTAGTAGTYGG* | CCCRAACCACAAAATCRCCTATCAAC** |
| | MSP (M) | GGGAGGGCGTTCGGTTTGTACGTTC (79) | CATAAACGATCGCCCAACGACGCCG (80) |
| | MSP (U) | AGTGGGAGGGTGTTTGGTTTGTATGTTT | CAAATCATAAACAATCACCCAACAACACCA |
| RAD23B | bisulfite PCR | AGGAGGAAGTTTTAGGAGTTTTTG | CTAACTCACCACAAAATAATAACC |
| | MSP (M) | TCGTGGTTGGCGTTCGGCGCGTGA | ACCGCCGCGCAACTCGACTACCGA |
| | MSP (U) | TTGTGGTTGGTGTTTGGTGTGTGA | ATACCACCACACAACTCAACTACC |
| RPL13 | bisulfite PCR | GTGTTTTATAAATGTGAATAAATAGAATTT | CAATACACTCTAAAATAATAACAAAACC |
| | MSP (M) | TTTTAGGGTTGTCGGGAGAGTCGCGG | CAACCGAACGAAAAAAAAACGACCCCG |
| | MSP (U) | GTGGTTTTAGGGTTGTTGGGAGAGTTGT | AAAACAACCAAACAAAAAAAAACAACCCCA |
| TRADD | bisulfite PCR | GGTATTAGAAAATTTTGGTTTTTAGGGGG | ACCCACCCACCTACTACACTAACCTA |
| | MSP (M) | ACGGGAAGTAGTTATCGGGAGTTCGC | GACGAAACCTAAATTCCCACGCCCG |
| | MSP (U) | TGGATGGGAAGTAGTTATTGGGAGTTTGT (99) | CTCAACAAAACCTAAATTCCCACACCCA (100) |
| FPGT | bisulfite POR | GTTATTTGTTTTTGAGATYGTTGTTAGAG* | CTAACAACTACCATAACCCCACCTTC |
| PDIR | bisulfite PCR | AGTGGAGAAAGGAGTTAGYGGTGGGTA* | CCTACCTAACATACACRCCCCTCATCCC** |
| GNA12 | bisulfite PCR | GGTTTAGTTATAGGTTTGGTTYGTTTAGG* | CTCACCCAACAACAACAACTTCACCTC |
| MYPT1 | bisulfite POR | GGGTTATATTYGTTTTTTTTGGTGGTTTA* | CCTCCCTTCCTACCACAAAAACCCTC |
| HT2A | bisulfite PCR | GTTTTTAGAGGAAAGTTTATTTTTGTAGGG (109) | ATCCCCAATCCCCAACCCTCCTTCCC (110) |

*Y = C or T
**R = A or G
**SEQ ID NO: - numbered from 1 to 110, from left to right, top to bottom; representative SEQ ID NOS: shown

TABLE 3

Primer sequences for the SFRP genes

| Gene | Method | sense | antisense |
|---|---|---|---|
| SFRP2 | MSP1(M)* | GGGTCGGAGTTTTTCGGAGTTGCGC (111)** | CCGCTCTCTTCGCTAAATACGACTCG (112) |
| | MSP1(U)* | TTTTGGGTTGGAGTTTTTTGGAGTTGTGT | AACCCACTCTCTTCACTAAATACAACTCA |

TABLE 3-continued

Primer sequences for the SFRP genes

| Gene | Method | sense | antisense |
|---|---|---|---|
| | MSP2(M) | AAAATAAGTTCGGGTTTCGGCGGTAC | CAATAAACGAACAAAACGCGAACTACG |
| | MSP2(U) | GTAAAATAAGTTTGGGTTTTGGTGGTAT | CACAATAAACAAAACAAAACACAAACTACA |
| | MSP3(M) | TTAGTATTTGGTCGCGAGGTCGTTC | CCCTAAATACCGCCGCTCGCCCG |
| | MSP3(U) | TTGTTAGTATTTGGTTGTGAGGTTGTTT | CCCCTAAATACCACCACTCACCCA |
| | RT-PCR | GATGATGACAACGACATAATGGAAACG | GAGTGTGCTTGGGGAACGGGAGCT |
| SFRP4 | MSP1(M) | AGTTGTTAAGGGAGCGTTTCGAGTTTAC | CTCAACCTTCGAAAACGAAGCCGCCG |
| | MSP1(U) | GTAGTTGTTAAGGGAGTGTTTTGAGTTTAT | CTCTCAACCTTCAAAAACAAACCCACCA |
| | MSP2(M)* | GGGTGATGTTATCGTTTTTGTATCGAC (129) | CCTCCCCTAACGTAAACTCGAAACG (130) |
| | MSP2(M)* | GGGGGTGATGTTATTGTTTTTGTATTGAT | CACCTCCCCTAACATAAACTCAAAACA |
| | MSP3(M) | GGTTGCGTTTGGAGTTGCGGAGTTC | TCCAATCGACAACAAAACGAAACGCG |
| | MSP3(U) | GTTGGTTGTGTTTTGAGTTGTGGAGTTT | AACTCCAATCAACAACAAAACAAAACACA |
| | RT-PCR | GGTACAGGAAAGGCCTCTTGATGTTG | GGATCTTTTACTAAGCTGATCTCTCC |
| SFRP5 | MSP1(M)* | AAGATTTGGCGTTGGGCGGGACGTTC | ACTCCAACCCGAACCTCGCCGTACG |
| | MSP1(U)* | GTAAGATTTGGTGTTGGGTGGGATGTTT | AAAACTCCAACCCAAACCTCACCATACA |
| | MSP2(M) | CGTTTTGGAGTTGGGGTTAGGCGGTC | AAATAAATAACAACCTACGCTACGAACG |
| | MSP2_(U) | TTTGTTTTGGAGTTGGGGTTAGGTGGTT | CCAAATAAATAACAACCTACACTACAAACA |
| | RT-PCR | TGCGCCCAGTGTGAGATGGAGCAC (147) | CCCATCCCTTAGGCCTTGTGCCAGT (148) |

*Primers shown in FIG. 6 and used in primary tissue sample analysis
**SEQ ID NO: - numbered from 111-148, from left to right, top to bottom; representative SEQ ID NOS: shown

TABLE 4

| Acc No.a | Gene name | Symbol | RT prmer (sense) | RT prmer (antiense) |
|---|---|---|---|---|
| Group 1a | | | | |
| R80217 | prostaglandin-endo-peroxide synthase 2 (prostaglandin G/H synthase and cyclo-oxygenase)d | PTGS2d | TAAACAGACATTTATTTCCAGAC (149)** | GAAAGAAATAGTCAATATGCTTG (150) |
| AA877595 | cyclin-dependent kinase inhibitor 2A (melanoma, p16, inhibits CDK4)d | CDKN2Ad | AGCCTTCGGCTGACTGGCTGG | CTGCCCATCATCATGACCTGGA |
| AA099153 | Tissue inhibitor of metalloproteinase 3 (Sorsby fundus | TIMP3d | CAGCTGGAGCCTGGGGACTG | CCTTGCGCTGGGAGAGGGTGAG |
| AA444051 | S100 calcium-binding protein A10 | S100A10 | TTTCTCTGCTTGTCAAATGAGAGT | CTTAACAAAGGAGGACCTGAGAG |
| N32514 | secreted frizzled-related protein 1 | SERP1 | TTGTAGTTATCTTAGAAGATAGCATGG | ACGGGAATTACTATTAACATAAGCG |
| W72596 | CAAX box 1 | CXX1 | CTGCTGCCGCCCCTGGGCCTCAC (159) | GTAGTGTATTAGAGCAGAGCAGAATG (160) |
| H29013 | seizure related gene 6 (mouse) like | SEZ6L | CCCAGGAGAATGCCTACCTTTG | AAACTGCCAAACAGCCCAGAAGG |
| W74533 | latrophilin | LPHH1 | CTGTGGTTGATTGCTAGTGGT | AAGTGACTGAACCTTGCAGTTCT |

TABLE 4-continued

| Acc No.a | Gene name | Symbol | RT prmer (sense) | RT prmer (antiense) |
|---|---|---|---|---|
| AA486280 | tissue inhibitor of metalloproteinase 2 | TIMP2 | CCCTCCTCGGCAGTGTGTGGGGTC | GGGATGTCAGAGCTGGACCAGTCGAA |
| H29216 | Protocadherin 8 | PCDH8 | ATTACTGTGCTTATAAGTGACACG | GAAGTTATTGCCAAAGGAACTGT |
| N64840 | folate hydrolase (prostate-specific membrane antigen) 1 | FOLH | GTTCGAGGAGGGATGGTGTTTGAGC (169) | ATACCACACAAATTCAATACGGATTCT (170) |
| AI017332 | Human SNRPN mRNA, 3 UTR, partial sequence | SNRPN | AATGACACTCTGAAATCCAGTC | CTATTGTGTGATAGGCTCTGT |
| N54793 | Pregnancy specific beta-1-glycoprotein 6 | PSG6 | TGAGTGGTAGCAAGGTTTACA | ATTTCAGCCTCTTCCGPATCT |
| H87471 | kynureninase (L-kynurenine hydrolase) | KYNU | TTANAAAAATCGAATAATACTGAAATAACC | GGGGTGCCCAGCCTAACAATAA |
| AA001432 | laminin, alpha 3 (nicein (150 kD), kalinin (165 kD), BM600 (150 kD), epilegrin) | LAMA3 | TCTCTGAAGAAGGAGGTCATGT | GGAGGGAGGTGCATTGGGTAAT |
| AA034939 | laminin, alpha 2 (merosin, congenital muscular dystrophy) (LAMA2) | LAMA2 | AAAGCAGTTGGTGGATTCAAAG (179) | TTATTAGTTGGCTGGGCATGA (180) |
| AI298976 | small inducible cytokine subfamily C, member 1 (lymphotactin) | SCYC1 | TTCTTTACACATCAGTCACAAG | GGGTGTTGAGTTACCAGATGA |
| AA291484 | cytochrome P450, subfamily IVB, polypeptide 1 | CYP4B1 | AAAGAAACACATCTCAGTGAAGGG | CAGGAGGCTTGTAGTTTAGAAGG |
| R62603 | Collagen, type VI, alpha 3 | COL6A3 | AGTTAGCCACTGCTGGTGTT | CCCTCCCTCCAGCACACAAA |
| T73558 | deoxyribonuclease I-like 3 | DNASE1L3 | CCAGAGACATCCGTTAAGGAGA | TTGGGTCTAGGAGCGTTTGCT |
| AA404246 | Homo sapiens hypothetical protein MGC13047 | MGC13047 | TCTTGAGCATTGTGGTGGCCTTA (189) | TTCGGGCTTCCTGGAGGGAACA (190) |
| AA156424 | EST | | GCAACATGAAGATTCTGAAGGGT | ACAGCAAACTGCATTTACCATCG |
| H16554 | EST | | TTGGAAAGATCGTCCTGGTGC | AACTTCTGGCCCTCGGAGGAA |
| N67972 | EST | | AACAGCAAGCATGACATATTCA | GCAGAGAGAATGTGAGGAACCTT |
| Group 1b | | | | |
| AA173290 | homeo box A1 | HOXA1 | ATGCCTCAGAGGGTAGCCTTG | ATTACAGACATCCTAAGACCCG |
| AA935273 | GRO3 oncogene | GRO3 | TCATCAAACATAGCTCAGTCCT (199) | CCAAGGGAAAGAGAAACGCTG (200) |
| AA256304 | distal-less homeobox 7 | DLX7 | TTTCTCTGGAGGACAAGCAGTTAG | TTTCTCTGCATCTCTTCTACCTCC |
| H17115 | stromal antigen 3 | STAG3 | ACCTGGAGCTGTTCCTGC | GTAACAGCTCTTCAAGCTCCT |
| AA454880 | Heterogeneous nuclear ribonucleoprotein D (AU-rich element RNA-binding protein 1, 37 kD) | HNRPD | GGTGGTTATGGAGGATATGAC | CCAGTAAGACACTACTACATC |
| AA496149 | 3-hydroxy-3-methyl-glutaryl-Coenzyme A synthase 2 (mitochondrial) | HMGCS2 | ATTTGGAGATTCACAGGAACAGC | CCACTCTTAGCTGGTAAATGAAT |

TABLE 4-continued

| Acc No.a | Gene name | Symbol | RT prmer (sense) | RT prmer (antiense) |
|---|---|---|---|---|
| H10079 | KIAA0751 gene product | KIAA0751 | AACCATCTTGCTTTCCTTAAATTC (209) | CCCACCCTTCTTCACCCGCTTT (210) |
| AA176491 | myogenic factor 6 (herculin) | MYF6 | TACAATACCAGGATCCTCGCACAT | TTGGAACTGCGAGTGGCTTAG |
| H16793 | Chromosome 8 open reading frame 4 | C8ORF4 | TATTATTGTTGCATGACATTTGC | AAAGTGCACCCACATGGATGTTA |
| H59614 | similar to PUTATIVE INSULIN-LIKE GROWTH FACTOR II ASSOCIATED PROTEIN | | GCTTTATTGGGATTGCAAGCGT | GGGCTGCCTGTCTGACCTC |
| AA457731 | SNARE protein | YKT6 | GGGCGGACGCATGATAGCTGTA | GTCTTGTTCTTTGACAGAAGCTC |
| N48178 | KIAA0403 protein | KIAA0403 | TTCACATAGCACACAAGTGAC (219) | GACCTCTACTTCCTTGGAGCTT (220) |
| AA419251 | interferon induced transmembrane protein 1(9-27) | IFITM1 | CACAAGCACGTGCACTTTATTGAA | TAGTAGCCGCCCATAGCCTGC |
| AA027147 | hypothetical protein MGC3040 | MGC3040 | AATGTTTCTCATTAAGTCAGGGT | CCAGCCAATGGCGACTATAGAGA |
| H18646 | Hypothetical protein FLJ10697 | FLJ10697 | CCCACGTTTATTTACATATGA | CTTTTGTGTATATATAGATACTTGC |
| AA013268 | Homo sapiens mRNA containing (CAG)4 repeat, clone CZ-CAG-7 | | GCAGAGTTTCACTGTATCAAC | TGAAGATTGTAGGGCTTAGAT |
| AA039857 | EST | | TATTTGTGGCTCCTTCCCACTT (229) | CCTCCTGCCCTCATGCCTGTAA (230) |
| AA101632 | EST | | CGCGTTGCATCCCTTGGATTGTA | CCACGGTTGGTTAATAGTCCCTT |
| AA464518 | EST | | AAGTACACAAGTGGTAAGTATAG | ACTCTTTGATTACAAGCACTGG |
| AA427754 | EST | | ATGCACACATGTTTAATTGTAG | CGTAGGTATACACGTGCCAT |
| H16733 | EST | | TGCCAAGTGCAATGTTCCAGAAA | TTTCGGGAGAACCCAACCTMG |
| H88953 | EST | | TGCTTAGGATATAGCATGAAA (239) | TATCGGCATAGATATATGAGT (240) |
| N90849 | EST | | AAATGCTTTGGAATCCCTGAGA | TGTGCTTAAGTGGCAGGAT |
| N22486 | EST | | ACAAGTTTGMGAACAAAGCTG | TATGGACATCCAGTTGTTCCAGCA |
| T62979 | EST | | AGGAGGGAAGGGTPACAACTCAT | AGAATGTGGATGACCCCTCGGAAG |
| R53558 | EST | | GTCAGTCTGCTCACTCCACCGT | CGGATGTGGAAACCTTTCAGGA |
| R39555 | EST | | TATCACAAGCATTTATTGAGTACC (249) | TATTCTAGATATTTACTCCTTCG (250) |
| Group 2 | | | | |
| AA425908 | partner of RAC1 (arfaptin 2) | POR1 | ACAAAGGATGTACCATGTCCAA | CAGATCAAGGTGATGCACAAG |
| AA405717 | Muscleblind (Drosophila)-like | MBNL | CATACAGCAAAGTCAACTACTGC | ACGCAGTTCMATTTCATGGTTT |
| AA916906 | TNFRSF1A-associated via death domain | TRADD | TTTGGAGAACCTGGATGGCCT | ATCTGCAGCACCCAGGATGAA |
| AA404394 | for protein disulfide isomerase-related | PDIR | AGAGCCCACGTGGGAAGA | CAGGTATCATTCACAGTGTAAT |
| AA489678 | RAD23 (S. cerevisiae) homolog B | RAD23B | TGCCATGAGATATCTTGATTGT (259) | GGGCCAATGGAGAAATGCAGC (260) |
| AA447514 | ribosomal protein L13 | RPL13 | TATACAGTCTTCCCACTTCACT | TTCTGCCTGATCATCCCATTGTA |
| AA071330 | guanine nucleotide binding protein (G protein), alpha | GNAI2 | AAGCTACGAGAATGAGCAGGTG | GTCTTGTTCTGTGATGAGGGG |

TABLE 4-continued

| Acc No.a | Gene name | Symbol | RT prmer (sense) | RT prmer (antisense) |
|---|---|---|---|---|
| | inhibiting activity polypeptide 2 | | | |
| AA669126 | Myosin phosphatase, target subunit 1 | MYPT1 | GAAGATCAGTTAATGTCACTCC | TGGTAGAAGACAAGATGATTTG |
| R38619 | FUCOSE-1-PHOSPHATE GUANYLYLTRANSFERASE | FPGT | TGAATGACAAAGACATAACATCC | CTCAAGTTATGTGTCCCTATATT |
| AA055503 | TAT-INTERACTIVE PROTEIN, 72-KD | HT2A | TTCCGCTGCATTGCTGGCATGT (269) | GCCTTGGAAGTGCCTAATTGCT (270) |
| T66981 | egf-like module containing, mucin-like, hormone receptor-like sequence 1 | EMR1 | AGTCCCAGACCTCAAGGATCT | GGGTAAATCAGTCAGACAGGC |
| AA480906 | protein kinase C binding protein 1 | PRKCBP1 | CAGCTCAGTCACAGGAGAGA | TACAGTTCGCATCCTCTTAAC |
| N45318 | Phosphoglycerate mutase 2 (muscle) | PGAM2 | CTCACAGGCTTCAACAAGGCA | GGGAGGTGCCTTTATTGCCCA |
| N30096 | glutathione S-transferase A3 | GSTA3 | TAGCATATAATTGGAAAGGGTTC | AAGTGTTACAGAGCCATGGACAA |
| AA427733 | advillin | AVIL | CTTTGACACATTACAGATCTGGG (279) | CATCCTTGCATTCCTTGCTTGTT (280) |
| N92901 | fatty acid binding protein 4, adipocyte | FABP4 | TTAACCAACGTAACCATATTGAATAAA | AGGATGATAAACTGGTGGTGGAAT |
| T60149 | Hypothetical protein FLJ13449 | FLJ13449 | GCACATTAAACAGCATACATACC | CCCTGTTCCTTGTGGAAACCTAT |
| AA453578 | Human DNA sequence from clone RP11-3J10 on chromosome 9p12-13.3 | | TTGCCCATAACTCACTGTGGCCT | AAATCTGGCTGGAACGGGACA |
| W81520 | H. sapiens gene from PAC 106H8, similar to Dynamin | | TGTCTTTAGGAGACGTGAGAAAG | CTTCCACGGATTACTGACAGAG |
| AA446486 | EST | | AACTTAGCACAATTAACTGCAGC (289) | TGCCTGAAATCCCACTACTTGG (290) |
| AA447992 | EST | | CATTTATCTTGATCAAACCCACC | ATGCTTTCTGAAGAGTGAGCCC |
| H94605 | EST | | CGTGGTACCTAAACATGGACAC | TCTCATTGTAGGTCTCCTAAAG |
| W46439 | EST | | TTTGAAGCACTAAGATCAATAC (295) | TTGCGAACGCGTCTGTGA (296) |

*Acc No., Genbank accession number. bCpG island, 'Yes', CpG island was found around presumed transcription start site or near upstream region; 'No', no CpG island was found around presumed transcription start site or near upstream region; 'UK', upstream genomic sequence is unknown. cMethylation, 'Yes', fully methylated. 'Partial', partially methylated. 'No', no methylation. dpositive control genes.
**SEQ ID NO: - numbered from 149 to 296, from left to right, top to bottom; representative SEQ ID NO: shown.

What is claimed is:

1. A method of identifying at least one methylation silenced gene associated with cancer, comprising:
   a) contacting an array of nucleotide sequences representative of a genome with nucleic acid subtraction products, wherein the nucleic acid subtraction products are nucleic acid molecules corresponding to RNA expressed in cancer cells that have been treated with a demethylating agent and an inhibitor of histone deacetylase, under conditions suitable for selective hybridization of the nucleic acid subtraction products to complementary nucleotide sequences of the array; and
   b) detecting selective hybridization of the nucleic acid subtraction products to a subpopulation of nucleotide sequences of the array, wherein the subpopulation of nucleotide sequences are not re-expressed in the presence of the histone deacetylase inhibitor alone and only re-expressed in the presence of the combination of at least one demethylating agent and at least one histone deacetylase inhibitor,
wherein the detected subpopulation of nucleic acid sequences represents silenced genes consisting of methylation silenced genes comprising 5' CpG methylated islands of the cancer cells, thereby identifying at least one methylation silenced gene associated with cancer, wherein the at least one methylation silenced gene comprises SFRP2.

2. The method of claim 1, wherein the nucleic acid molecules corresponding to RNA comprise cDNA.

3. The method of claim 1, wherein the demethylating agent comprises 5-aza-2'-deoxycytidine.

4. The method of claim 1, wherein the at least one methylation silenced gene is associated with one type of cancer.

5. The method of claim 1, wherein the at least one methylation silenced gene further comprises PTGS2, CDKN2A, TIMP3, S100A10, SFRP1, SFRP4, SFRP5, CXX1, SEZZ6L, KIAA0786, TIMP2, PCDH8, FOLH1, SNRPN, or a combination thereof.

6. The method of claim 5, wherein the at least one methylation silenced gene is associated with at least two types of cancer.

7. The method of claim 1, wherein the at least one methylation silenced gene further comprises HOXA1, GRO3, DLX7, or a combination thereof.

8. The method of claim 1, wherein the cancer is a carcinoma or a sarcoma.

9. The method of claim 8, wherein the cancer is colorectal cancer, gastric cancer, or colorectal cancer and gastric cancer.

10. The method of claim 1, wherein the at least one methylation silenced gene further comprises SFRP1, SFRP4, SFRP5, or a combination thereof.

11. The method of claim 1, wherein the at least one methylation silenced gene is epigenetically silenced.

12. The method of claim 1, wherein the at least one methylation silenced gene further comprises PTGS2, CDKN2A, TIMP3, S100A10, SFRP1, SFRP4, SFRP5, CXX1, SEZZ6L, KIAA0786, TIMP2, PCDH8, FOLH1, SNRPN, HOXA1, GRO3, DLX7, or a combination thereof.

13. The method of claim 1, wherein the at least one epigenetically silenced gene further comprises POR1, MBNL, TRADD, PDIP, RAD23B, RPL13, GNAI2, PPP1R21A, FPGT, TRIM32, or a combination thereof.

14. The method of claim 11, wherein the cancer is a carcinoma or a sarcoma.

15. The method of claim 14, wherein the cancer is a colorectal cancer, a gastric cancer, or a colorectal cancer and a gastric cancer.

* * * * *